(12) United States Patent
Yuan et al.

(10) Patent No.: US 10,246,494 B2
(45) Date of Patent: Apr. 2, 2019

(54) POLYPEPTIDES AND ANTIBODIES FOR TREATING HBV INFECTION AND RELATED DISEASES

(71) Applicants: Xiamen University, Xiamen (CN); Xiamen Innovax Biotech Co., Ltd., Xiamen (CN)

(72) Inventors: Quan Yuan, Xiamen (CN); Tianying Zhang, Xiamen (CN); Wenxin Luo, Xiamen (CN); Yixin Chen, Xiamen (CN); Jun Zhang, Xiamen (CN); Ningshao Xia, Xiamen (CN)

(73) Assignees: Xiamen University, Xiamen, Fujian (CN); Yang Sheng Tang Company, Ltd., Haikou, Hainan (CN)

( * ) Notice: Subject to any disclaimer, the term of this patent is extended or adjusted under 35 U.S.C. 154(b) by 0 days.

(21) Appl. No.: 15/649,967

(22) Filed: Jul. 14, 2017

(65) Prior Publication Data

US 2018/0002382 A1    Jan. 4, 2018

Related U.S. Application Data

(62) Division of application No. 14/406,940, filed as application No. PCT/CN2013/076832 on Jun. 6, 2013, now Pat. No. 9,751,914.

(30) Foreign Application Priority Data

Jun. 11, 2012 (CN) .......................... 2012 1 0190329

(51) Int. Cl.
| | | |
|---|---|---|
| C07K 14/005 | (2006.01) | |
| A61K 39/12 | (2006.01) | |
| G01N 33/569 | (2006.01) | |
| C07K 16/08 | (2006.01) | |
| C07K 7/06 | (2006.01) | |
| C12P 21/02 | (2006.01) | |
| A61K 39/00 | (2006.01) | |

(52) U.S. Cl.
CPC ............ *C07K 14/005* (2013.01); *A61K 39/12* (2013.01); *C07K 7/06* (2013.01); *C07K 16/082* (2013.01); *C12P 21/02* (2013.01); *G01N 33/56983* (2013.01); *A61K 2039/505* (2013.01); *A61K 2039/6037* (2013.01); *C07K 2317/24* (2013.01); *C07K 2317/76* (2013.01); *C12N 2730/10122* (2013.01); *C12N 2730/10134* (2013.01); *G01N 2333/02* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly |
| 9,751,914 B2 * | 9/2017 | Yuan .................... C07K 14/005 |
| 2004/0106174 A1 | 6/2004 | Jones et al. |
| 2005/0025782 A1 | 2/2005 | Milich et al. |
| 2009/0311283 A1 | 12/2009 | Sette et al. |

FOREIGN PATENT DOCUMENTS

| | | |
|---|---|---|
| JP | 61-501705 | 8/1986 |
| JP | 2000-514643 | 11/2000 |
| WO | 198504103 | 9/1985 |
| WO | 199739029 | 10/1997 |

OTHER PUBLICATIONS

Zhao et al. (Nature, Scientific Reports, 2017, p. 1-9).*
Anonymous: "EP13804161 Align SEQ ID No. 1-7", retrieved from the Internet: URL:http://ibis.internal.epo.org/exam/jobResult?id=375666 [retrieved on Mar. 7, 2016].
Chen, Y-C., J., et al. "Discontinuous epitopes of hepatitis B surface antigen ferived from a filamentous phage peptide library", Proceedings of the National Academy of Sciences, Mar. 1996, vol. 93, pp. 1997-2001.
Cortese, Riccardo, et al., "Identification of biologically active peptides using random libraries displayed on phage", Current Opinion in Biotechnology, 1995, vol. 6, pp. 73-80.
DeLANGE, Robert J. et al., "Amino-acid sequence of Fragment A, an enzymically active fragment from diphtheria toxin", Proc. Nat. Acad. Sci., USA, 73(1):69-72, 1976.
Dikici, Bunyamin et al., "Failure of therapeutic vaccination using hepatitis B surface antigen vaccine in the immunotolerant phase of children with chronic hepatitis B infection", Journal of Gasteroenterology and Hepatology, 18:218-222, 2003.
Huang, Cheng-Hao et al., "Influence of mutations in hepatitis B virus surface protein on viral antigenicity and phenotype in occult HBV strains from blood donors", Journal of Hepatology, 57(4):720-729, 2012.
International Search Report for PCT/CN2013/076832 dated Sep. 12, 2013.
King, Thomas H. et al., "A whole recombinant yeast-based therapeutic vaccine elicits HBV X, S and core specific T cells in mice and activates human T cells recognizing epitopes linked to viral clearance", PLoS One 9(7)e101904, pp. 1-17, 2014.

(Continued)

*Primary Examiner* — Agnieszka Boesen
(74) *Attorney, Agent, or Firm* — Honigman LLP; Thomas A. Wootton, Esq.; Jonathan P. O'Brien

(57) ABSTRACT

The present invention relates to epitope peptides (or mutants thereof) for treating hepatitis B virus infection, recombinant proteins comprising such epitope peptides (or mutants thereof) and carrier proteins, and uses of such epitope peptides (or mutants thereof) and recombinant proteins. The present invention also relates to antibodies against such epitope peptides, cell lines producing said antibodies, and uses thereof. Furthermore, the present invention relates to vaccines or pharmaceutical compositions for treating or alleviating one or more symptoms associated with hepatitis B virus infection, which comprise the recombinant proteins or antibodies according to the invention, respectively.

23 Claims, 34 Drawing Sheets

Specification includes a Sequence Listing.

(56) References Cited

OTHER PUBLICATIONS

Lee, Chiang W. et al., "Expression and immunogenicity of a recombinant diphtheria toxin fragment A in *streptococcus gordonii*", Applied and Environmental Microbiology, 70(8):4569-4574, 2004.

Lok, Anna S. et al., "Randomized phase II study of GS-4774 as a therapeutic vaccine in virally suppressed patients with chgronic hepatitis B", Journal of Hepatology, 65:509-516, 2016.

Prevnar (Oct. 2008, RTM, Drug Information: Pneumococcal 7-valent conjugate vaccine (Diphtheria CRM197 Protein), for Pediatric Use Only, Wyeth.

Qiu, X., et al., "Identification and characterization of a C (K/R) TC TC motif as a common epitope present in all of hepatitis B surface antigen", The Journal of Immunology, 1996, vol. 156, pp. 3350-3356.

Xu, Dao-Zhen et al., "Results of a phase III clinical trial with an HBsAg-HBIG immunogenic complex therapeutic vaccine for chronic hepatitis B patients: experiences and findings", Journal of Hepatology, 59:450-456, 2013.

Zhu, Yibin et al., "Toward the development of monoclonal antibody-based assays to probe virion-like epitopes in hepatitis B vaccine antigen", Human Vaccines & Immunotherapeutics, 10(4):1013-1023, 2014.

Kim, S.H. et al., "Neutralization of hepatitis B virus (HBV) by human monoclonal antibody against HBV surface antigen (HBsAg) in chimpanzees," Antiviral Research, Elsevier BV, NL, vol. 79, No. 3, pp. 188-191, Sep. 1, 2008.

Motti, C, et al., "Recognition by human sera and immunogenicity of HBsAg mimotopes selected from an M13 phage display library," Gene, Elsevier Science BV, Amsterdam, NL, vol. 146, No. 2, pp. 191-198, Sep. 2, 1994.

Shin, Yong-Won, et al., "Human monoclonal antibody against Hepatitis B virus surface antigen (HBsAG)," Antiviral Research, vol. 75, No. 2, pp. 113-120, Feb. 7, 2007.

Clark, M., "Antibody Humanization: A Case of the 'Emperior's New Clothers'?;" Immunology Today, Aug. 2000, vol. 21, No. 8, 397-402.

Jones, P.T., et al., Replacing the Complementarity-Determing Regions in a Human Antibody With Those From a Mouse; Nature, vol. 321, May 29, 1986; Nature Publishing Group.

Lok, A.S.F, et al., "Chronic Hepatitis B: Update 2009," AASLD Practice Guideline Update, Hepatology, vol. 50, No. 3, Sep. 2009, pp. 661-662 and pp. 1-36.

Morrison, S.L., et al., Chimeric Human Antibody Molecules: Mouse Antigen-Binding Domains With Human Constant Region Domains; Proc. Natl. Acad. Sci. USA; vol. 81, pp. 6821-6855, Nov. 1984, Immunology.

Pluckthun, A., "Antibody Engineering;" Current Opinion in Biotechnology, 1991, 2:238-246.

Riechmann, L., et al, "Reshaping Human Antibodies for Thereapy;" Nature, vol. 332, Mar. 24, 1988.

Zhang, Tian-Ying, et al., "Prolonged Suppression of HBV in Mice by a Novel Antibody that Targets a Unique Epitope on Hepatitis B Surface Antigen," Hepatology, Gut, Apr. 2016; 65:658-67.

Zhao, Jing-Hua et al, Nature, Scientific Reports, Jan. 12, 2017, 6:40199; DOI 10.1038/srep40199 p. 1-9.

\* cited by examiner

FIG. 8B

SEQUENCE LISTING

```
<160> NUMBER OF SEQ ID NOS: 97

<210> SEQ ID NO 1
<211> LENGTH: 7
<212> TYPE: PRT
<213> ORGANISM: Artificial sequence
<220> FEATURE:
<223> OTHER INFORMATION: Synthetically Created Peptide

<400> SEQUENCE: 1

Gly Pro Cys Lys Thr Cys Thr
1               5

<210> SEQ ID NO 2
<211> LENGTH: 7
<212> TYPE: PRT
<213> ORGANISM: Artificial sequence
<220> FEATURE:
<223> OTHER INFORMATION: synthesized

<400> SEQUENCE: 2

Gly Pro Cys Arg Thr Cys Thr
1               5

<210> SEQ ID NO 3
<211> LENGTH: 15
<212> TYPE: PRT
<213> ORGANISM: Artificial sequence
<220> FEATURE:
<223> OTHER INFORMATION: synthesized

<400> SEQUENCE: 3

Ser Thr Thr Thr Ser Thr Gly Pro Cys Lys Thr Cys Thr Thr Pro
1               5                   10                  15

<210> SEQ ID NO 4
<211> LENGTH: 11
<212> TYPE: PRT
<213> ORGANISM: Artificial sequence
<220> FEATURE:
<223> OTHER INFORMATION: synthesized

<400> SEQUENCE: 4

Thr Thr Ser Thr Gly Pro Cys Lys Thr Cys Thr
1               5                   10

<210> SEQ ID NO 5
<211> LENGTH: 9
<212> TYPE: PRT
<213> ORGANISM: Artificial sequence
<220> FEATURE:
<223> OTHER INFORMATION: synthesized

<400> SEQUENCE: 5
```

Cys Lys Thr Cys Thr Thr Pro Ala Gln
1               5

<210> SEQ ID NO 6
<211> LENGTH: 23
<212> TYPE: PRT
<213> ORGANISM: Artificial sequence
<220> FEATURE:
<223> OTHER INFORMATION: synthesized

<400> SEQUENCE: 6

Ser Ser Thr Thr Ser Thr Gly Pro Cys Lys Thr Cys Thr Thr Pro Ala
1               5                   10                  15

Gln Gly Thr Ser Met Phe Pro
            20

<210> SEQ ID NO 7
<211> LENGTH: 38
<212> TYPE: PRT
<213> ORGANISM: Artificial sequence
<220> FEATURE:
<223> OTHER INFORMATION: synthesized

<400> SEQUENCE: 7

Pro Gly Ser Ser Thr Thr Ser Thr Gly Pro Cys Lys Thr Cys Thr Thr
1               5                   10                  15

Pro Ala Gln Gly Thr Ser Met Phe Pro Ser Cys Cys Thr Lys Pro
            20                  25                  30

Thr Asp Gly Asn Cys Thr
        35

<210> SEQ ID NO 8
<211> LENGTH: 9
<212> TYPE: PRT
<213> ORGANISM: Artificial sequence
<220> FEATURE:
<223> OTHER INFORMATION: synthesized

<400> SEQUENCE: 8

Ser Thr Thr Thr Ser Thr Gly Pro Cys
1               5

<210> SEQ ID NO 9
<211> LENGTH: 7
<212> TYPE: PRT
<213> ORGANISM: Artificial sequence
<220> FEATURE:
<223> OTHER INFORMATION: synthesized

<400> SEQUENCE: 9

Ser Thr Gly Pro Cys Lys Thr
1               5

<210> SEQ ID NO 10
<211> LENGTH: 4
<212> TYPE: PRT
<213> ORGANISM: Artificial sequence
<220> FEATURE:
<223> OTHER INFORMATION: synthesized

<400> SEQUENCE: 10

Cys Lys Thr Cys
1

```
<210> SEQ ID NO 11
<211> LENGTH: 15
<212> TYPE: PRT
<213> ORGANISM: Artificial sequence
<220> FEATURE:
<223> OTHER INFORMATION: synthesized

<400> SEQUENCE: 11

Thr Cys Thr Thr Pro Ala Gln Gly Asn Ser Met Phe Pro Ala Gln
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: synthesized

<400> SEQUENCE: 12

Met Glu Asn Ile Ala Ser Gly Leu Leu Gly Pro Leu Leu Val Leu
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: synthesized

<400> SEQUENCE: 13

Leu Gly Pro Leu Leu Val Leu Gln Ala Gly Phe Phe Leu Leu Thr
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: synthesized

<400> SEQUENCE: 14

Ala Gly Phe Phe Leu Leu Thr Lys Ile Leu Thr Ile Pro Gln Ser
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: synthesized

<400> SEQUENCE: 15

Ile Leu Thr Ile Pro Gln Ser Leu Asp Ser Trp Trp Thr Ser Leu
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: synthesized

<400> SEQUENCE: 16

Asp Ser Trp Trp Thr Ser Leu Asn Phe Leu Gly Gly Thr Pro Val
1               5                   10                  15

<210> SEQ ID NO 17
```

<211> LENGTH: 15
<212> TYPE: PRT
<213> ORGANISM: Artificial sequence
<220> FEATURE:
<223> OTHER INFORMATION: synthesized

<400> SEQUENCE: 17

Phe Leu Gly Gly Thr Pro Val Cys Leu Gly Gln Asn Ser Gln Ser
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: synthesized

<400> SEQUENCE: 18

Leu Gly Gln Asn Ser Gln Ser Gln Ile Ser Ser His Ser Pro Thr
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: synthesized

<400> SEQUENCE: 19

Ile Ser Ser His Ser Pro Thr Cys Cys Pro Pro Ile Cys Pro Gly
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: synthesized

<400> SEQUENCE: 20

Cys Pro Pro Ile Cys Pro Gly Tyr Arg Trp Met Cys Leu Arg Arg
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: synthesized

<400> SEQUENCE: 21

Arg Trp Met Cys Leu Arg Arg Phe Ile Ile Phe Leu Cys Ile Leu
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: synthesized

<400> SEQUENCE: 22

Ile Ile Phe Leu Cys Ile Leu Leu Leu Cys Leu Ile Phe Leu Leu
1               5                   10                  15

<210> SEQ ID NO 23
<211> LENGTH: 15

```
<212> TYPE: PRT
<213> ORGANISM: Artificial sequence
<220> FEATURE:
<223> OTHER INFORMATION: synthesized

<400> SEQUENCE: 23

Leu Cys Leu Ile Phe Leu Leu Val Leu Leu Asp Tyr Gln Gly Met
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: synthesized

<400> SEQUENCE: 24

Leu Leu Asp Tyr Gln Gly Met Leu Pro Val Cys Pro Leu Ile Pro
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: synthesized

<400> SEQUENCE: 25

Pro Val Cys Pro Leu Ile Pro Gly Ser Ser Thr Thr Ser Thr Gly
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: synthesized

<400> SEQUENCE: 26

Ser Ser Thr Thr Ser Thr Gly Pro Cys Lys Thr Cys Thr Thr Pro
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: synthesized

<400> SEQUENCE: 27

Cys Lys Thr Cys Thr Thr Pro Ala Gln Gly Thr Ser Met Phe Pro
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: synthesized

<400> SEQUENCE: 28

Gln Gly Thr Ser Met Phe Pro Ser Cys Cys Cys Thr Lys Pro Thr
1               5                   10                  15

<210> SEQ ID NO 29
<211> LENGTH: 15
<212> TYPE: PRT
```

```
<213> ORGANISM: Artificial sequence
<220> FEATURE:
<223> OTHER INFORMATION: synthesized

<400> SEQUENCE: 29

Cys Cys Cys Thr Lys Pro Thr Asp Gly Asn Cys Thr Cys Ile Pro
 1               5                  10                  15

<210> SEQ ID NO 30
<211> LENGTH: 15
<212> TYPE: PRT
<213> ORGANISM: Artificial sequence
<220> FEATURE:
<223> OTHER INFORMATION: synthesized

<400> SEQUENCE: 30

Gly Asn Cys Thr Cys Ile Pro Ile Pro Ser Ser Trp Ala Phe Ala
 1               5                  10                  15

<210> SEQ ID NO 31
<211> LENGTH: 15
<212> TYPE: PRT
<213> ORGANISM: Artificial sequence
<220> FEATURE:
<223> OTHER INFORMATION: synthesized

<400> SEQUENCE: 31

Pro Ser Ser Trp Ala Phe Ala Lys Tyr Leu Trp Glu Trp Ala Ser
 1               5                  10                  15

<210> SEQ ID NO 32
<211> LENGTH: 15
<212> TYPE: PRT
<213> ORGANISM: Artificial sequence
<220> FEATURE:
<223> OTHER INFORMATION: synthesized

<400> SEQUENCE: 32

Tyr Leu Trp Glu Trp Ala Ser Val Arg Phe Ser Trp Leu Ser Leu
 1               5                  10                  15

<210> SEQ ID NO 33
<211> LENGTH: 15
<212> TYPE: PRT
<213> ORGANISM: Artificial sequence
<220> FEATURE:
<223> OTHER INFORMATION: synthesized

<400> SEQUENCE: 33

Arg Phe Ser Trp Leu Ser Leu Leu Val Pro Phe Val Gln Trp Phe
 1               5                  10                  15

<210> SEQ ID NO 34
<211> LENGTH: 15
<212> TYPE: PRT
<213> ORGANISM: Artificial sequence
<220> FEATURE:
<223> OTHER INFORMATION: synthesized

<400> SEQUENCE: 34

Val Pro Phe Val Gln Trp Phe Val Gly Leu Ser Pro Thr Val Trp
 1               5                  10                  15

<210> SEQ ID NO 35
<211> LENGTH: 15
<212> TYPE: PRT
<213> ORGANISM: Artificial sequence
```

```
<220> FEATURE:
<223> OTHER INFORMATION: synthesized

<400> SEQUENCE: 35

Gly Leu Ser Pro Thr Val Trp Leu Ser Val Ile Trp Met Met Trp
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: synthesized

<400> SEQUENCE: 36

Ser Val Ile Trp Met Met Trp Phe Trp Gly Pro Ser Leu Tyr Asn
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: synthesized

<400> SEQUENCE: 37

Trp Gly Pro Ser Leu Tyr Asn Ile Leu Ser Pro Phe Met Pro Leu
1               5                   10                  15

<210> SEQ ID NO 38
<211> LENGTH: 18
<212> TYPE: PRT
<213> ORGANISM: Artificial sequence
<220> FEATURE:
<223> OTHER INFORMATION: synthesized

<400> SEQUENCE: 38

Leu Ser Pro Phe Met Pro Leu Leu Pro Ile Phe Phe Cys Leu Trp Val
1               5                   10                  15

Tyr Ile

<210> SEQ ID NO 39
<211> LENGTH: 226
<212> TYPE: PRT
<213> ORGANISM: Hepatitis B virus

<400> SEQUENCE: 39

Met Glu Asn Ile Ala Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Gln Ile Ser Ser His Ser Pro Thr Cys
    50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Thr Cys Thr Thr Pro Ala
```

```
            115                 120                 125
Gln Gly Thr Ser Met Phe Pro Ser Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Phe Trp Gly Pro Ser Leu Tyr Asn Ile
            195                 200                 205

Leu Ser Pro Phe Met Pro Leu Leu Pro Ile Phe Phe Cys Leu Trp Val
        210                 215                 220

Tyr Ile
225

<210> SEQ ID NO 40
<211> LENGTH: 183
<212> TYPE: PRT
<213> ORGANISM: Hepatitis B virus

<400> SEQUENCE: 40

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro His Arg Arg Arg Ser
                165                 170                 175

Gln Ser Arg Glu Ser Gln Cys
            180

<210> SEQ ID NO 41
<211> LENGTH: 188
<212> TYPE: PRT
<213> ORGANISM: Woodchuck hepatitis B virus

<400> SEQUENCE: 41

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
```

```
            20                  25                  30
Thr Ala Thr Ala Leu Tyr Glu Glu Leu Thr Gly Arg Glu His Cys
        35                  40                  45

Ser Pro His His Thr Thr Ile Arg Gln Ala Leu Val Cys Trp Asp Glu
 50                  55                  60

Leu Thr Lys Leu Ile Ala Trp Met Ser Ser Asn Ile Thr Ser Glu Gln
 65                  70                  75                  80

Val Arg Thr Ile Ile Val Asn Tyr Val Asn Asp Thr Trp Gly Leu Lys
                 85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 42
<211> LENGTH: 535
<212> TYPE: PRT
<213> ORGANISM: Artificial sequence
<220> FEATURE:
<223> OTHER INFORMATION: synthesized

<400> SEQUENCE: 42

Gly Ala Asp Asp Val Val Asp Ser Ser Lys Ser Phe Val Met Glu Asn
 1               5                  10                  15

Phe Ser Ser Tyr His Gly Thr Lys Pro Gly Tyr Val Asp Ser Ile Gln
                 20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
```

```
            195                 200                 205
Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 43
<211> LENGTH: 171
<212> TYPE: PRT
<213> ORGANISM: Artificial sequence
<220> FEATURE:
<223> OTHER INFORMATION: synthesized

<400> SEQUENCE: 43

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
```

```
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Asn Leu Ala Thr Trp Val Gly Ser Asn Leu Glu Asp Gly Gly
65                  70                  75                  80
Gly Gly Ser Gly Gly Gly Gly Thr Gly Ser Phe Glu Phe Gly Gly Gly
                85                  90                  95
Gly Ser Gly Gly Gly Gly Ser Arg Glu Leu Val Val Ser Tyr Val Asn
            100                 105                 110
Val Asn Met Gly Leu Lys Ile Arg Gln Leu Leu Trp Phe His Ile Ser
            115                 120                 125
Cys Leu Thr Phe Gly Arg Glu Thr Val Leu Glu Tyr Leu Val Ser Phe
        130                 135                 140
Gly Val Trp Ile Arg Thr Pro Pro Ala Tyr Arg Pro Pro Asn Ala Pro
145                 150                 155                 160
Ile Leu Ser Thr Leu Pro Glu Thr Thr Val Val
                165                 170

<210> SEQ ID NO 44
<211> LENGTH: 205
<212> TYPE: PRT
<213> ORGANISM: Artificial sequence
<220> FEATURE:
<223> OTHER INFORMATION: synthesized

<400> SEQUENCE: 44

Met Asp Ile Asp Pro Tyr Lys Glu Phe Gly Ala Ser Val Glu Leu Leu
1               5                   10                  15
Ser Phe Leu Pro Ser Asp Phe Phe Pro Ser Ile Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Asn Leu Ala Thr Trp Val Gly Ser Asn Leu Glu Asp Gly Gly
65                  70                  75                  80
Gly Gly Ser Gly Gly Gly Gly Thr Gly Ser Phe Glu Phe Gly Gly Gly
                85                  90                  95
Gly Ser Gly Gly Gly Gly Ser Arg Glu Leu Val Val Ser Tyr Val Asn
            100                 105                 110
Val Asn Met Gly Leu Lys Ile Arg Gln Leu Leu Trp Phe His Ile Ser
            115                 120                 125
Cys Leu Thr Phe Gly Arg Glu Thr Val Leu Glu Tyr Leu Val Ser Phe
        130                 135                 140
Gly Val Trp Ile Arg Thr Pro Pro Ala Tyr Arg Pro Pro Asn Ala Pro
145                 150                 155                 160
Ile Leu Ser Thr Leu Pro Glu Thr Thr Val Val Arg Arg Gly Arg
                165                 170                 175
Ser Pro Arg Arg Arg Thr Pro Ser Pro Arg Arg Arg Ser Gln Ser
            180                 185                 190
Pro His Arg Arg Arg Ser Gln Ser Arg Glu Ser Gln Cys
        195                 200                 205
```

```
<210> SEQ ID NO 45
<211> LENGTH: 171
<212> TYPE: PRT
<213> ORGANISM: Artificial sequence
<220> FEATURE:
<223> OTHER INFORMATION: synthesized

<400> SEQUENCE: 45

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Thr Ile Arg Gln Ala Leu Val Cys Trp Asp Glu
    50                  55                  60

Leu Thr Lys Leu Ile Ala Trp Met Ser Ser Asn Ile Thr Ser Gly Gly
65                  70                  75                  80

Gly Gly Ser Gly Gly Gly Gly Thr Gly Ser Phe Glu Phe Gly Gly Gly
                85                  90                  95

Gly Ser Gly Gly Gly Gly Ser Arg Thr Ile Ile Val Asn Tyr Val Asn
            100                 105                 110

Asp Thr Trp Gly Leu Lys Val Arg Gln Ser Leu Trp Phe His Leu Ser
        115                 120                 125

Cys Leu Thr Phe Gly Gln His Thr Val Gln Glu Phe Leu Val Ser Phe
    130                 135                 140

Gly Val Trp Ile Arg Thr Pro Ala Pro Tyr Arg Pro Pro Asn Ala Pro
145                 150                 155                 160

Ile Leu Ser Thr Leu Pro Glu His Thr Val Ile
                165                 170

<210> SEQ ID NO 46
<211> LENGTH: 15
<212> TYPE: PRT
<213> ORGANISM: Artificial sequence
<220> FEATURE:
<223> OTHER INFORMATION: synthesized

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 177
<212> TYPE: PRT
<213> ORGANISM: Artificial sequence
<220> FEATURE:
<223> OTHER INFORMATION: synthesized

<400> SEQUENCE: 47

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80
```

```
Gly Gly Ser Gly Gly Gly Thr Gly Ser Gly Pro Cys Lys Thr Cys
            85                  90                  95

Thr Glu Phe Gly Gly Gly Ser Gly Gly Gly Ser Arg Glu Leu
            100                 105                 110

Val Val Ser Tyr Val Asn Val Asn Met Gly Leu Lys Ile Arg Gln Leu
            115                 120                 125

Leu Trp Phe His Ile Ser Cys Leu Thr Phe Gly Arg Glu Thr Val Leu
130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val
```

<210> SEQ ID NO 48
<211> LENGTH: 177
<212> TYPE: PRT
<213> ORGANISM: Artificial sequence
<220> FEATURE:
<223> OTHER INFORMATION: synthesized

<400> SEQUENCE: 48

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Gly Pro Cys Arg Thr Cys
            85                  90                  95

Thr Glu Phe Gly Gly Gly Ser Gly Gly Gly Ser Arg Glu Leu
            100                 105                 110

Val Val Ser Tyr Val Asn Val Asn Met Gly Leu Lys Ile Arg Gln Leu
            115                 120                 125

Leu Trp Phe His Ile Ser Cys Leu Thr Phe Gly Arg Glu Thr Val Leu
130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val
```

<210> SEQ ID NO 49
<211> LENGTH: 185
<212> TYPE: PRT
<213> ORGANISM: Artificial sequence
<220> FEATURE:
<223> OTHER INFORMATION: synthesized

<400> SEQUENCE: 49

```
Met Asp Ile Asp Pro Tyr Lys Glu Phe Gly Ala Ser Val Glu Leu Leu
1               5                   10                  15
```

```
Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
 65                  70                  75                  80

Gly Gly Ser Gly Gly Gly Thr Gly Ser Ser Thr Thr Ser Thr
            85                  90                  95

Gly Pro Cys Lys Thr Cys Thr Thr Pro Glu Phe Gly Gly Gly Ser
            100                 105                 110

Gly Gly Gly Gly Ser Arg Glu Leu Val Val Ser Tyr Val Asn Val Asn
        115                 120                 125

Met Gly Leu Lys Ile Arg Gln Leu Leu Trp Phe His Ile Ser Cys Leu
        130                 135                 140

Thr Phe Gly Arg Glu Thr Val Leu Glu Tyr Leu Val Ser Phe Gly Val
145                 150                 155                 160

Trp Ile Arg Thr Pro Pro Ala Tyr Arg Pro Pro Asn Ala Pro Ile Leu
                165                 170                 175

Ser Thr Leu Pro Glu Thr Thr Val Val
            180                 185

<210> SEQ ID NO 50
<211> LENGTH: 181
<212> TYPE: PRT
<213> ORGANISM: Artificial sequence
<220> FEATURE:
<223> OTHER INFORMATION: synthesized

<400> SEQUENCE: 50

Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
 65                  70                  75                  80

Gly Gly Ser Gly Gly Gly Thr Gly Ser Thr Thr Ser Thr Gly Pro
            85                  90                  95

Cys Lys Thr Cys Thr Glu Phe Gly Gly Gly Ser Gly Gly Gly Gly
            100                 105                 110

Ser Arg Glu Leu Val Val Ser Tyr Val Asn Val Asn Met Gly Leu Lys
        115                 120                 125

Ile Arg Gln Leu Leu Trp Phe His Ile Ser Cys Leu Thr Phe Gly Arg
        130                 135                 140

Glu Thr Val Leu Glu Tyr Leu Val Ser Phe Gly Val Trp Ile Arg Thr
145                 150                 155                 160

Pro Pro Ala Tyr Arg Pro Pro Asn Ala Pro Ile Leu Ser Thr Leu Pro
                165                 170                 175

Glu Thr Thr Val Val
            180
```

<210> SEQ ID NO 51
<211> LENGTH: 179
<212> TYPE: PRT
<213> ORGANISM: Artificial sequence
<220> FEATURE:
<223> OTHER INFORMATION: synthesized

<400> SEQUENCE: 51

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Cys Lys Thr Cys Thr Thr
                85                  90                  95

Pro Ala Gln Glu Phe Gly Gly Gly Ser Gly Gly Gly Gly Gly Ser Arg
            100                 105                 110

Glu Leu Val Val Ser Tyr Val Asn Val Asn Met Gly Leu Lys Ile Arg
        115                 120                 125

Gln Leu Leu Trp Phe His Ile Ser Cys Leu Thr Phe Gly Arg Glu Thr
    130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
                165                 170                 175

Thr Val Val
```

<210> SEQ ID NO 52
<211> LENGTH: 193
<212> TYPE: PRT
<213> ORGANISM: Artificial sequence
<220> FEATURE:
<223> OTHER INFORMATION: synthesized

<400> SEQUENCE: 52

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Ser Gly Gly Gly Gly Ser Arg Glu Leu
        115                 120                 125
```

```
Val Val Ser Tyr Val Asn Val Asn Met Gly Leu Lys Ile Arg Gln Leu
            130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Ala Tyr
                165                 170                 175

Arg Pro Pro Asn Ala Pro Ile Leu Ser Thr Leu Pro Glu Thr Thr Val
            180                 185                 190

Val
```

<210> SEQ ID NO 53
<211> LENGTH: 208
<212> TYPE: PRT
<213> ORGANISM: Artificial sequence
<220> FEATURE:
<223> OTHER INFORMATION: synthesized

<400> SEQUENCE: 53

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Pro Gly Ser Ser Thr Thr
                85                  90                  95

Ser Thr Gly Pro Cys Lys Thr Cys Thr Thr Pro Ala Gln Gly Thr Ser
            100                 105                 110

Met Phe Pro Ser Cys Cys Cys Thr Lys Pro Thr Asp Gly Asn Cys Thr
        115                 120                 125

Glu Phe Gly Gly Gly Gly Ser Gly Gly Gly Gly Ser Arg Glu Leu Val
    130                 135                 140

Val Ser Tyr Val Asn Val Asn Met Gly Leu Lys Ile Arg Gln Leu Leu
145                 150                 155                 160

Trp Phe His Ile Ser Cys Leu Thr Phe Gly Arg Glu Thr Val Leu Glu
                165                 170                 175

Tyr Leu Val Ser Phe Gly Val Trp Ile Arg Thr Pro Ala Tyr Arg
            180                 185                 190

Pro Pro Asn Ala Pro Ile Leu Ser Thr Leu Pro Glu Thr Thr Val Val
            195                 200                 205
```

<210> SEQ ID NO 54
<211> LENGTH: 179
<212> TYPE: PRT
<213> ORGANISM: Artificial sequence
<220> FEATURE:
<223> OTHER INFORMATION: synthesized

<400> SEQUENCE: 54

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30
```

```
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Gly Gly
 65                  70                  75                  80

Gly Gly Ser Gly Gly Gly Thr Gly Ser Ser Thr Thr Ser Thr
                85                  90                  95

Gly Pro Cys Glu Phe Gly Gly Gly Ser Gly Gly Gly Ser Arg
                100                 105                 110

Glu Leu Val Val Ser Tyr Val Asn Val Asn Met Gly Leu Lys Ile Arg
            115                 120                 125

Gln Leu Leu Trp Phe His Ile Ser Cys Leu Thr Phe Gly Arg Glu Thr
 130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
                165                 170                 175

Thr Val Val

<210> SEQ ID NO 55
<211> LENGTH: 177
<212> TYPE: PRT
<213> ORGANISM: Artificial sequence
<220> FEATURE:
<223> OTHER INFORMATION: synthesized

<400> SEQUENCE: 55

Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Gly Gly
 65                  70                  75                  80

Gly Gly Ser Gly Gly Gly Thr Gly Ser Ser Thr Gly Pro Cys Lys
                85                  90                  95

Thr Glu Phe Gly Gly Gly Ser Gly Gly Gly Ser Arg Glu Leu
                100                 105                 110

Val Val Ser Tyr Val Asn Val Asn Met Gly Leu Lys Ile Arg Gln Leu
            115                 120                 125

Leu Trp Phe His Ile Ser Cys Leu Thr Phe Gly Arg Glu Thr Val Leu
 130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val

<210> SEQ ID NO 56
<211> LENGTH: 174
<212> TYPE: PRT
<213> ORGANISM: Artificial sequence
```

<220> FEATURE:
<223> OTHER INFORMATION: synthesized

<400> SEQUENCE: 56

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Cys Lys Thr Cys Glu Phe
                85                  90                  95

Gly Gly Gly Gly Ser Gly Gly Gly Ser Arg Glu Leu Val Val Ser
            100                 105                 110

Tyr Val Asn Val Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val
                165                 170

<210> SEQ ID NO 57
<211> LENGTH: 185
<212> TYPE: PRT
<213> ORGANISM: Artificial sequence
<220> FEATURE:
<223> OTHER INFORMATION: synthesized

<400> SEQUENCE: 57

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Thr Cys Thr Thr Pro Ala
                85                  90                  95

Gln Gly Asn Ser Met Phe Pro Ala Gln Glu Phe Gly Gly Gly Ser
            100                 105                 110

Gly Gly Gly Gly Ser Arg Glu Leu Val Val Ser Tyr Val Asn Val Asn
        115                 120                 125

Met Gly Leu Lys Ile Arg Gln Leu Leu Trp Phe His Ile Ser Cys Leu
    130                 135                 140

Thr Phe Gly Arg Glu Thr Val Leu Glu Tyr Leu Val Ser Phe Gly Val
145                 150                 155                 160

Trp Ile Arg Thr Pro Pro Ala Tyr Arg Pro Pro Asn Ala Pro Ile Leu

```
                            165                 170                 175

Ser Thr Leu Pro Glu Thr Thr Val Val
            180                 185

<210> SEQ ID NO 58
<211> LENGTH: 211
<212> TYPE: PRT
<213> ORGANISM: Artificial sequence
<220> FEATURE:
<223> OTHER INFORMATION: synthesized

<400> SEQUENCE: 58

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Gly Pro Cys Lys Thr Cys
                85                  90                  95

Thr Glu Phe Gly Gly Gly Gly Ser Gly Gly Gly Gly Ser Arg Glu Leu
            100                 105                 110

Val Val Ser Tyr Val Asn Val Asn Met Gly Leu Lys Ile Arg Gln Leu
        115                 120                 125

Leu Trp Phe His Ile Ser Cys Leu Thr Phe Gly Arg Glu Thr Val Leu
    130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val Arg Arg Arg Gly Arg Ser Pro Arg Arg Thr Pro Ser Pro Arg
            180                 185                 190

Arg Arg Arg Ser Gln Ser Pro His Arg Arg Arg Ser Gln Ser Arg Glu
        195                 200                 205

Ser Gln Cys
        210

<210> SEQ ID NO 59
<211> LENGTH: 211
<212> TYPE: PRT
<213> ORGANISM: Artificial sequence
<220> FEATURE:
<223> OTHER INFORMATION: synthesized

<400> SEQUENCE: 59

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

Leu Met Asn Leu Ala Thr Trp Val Gly Ser Asn Leu Glu Asp Gly Gly
65                  70                  75                  80

Gly Gly Ser Gly Gly Gly Thr Gly Ser Gly Pro Cys Arg Thr Cys
            85                  90                  95

Thr Glu Phe Gly Gly Gly Ser Gly Gly Gly Ser Arg Glu Leu
            100                 105                 110

Val Val Ser Tyr Val Asn Val Asn Met Gly Leu Lys Ile Arg Gln Leu
            115                 120                 125

Leu Trp Phe His Ile Ser Cys Leu Thr Phe Gly Arg Glu Thr Val Leu
        130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val Arg Arg Arg Gly Arg Ser Pro Arg Arg Arg Thr Pro Ser Pro Arg
            180                 185                 190

Arg Arg Arg Ser Gln Ser Pro His Arg Arg Arg Ser Gln Ser Arg Glu
            195                 200                 205

Ser Gln Cys
    210

<210> SEQ ID NO 60
<211> LENGTH: 219
<212> TYPE: PRT
<213> ORGANISM: Artificial sequence
<220> FEATURE:
<223> OTHER INFORMATION: synthesized

<400> SEQUENCE: 60

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Ser Thr Thr Ser Thr
            85                  90                  95

Gly Pro Cys Lys Thr Cys Thr Thr Pro Glu Phe Gly Gly Gly Gly Ser
            100                 105                 110

Gly Gly Gly Gly Ser Arg Glu Leu Val Val Ser Tyr Val Asn Val Asn
            115                 120                 125

Met Gly Leu Lys Ile Arg Gln Leu Leu Trp Phe His Ile Ser Cys Leu
130                 135                 140

Thr Phe Gly Arg Glu Thr Val Leu Glu Tyr Leu Val Ser Phe Gly Val
145                 150                 155                 160

Trp Ile Arg Thr Pro Pro Ala Tyr Arg Pro Pro Asn Ala Pro Ile Leu
                165                 170                 175

Ser Thr Leu Pro Glu Thr Thr Val Val Arg Arg Arg Gly Arg Ser Pro
            180                 185                 190

Arg Arg Arg Thr Pro Ser Pro Arg Arg Arg Arg Ser Gln Ser Pro His
            195                 200                 205

```
Arg Arg Arg Ser Gln Ser Arg Glu Ser Gln Cys
    210                 215

<210> SEQ ID NO 61
<211> LENGTH: 215
<212> TYPE: PRT
<213> ORGANISM: Artificial sequence
<220> FEATURE:
<223> OTHER INFORMATION: synthesized

<400> SEQUENCE: 61

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Thr Thr Ser Thr Gly Pro
                85                  90                  95

Cys Lys Thr Cys Thr Glu Phe Gly Gly Gly Ser Gly Gly Gly Gly
            100                 105                 110

Ser Arg Glu Leu Val Val Ser Tyr Val Asn Val Asn Met Gly Leu Lys
            115                 120                 125

Ile Arg Gln Leu Leu Trp Phe His Ile Ser Cys Leu Thr Phe Gly Arg
    130                 135                 140

Glu Thr Val Leu Glu Tyr Leu Val Ser Phe Gly Val Trp Ile Arg Thr
145                 150                 155                 160

Pro Pro Ala Tyr Arg Pro Pro Asn Ala Pro Ile Leu Ser Thr Leu Pro
                165                 170                 175

Glu Thr Thr Val Val Arg Arg Gly Arg Ser Pro Arg Arg Arg Thr
            180                 185                 190

Pro Ser Pro Arg Arg Arg Ser Gln Ser Pro His Arg Arg Arg Ser
            195                 200                 205

Gln Ser Arg Glu Ser Gln Cys
    210                 215

<210> SEQ ID NO 62
<211> LENGTH: 213
<212> TYPE: PRT
<213> ORGANISM: Artificial sequence
<220> FEATURE:
<223> OTHER INFORMATION: synthesized

<400> SEQUENCE: 62

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80
```

```
Gly Gly Ser Gly Gly Gly Thr Gly Ser Cys Lys Thr Cys Thr Thr
            85                  90                  95

Pro Ala Gln Glu Phe Gly Gly Gly Ser Gly Gly Gly Gly Ser Arg
            100                 105                 110

Glu Leu Val Val Ser Tyr Val Asn Val Asn Met Gly Leu Lys Ile Arg
            115                 120                 125

Gln Leu Leu Trp Phe His Ile Ser Cys Leu Thr Phe Gly Arg Glu Thr
130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
            165                 170                 175

Thr Val Val Arg Arg Arg Gly Arg Ser Pro Arg Arg Thr Pro Ser
            180                 185                 190

Pro Arg Arg Arg Arg Ser Gln Ser Pro His Arg Arg Ser Gln Ser
            195                 200                 205

Arg Glu Ser Gln Cys
            210

<210> SEQ ID NO 63
<211> LENGTH: 227
<212> TYPE: PRT
<213> ORGANISM: Artificial sequence
<220> FEATURE:
<223> OTHER INFORMATION: synthesized

<400> SEQUENCE: 63

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Thr Thr Ser Thr
            85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Arg Glu Leu
            115                 120                 125

Val Val Ser Tyr Val Asn Val Asn Met Gly Leu Lys Ile Arg Gln Leu
            130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Pro Ala Tyr
            165                 170                 175

Arg Pro Pro Asn Ala Pro Ile Leu Ser Thr Leu Pro Glu Thr Thr Val
            180                 185                 190

Val Arg Arg Arg Gly Arg Ser Pro Arg Arg Thr Pro Ser Pro Arg
            195                 200                 205

Arg Arg Arg Ser Gln Ser Pro His Arg Arg Arg Ser Gln Ser Arg Glu
210                 215                 220
```

<210> SEQ ID NO 64
<211> LENGTH: 242
<212> TYPE: PRT
<213> ORGANISM: Artificial sequence
<220> FEATURE:
<223> OTHER INFORMATION: synthesized

<400> SEQUENCE: 64

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Pro Gly Ser Ser Thr Thr
                85                  90                  95

Ser Thr Gly Pro Cys Lys Thr Cys Thr Thr Pro Ala Gln Gly Thr Ser
            100                 105                 110

Met Phe Pro Ser Cys Cys Cys Thr Lys Pro Thr Asp Gly Asn Cys Thr
        115                 120                 125

Glu Phe Gly Gly Gly Ser Gly Gly Gly Gly Ser Arg Glu Leu Val
    130                 135                 140

Val Ser Tyr Val Asn Val Asn Met Gly Leu Lys Ile Arg Gln Leu Leu
145                 150                 155                 160

Trp Phe His Ile Ser Cys Leu Thr Phe Gly Arg Glu Thr Val Leu Glu
                165                 170                 175

Tyr Leu Val Ser Phe Gly Val Trp Ile Arg Thr Pro Pro Ala Tyr Arg
            180                 185                 190

Pro Pro Asn Ala Pro Ile Leu Ser Thr Leu Pro Glu Thr Thr Val Val
        195                 200                 205

Arg Arg Arg Gly Arg Ser Pro Arg Arg Thr Pro Ser Pro Arg Arg
    210                 215                 220

Arg Arg Ser Gln Ser Pro His Arg Arg Arg Ser Gln Ser Arg Glu Ser
225                 230                 235                 240

Gln Cys

<210> SEQ ID NO 65
<211> LENGTH: 208
<212> TYPE: PRT
<213> ORGANISM: Artificial sequence
<220> FEATURE:
<223> OTHER INFORMATION: synthesized

<400> SEQUENCE: 65

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Gly Gly
 65                  70                  75                  80

Gly Gly Ser Gly Gly Gly Thr Gly Ser Cys Lys Thr Cys Glu Phe
                 85                  90                  95

Gly Gly Gly Gly Ser Gly Gly Gly Ser Arg Glu Leu Val Val Ser
             100                 105                 110

Tyr Val Asn Val Asn Met Gly Leu Lys Ile Arg Gln Leu Leu Trp Phe
             115                 120                 125

His Ile Ser Cys Leu Thr Phe Gly Arg Glu Thr Val Leu Glu Tyr Leu
 130                 135                 140

Val Ser Phe Gly Val Trp Ile Arg Thr Pro Ala Tyr Arg Pro Pro
 145                 150                 155                 160

Asn Ala Pro Ile Leu Ser Thr Leu Pro Glu Thr Thr Val Val Arg Arg
                 165                 170                 175

Arg Gly Arg Ser Pro Arg Arg Thr Pro Ser Pro Arg Arg Arg
                 180                 185                 190

Ser Gln Ser Pro His Arg Arg Ser Gln Ser Arg Glu Ser Gln Cys
             195                 200                 205

<210> SEQ ID NO 66
<211> LENGTH: 177
<212> TYPE: PRT
<213> ORGANISM: Artificial sequence
<220> FEATURE:
<223> OTHER INFORMATION: synthesized

<400> SEQUENCE: 66

Met Asp Ile Asp Pro Tyr Lys Glu Phe Gly Ser Ser Tyr Gln Leu Leu
 1               5                  10                  15

Asn Phe Leu Pro Leu Asp Phe Phe Pro Asp Leu Asn Ala Leu Val Asp
                 20                  25                  30

Thr Ala Thr Ala Leu Tyr Glu Glu Leu Thr Gly Arg Glu His Cys
             35                  40                  45

Ser Pro His His Thr Thr Ile Arg Gln Ala Leu Val Cys Trp Asp Glu
 50                  55                  60

Leu Thr Lys Leu Ile Ala Trp Met Ser Ser Asn Ile Thr Ser Gly Gly
 65                  70                  75                  80

Gly Gly Ser Gly Gly Gly Thr Gly Ser Gly Pro Cys Lys Thr Cys
                 85                  90                  95

Thr Glu Phe Gly Gly Gly Gly Ser Gly Gly Gly Ser Arg Thr Ile
             100                 105                 110

Ile Val Asn Tyr Val Asn Asp Thr Trp Gly Leu Lys Val Arg Gln Ser
             115                 120                 125

Leu Trp Phe His Leu Ser Cys Leu Thr Phe Gly Gln His Thr Val Gln
 130                 135                 140

Glu Phe Leu Val Ser Phe Gly Val Trp Ile Arg Thr Pro Ala Pro Tyr
 145                 150                 155                 160

Arg Pro Pro Asn Ala Pro Ile Leu Ser Thr Leu Pro Glu His Thr Val
                 165                 170                 175

Ile

<210> SEQ ID NO 67
<211> LENGTH: 177

```
<212> TYPE: PRT
<213> ORGANISM: Artificial sequence
<220> FEATURE:
<223> OTHER INFORMATION: synthesized

<400> SEQUENCE: 67

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Thr Ile Arg Gln Ala Leu Val Cys Trp Asp Glu
        50                  55                  60

Leu Thr Lys Leu Ile Ala Trp Met Ser Ser Asn Ile Thr Ser Gly Gly
65                  70                  75                  80

Gly Gly Ser Gly Gly Gly Gly Thr Gly Ser Gly Pro Cys Arg Thr Cys
                85                  90                  95

Thr Glu Phe Gly Gly Gly Gly Ser Gly Gly Gly Ser Arg Thr Ile
            100                 105                 110

Ile Val Asn Tyr Val Asn Asp Thr Trp Gly Leu Lys Val Arg Gln Ser
            115                 120                 125

Leu Trp Phe His Leu Ser Cys Leu Thr Phe Gly Gln His Thr Val Gln
130                 135                 140

Glu Phe Leu Val Ser Phe Gly Val Trp Ile Arg Thr Pro Ala Pro Tyr
145                 150                 155                 160

Arg Pro Pro Asn Ala Pro Ile Leu Ser Thr Leu Pro Glu His Thr Val
                165                 170                 175

Ile

<210> SEQ ID NO 68
<211> LENGTH: 185
<212> TYPE: PRT
<213> ORGANISM: Artificial sequence
<220> FEATURE:
<223> OTHER INFORMATION: synthesized

<400> SEQUENCE: 68

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Thr Ile Arg Gln Ala Leu Val Cys Trp Asp Glu
        50                  55                  60

Leu Thr Lys Leu Ile Ala Trp Met Ser Ser Asn Ile Thr Ser Gly Gly
65                  70                  75                  80

Gly Gly Ser Gly Gly Gly Gly Thr Gly Ser Thr Thr Thr Ser Thr
                85                  90                  95

Gly Pro Cys Lys Thr Cys Thr Thr Pro Glu Phe Gly Gly Gly Gly Ser
            100                 105                 110

Gly Gly Gly Gly Ser Arg Thr Ile Ile Val Asn Tyr Val Asn Asp Thr
            115                 120                 125

Trp Gly Leu Lys Val Arg Gln Ser Leu Trp Phe His Leu Ser Cys Leu
130                 135                 140
```

```
Thr Phe Gly Gln His Thr Val Gln Glu Phe Leu Val Ser Phe Gly Val
145                 150                 155                 160

Trp Ile Arg Thr Pro Ala Pro Tyr Arg Pro Pro Asn Ala Pro Ile Leu
                165                 170                 175

Ser Thr Leu Pro Glu His Thr Val Ile
                180             185
```

<210> SEQ ID NO 69
<211> LENGTH: 181
<212> TYPE: PRT
<213> ORGANISM: Artificial sequence
<220> FEATURE:
<223> OTHER INFORMATION: synthesized

<400> SEQUENCE: 69

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Thr Ile Arg Gln Ala Leu Val Cys Trp Asp Glu
    50                  55                  60

Leu Thr Lys Leu Ile Ala Trp Met Ser Ser Asn Ile Thr Ser Gly Gly
65                  70                  75                  80

Gly Gly Ser Gly Gly Gly Thr Gly Ser Thr Thr Ser Thr Gly Pro
                85                  90                  95

Cys Lys Thr Cys Thr Glu Phe Gly Gly Gly Ser Gly Gly Gly Gly
            100                 105                 110

Ser Arg Thr Ile Ile Val Asn Tyr Val Asn Asp Thr Trp Gly Leu Lys
            115                 120                 125

Val Arg Gln Ser Leu Trp Phe His Leu Ser Cys Leu Thr Phe Gly Gln
130                 135                 140

His Thr Val Gln Glu Phe Leu Val Ser Phe Gly Val Trp Ile Arg Thr
145                 150                 155                 160

Pro Ala Pro Tyr Arg Pro Pro Asn Ala Pro Ile Leu Ser Thr Leu Pro
                165                 170                 175

Glu His Thr Val Ile
            180
```

<210> SEQ ID NO 70
<211> LENGTH: 179
<212> TYPE: PRT
<213> ORGANISM: Artificial sequence
<220> FEATURE:
<223> OTHER INFORMATION: synthesized

<400> SEQUENCE: 70

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Thr Ile Arg Gln Ala Leu Val Cys Trp Asp Glu
    50                  55                  60

Leu Thr Lys Leu Ile Ala Trp Met Ser Ser Asn Ile Thr Ser Gly Gly
65                  70                  75                  80
```

```
Gly Gly Ser Gly Gly Gly Thr Gly Ser Cys Lys Thr Cys Thr Thr
            85                  90                  95
Pro Ala Gln Glu Phe Gly Gly Gly Ser Gly Gly Gly Gly Ser Arg
            100                 105                 110
Thr Ile Ile Val Asn Tyr Val Asn Asp Thr Trp Gly Leu Lys Val Arg
            115                 120                 125
Gln Ser Leu Trp Phe His Leu Ser Cys Leu Thr Phe Gly Gln His Thr
130                 135                 140
Val Gln Glu Phe Leu Val Ser Phe Gly Val Trp Ile Arg Thr Pro Ala
145                 150                 155                 160
Pro Tyr Arg Pro Pro Asn Ala Pro Ile Leu Ser Thr Leu Pro Glu His
                165                 170                 175
Thr Val Ile

<210> SEQ ID NO 71
<211> LENGTH: 193
<212> TYPE: PRT
<213> ORGANISM: Artificial sequence
<220> FEATURE:
<223> OTHER INFORMATION: synthesized

<400> SEQUENCE: 71

Met Asp Ile Asp Pro Tyr Lys Glu Phe Gly Ser Ser Tyr Gln Leu Leu
1               5                   10                  15
Asn Phe Leu Pro Leu Asp Phe Phe Pro Asp Leu Asn Ala Leu Val Asp
                20                  25                  30
Thr Ala Thr Ala Leu Tyr Glu Glu Glu Leu Thr Gly Arg Glu His Cys
            35                  40                  45
Ser Pro His His Thr Thr Ile Arg Gln Ala Leu Val Cys Trp Asp Glu
        50                  55                  60
Leu Thr Lys Leu Ile Ala Trp Met Ser Ser Asn Ile Thr Ser Gly Gly
65                  70                  75                  80
Gly Gly Ser Gly Gly Gly Gly Thr Gly Ser Ser Ser Thr Thr Ser Thr
                85                  90                  95
Gly Pro Cys Lys Thr Cys Thr Thr Pro Ala Gln Gly Thr Ser Met Phe
            100                 105                 110
Pro Glu Phe Gly Gly Gly Gly Ser Gly Gly Gly Gly Ser Arg Thr Ile
        115                 120                 125
Ile Val Asn Tyr Val Asn Asp Thr Trp Gly Leu Lys Val Arg Gln Ser
130                 135                 140
Leu Trp Phe His Leu Ser Cys Leu Thr Phe Gly Gln His Thr Val Gln
145                 150                 155                 160
Glu Phe Leu Val Ser Phe Gly Val Trp Ile Arg Thr Pro Ala Pro Tyr
                165                 170                 175
Arg Pro Pro Asn Ala Pro Ile Leu Ser Thr Leu Pro Glu His Thr Val
            180                 185                 190
Ile

<210> SEQ ID NO 72
<211> LENGTH: 208
<212> TYPE: PRT
<213> ORGANISM: Artificial sequence
<220> FEATURE:
<223> OTHER INFORMATION: synthesized

<400> SEQUENCE: 72
```

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Thr Ile Arg Gln Ala Leu Val Cys Trp Asp Glu
50                      55                  60

Leu Thr Lys Leu Ile Ala Trp Met Ser Ser Asn Ile Thr Ser Gly Gly
65                  70                  75                  80

Gly Gly Ser Gly Gly Gly Thr Gly Ser Pro Gly Ser Ser Thr Thr
            85                  90                  95

Ser Thr Gly Pro Cys Lys Thr Cys Thr Thr Pro Ala Gln Gly Thr Ser
            100                 105                 110

Met Phe Pro Ser Cys Cys Cys Thr Lys Pro Thr Asp Gly Asn Cys Thr
            115                 120                 125

Glu Phe Gly Gly Gly Gly Ser Gly Gly Gly Ser Arg Thr Ile Ile
            130                 135                 140

Val Asn Tyr Val Asn Asp Thr Trp Gly Leu Lys Val Arg Gln Ser Leu
145                 150                 155                 160

Trp Phe His Leu Ser Cys Leu Thr Phe Gly Gln His Thr Val Gln Glu
                165                 170                 175

Phe Leu Val Ser Phe Gly Val Trp Ile Arg Thr Pro Ala Pro Tyr Arg
                180                 185                 190

Pro Pro Asn Ala Pro Ile Leu Ser Thr Leu Pro Glu His Thr Val Ile
                195                 200                 205

<210> SEQ ID NO 73
<211> LENGTH: 174
<212> TYPE: PRT
<213> ORGANISM: Artificial sequence
<220> FEATURE:
<223> OTHER INFORMATION: synthesized

<400> SEQUENCE: 73

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Thr Ile Arg Gln Ala Leu Val Cys Trp Asp Glu
50                      55                  60

Leu Thr Lys Leu Ile Ala Trp Met Ser Ser Asn Ile Thr Ser Gly Gly
65                  70                  75                  80

Gly Gly Ser Gly Gly Gly Thr Gly Ser Cys Lys Thr Cys Glu Phe
            85                  90                  95

Gly Gly Gly Gly Ser Gly Gly Gly Ser Arg Thr Ile Ile Val Asn
            100                 105                 110

Tyr Val Asn Asp Thr Trp Gly Leu Lys Val Arg Gln Ser Leu Trp Phe
            115                 120                 125

His Leu Ser Cys Leu Thr Phe Gly Gln His Thr Val Gln Glu Phe Leu
            130                 135                 140

Val Ser Phe Gly Val Trp Ile Arg Thr Pro Ala Pro Tyr Arg Pro Pro
145                 150                 155                 160

Asn Ala Pro Ile Leu Ser Thr Leu Pro Glu His Thr Val Ile
            165                 170

<210> SEQ ID NO 74
<211> LENGTH: 557
<212> TYPE: PRT
<213> ORGANISM: Artificial sequence
<220> FEATURE:
<223> OTHER INFORMATION: synthesized

<400> SEQUENCE: 74

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

```
Ile Gly Phe Ala Ala Tyr Asn Phe Val Glu Ser Ile Asn Leu Phe
            355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
    515                 520                 525

Leu Phe Phe Glu Ile Lys Ser Gly Gly Gly Ser Gly Gly Gly Gly
530                 535                 540

Ser Gly Gly Gly Gly Ser Gly Pro Cys Lys Thr Cys Thr
545                 550                 555
```

<210> SEQ ID NO 75
<211> LENGTH: 557
<212> TYPE: PRT
<213> ORGANISM: Artificial sequence
<220> FEATURE:
<223> OTHER INFORMATION: synthesized

<400> SEQUENCE: 75

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160
```

-continued

Val Glu Leu Glu Ile Asn Phe Glu Thr Arg Gly Lys Arg Gly Gln Asp
             165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
    195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Gly Gly Gly Ser Gly Gly Gly Gly
    530                 535                 540

Ser Gly Gly Gly Gly Ser Gly Pro Cys Arg Thr Cys Thr
545                 550                 555

<210> SEQ ID NO 76
<211> LENGTH: 565
<212> TYPE: PRT

<213> ORGANISM: Artificial sequence
<220> FEATURE:
<223> OTHER INFORMATION: synthesized

<400> SEQUENCE: 76

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr

```
             385                 390                 395                 400
Val Glu Asp Ser Ile Ile Arg Thr Gly Phe Gln Gly Glu Ser Gly His
                405                 410                 415
Asp Ile Lys Ile Thr Ala Glu Asn Thr Pro Leu Pro Ile Ala Gly Val
                420                 425                 430
Leu Leu Pro Thr Ile Pro Gly Lys Leu Asp Val Asn Lys Ser Lys Thr
                435                 440                 445
His Ile Ser Val Asn Gly Arg Lys Ile Arg Met Arg Cys Arg Ala Ile
                450                 455                 460
Asp Gly Asp Val Thr Phe Cys Arg Pro Lys Ser Pro Val Tyr Val Gly
465                 470                 475                 480
Asn Gly Val His Ala Asn Leu His Val Ala Phe His Arg Ser Ser Ser
                485                 490                 495
Glu Lys Ile His Ser Asn Glu Ile Ser Ser Asp Ser Ile Gly Val Leu
                500                 505                 510
Gly Tyr Gln Lys Thr Val Asp His Thr Lys Val Asn Ser Lys Leu Ser
                515                 520                 525
Leu Phe Phe Glu Ile Lys Ser Gly Gly Gly Ser Gly Gly Gly Gly
                530                 535                 540
Ser Gly Gly Gly Gly Ser Ser Thr Thr Thr Ser Thr Gly Pro Cys Lys
545                 550                 555                 560
Thr Cys Thr Thr Pro
                565

<210> SEQ ID NO 77
<211> LENGTH: 561
<212> TYPE: PRT
<213> ORGANISM: Artificial sequence
<220> FEATURE:
<223> OTHER INFORMATION: synthesized

<400> SEQUENCE: 77

Gly Ala Asp Asp Val Val Asp Ser Ser Lys Ser Phe Val Met Glu Asn
1               5                   10                  15
Phe Ser Ser Tyr His Gly Thr Lys Pro Gly Tyr Val Asp Ser Ile Gln
                20                  25                  30
Lys Gly Ile Gln Lys Pro Lys Ser Gly Thr Gln Gly Asn Tyr Asp Asp
                35                  40                  45
Asp Trp Lys Glu Phe Tyr Ser Thr Asp Asn Lys Tyr Asp Ala Ala Gly
                50                  55                  60
Tyr Ser Val Asp Asn Glu Asn Pro Leu Ser Gly Lys Ala Gly Gly Val
65                  70                  75                  80
Val Lys Val Thr Tyr Pro Gly Leu Thr Lys Val Leu Ala Leu Lys Val
                85                  90                  95
Asp Asn Ala Glu Thr Ile Lys Lys Glu Leu Gly Leu Ser Leu Thr Glu
                100                 105                 110
Pro Leu Met Glu Gln Val Gly Thr Glu Glu Phe Ile Lys Arg Phe Gly
                115                 120                 125
Asp Gly Ala Ser Arg Val Val Leu Ser Leu Pro Phe Ala Glu Gly Ser
                130                 135                 140
Ser Ser Val Glu Tyr Ile Asn Asn Trp Glu Gln Ala Lys Ala Leu Ser
145                 150                 155                 160
Val Glu Leu Glu Ile Asn Phe Glu Thr Arg Gly Lys Arg Gly Gln Asp
                165                 170                 175
Ala Met Tyr Glu Tyr Met Ala Gln Ala Cys Ala Gly Asn Arg Val Arg
```

```
            180                 185                 190
Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Gly Gly Gly Ser Gly Gly Gly Gly
    530                 535                 540

Ser Gly Gly Gly Gly Ser Thr Thr Ser Thr Gly Pro Cys Lys Thr Cys
545                 550                 555                 560

Thr

<210> SEQ ID NO 78
<211> LENGTH: 559
<212> TYPE: PRT
<213> ORGANISM: Artificial sequence
<220> FEATURE:
```

<223> OTHER INFORMATION: synthesized

<400> SEQUENCE: 78

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400
```

```
Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Gly Gly Gly Ser Gly Gly Gly
    530                 535                 540

Ser Gly Gly Gly Ser Cys Lys Thr Cys Thr Thr Pro Ala Gln
545                 550                 555
```

<210> SEQ ID NO 79
<211> LENGTH: 573
<212> TYPE: PRT
<213> ORGANISM: Artificial sequence
<220> FEATURE:
<223> OTHER INFORMATION: synthesized

<400> SEQUENCE: 79

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205
```

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
        340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
        420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
        500                 505                 510

Gly Tyr Gln Lys Thr Val Asp His Thr Lys Val Asn Ser Lys Leu Ser
            515                 520                 525

Leu Phe Phe Glu Ile Lys Ser Gly Gly Gly Ser Gly Gly Gly Gly
530                 535                 540

Ser Gly Gly Gly Gly Ser Ser Ser Thr Thr Ser Thr Gly Pro Cys Lys
545                 550                 555                 560

Thr Cys Thr Thr Pro Ala Gln Gly Thr Ser Met Phe Pro
            565                 570

<210> SEQ ID NO 80
<211> LENGTH: 588
<212> TYPE: PRT
<213> ORGANISM: Artificial sequence
<220> FEATURE:
<223> OTHER INFORMATION: synthesized

<400> SEQUENCE: 80

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
        370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
```

```
                420             425             430
Leu Leu Pro Thr Ile Pro Gly Lys Leu Asp Val Asn Lys Ser Lys Thr
            435             440             445

His Ile Ser Val Asn Gly Arg Lys Ile Arg Met Arg Cys Arg Ala Ile
            450             455             460

Asp Gly Asp Val Thr Phe Cys Arg Pro Lys Ser Pro Val Tyr Val Gly
465             470             475             480

Asn Gly Val His Ala Asn Leu His Val Ala Phe His Arg Ser Ser Ser
            485             490             495

Glu Lys Ile His Ser Asn Glu Ile Ser Ser Asp Ser Ile Gly Val Leu
            500             505             510

Gly Tyr Gln Lys Thr Val Asp His Thr Lys Val Asn Ser Lys Leu Ser
            515             520             525

Leu Phe Phe Glu Ile Lys Ser Gly Gly Gly Ser Gly Gly Gly Gly
            530             535             540

Ser Gly Gly Gly Ser Pro Gly Ser Ser Thr Thr Ser Thr Gly Pro
545             550             555             560

Cys Lys Thr Cys Thr Thr Pro Ala Gln Gly Thr Ser Met Phe Pro Ser
            565             570             575

Cys Cys Cys Thr Lys Pro Thr Asp Gly Asn Cys Thr
            580             585

<210> SEQ ID NO 81
<211> LENGTH: 554
<212> TYPE: PRT
<213> ORGANISM: Artificial sequence
<220> FEATURE:
<223> OTHER INFORMATION: synthesized

<400> SEQUENCE: 81

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
```

```
            195                 200                 205
Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Gly Gly Gly Ser Gly Gly Gly
    530                 535                 540

Ser Gly Gly Gly Ser Cys Lys Thr Cys
545                 550

<210> SEQ ID NO 82
<211> LENGTH: 411
<212> TYPE: PRT
<213> ORGANISM: Artificial sequence
<220> FEATURE:
<223> OTHER INFORMATION: synthesized

<400> SEQUENCE: 82

Gly Ala Asp Asp Val Val Asp Ser Ser Lys Ser Phe Val Met Glu Asn
```

```
1               5                   10                  15
Phe Ser Ser Tyr His Gly Thr Lys Pro Gly Tyr Val Asp Ser Ile Gln
                20                  25                  30
Lys Gly Ile Gln Lys Pro Lys Ser Gly Thr Gln Gly Asn Tyr Asp Asp
                35                  40                  45
Asp Trp Lys Glu Phe Tyr Ser Thr Asp Asn Lys Tyr Asp Ala Ala Gly
        50                  55                  60
Tyr Ser Val Asp Asn Glu Asn Pro Leu Ser Gly Lys Ala Gly Gly Val
65                  70                  75                  80
Val Lys Val Thr Tyr Pro Gly Leu Thr Lys Val Leu Ala Leu Lys Val
                85                  90                  95
Asp Asn Ala Glu Thr Ile Lys Lys Glu Leu Gly Leu Ser Leu Thr Glu
                100                 105                 110
Pro Leu Met Glu Gln Val Gly Thr Glu Glu Phe Ile Lys Arg Phe Gly
                115                 120                 125
Asp Gly Ala Ser Arg Val Val Leu Ser Leu Pro Phe Ala Glu Gly Ser
        130                 135                 140
Ser Ser Val Glu Tyr Ile Asn Asn Trp Glu Gln Ala Lys Ala Leu Ser
145                 150                 155                 160
Val Glu Leu Glu Ile Asn Phe Glu Thr Arg Gly Lys Arg Gly Gln Asp
                165                 170                 175
Ala Met Tyr Glu Tyr Met Ala Gln Ala Cys Ala Gly Asn Arg Val Arg
                180                 185                 190
Arg Ser Val Gly Ser Ser Leu Ser Cys Ile Asn Leu Asp Trp Asp Val
        195                 200                 205
Ile Arg Asp Lys Thr Lys Thr Lys Ile Glu Ser Leu Lys Glu His Gly
        210                 215                 220
Pro Ile Lys Asn Lys Met Ser Glu Ser Pro Asn Lys Thr Val Ser Glu
225                 230                 235                 240
Glu Lys Ala Lys Gln Tyr Leu Glu Glu Phe His Gln Thr Ala Leu Glu
                245                 250                 255
His Pro Glu Leu Ser Glu Leu Lys Thr Val Thr Gly Thr Asn Pro Val
                260                 265                 270
Phe Ala Gly Ala Asn Tyr Ala Ala Trp Ala Val Asn Val Ala Gln Val
                275                 280                 285
Ile Asp Ser Glu Thr Ala Asp Asn Leu Glu Lys Thr Thr Ala Ala Leu
        290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                325                 330                 335
Ser Leu Met Val Ala Gln Ala Ile Pro Leu Val Gly Glu Leu Val Asp
                340                 345                 350
Ile Gly Phe Ala Ala Tyr Asn Phe Val Glu Ser Ile Ile Asn Leu Phe
                355                 360                 365
Gln Val Val His Asn Ser Tyr Asn Arg Pro Ala Tyr Ser Pro Gly His
                370                 375                 380
Lys Thr Gln Pro Phe Gly Gly Gly Ser Gly Gly Gly Ser
385                 390                 395                 400
Gly Gly Gly Ser Gly Pro Cys Lys Thr Cys Thr
                405                 410

<210> SEQ ID NO 83
```

```
<211> LENGTH: 411
<212> TYPE: PRT
<213> ORGANISM: Artificial sequence
<220> FEATURE:
<223> OTHER INFORMATION: synthesized

<400> SEQUENCE: 83
```

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
370                 375                 380

```
Lys Thr Gln Pro Phe Gly Gly Gly Ser Gly Gly Gly Ser Gly
385                 390                 395                 400

Gly Gly Gly Ser Gly Pro Cys Arg Thr Cys Thr
            405                 410
```

<210> SEQ ID NO 84
<211> LENGTH: 419
<212> TYPE: PRT
<213> ORGANISM: Artificial sequence
<220> FEATURE:
<223> OTHER INFORMATION: synthesized

<400> SEQUENCE: 84

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
                35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
                115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
                180                 185                 190

Arg Ser Val Gly Ser Ser Leu Ser Cys Ile Asn Leu Asp Trp Asp Val
                195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
                260                 265                 270

Phe Ala Gly Ala Asn Tyr Ala Ala Trp Ala Val Asn Val Ala Gln Val
                275                 280                 285

Ile Asp Ser Glu Thr Ala Asp Asn Leu Glu Lys Thr Thr Ala Ala Leu
                290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335
```

```
Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Phe Gly Gly Gly Ser Gly Gly Gly Ser Gly
385                 390                 395                 400

Gly Gly Gly Ser Ser Thr Thr Thr Ser Thr Gly Pro Cys Lys Thr Cys
                405                 410                 415

Thr Thr Pro
```

<210> SEQ ID NO 85
<211> LENGTH: 415
<212> TYPE: PRT
<213> ORGANISM: Artificial sequence
<220> FEATURE:
<223> OTHER INFORMATION: synthesized

<400> SEQUENCE: 85

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
            85                  90                  95

Asp Asn Ala Glu Thr Ile Lys Lys Glu Leu Gly Leu Ser Leu Thr Glu
        100                 105                 110

Pro Leu Met Glu Gln Val Gly Thr Glu Glu Phe Ile Lys Arg Phe Gly
    115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
    195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270
```

```
Phe Ala Gly Ala Asn Tyr Ala Ala Trp Ala Val Asn Val Ala Gln Val
                275                 280                 285

Ile Asp Ser Glu Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
        370                 375                 380

Lys Thr Gln Pro Phe Gly Gly Gly Ser Gly Gly Gly Ser Gly
385                 390                 395                 400

Gly Gly Gly Ser Thr Thr Ser Thr Gly Pro Cys Lys Thr Cys Thr
                405                 410                 415

<210> SEQ ID NO 86
<211> LENGTH: 413
<212> TYPE: PRT
<213> ORGANISM: Artificial sequence
<220> FEATURE:
<223> OTHER INFORMATION: synthesized

<400> SEQUENCE: 86

Gly Ala Asp Asp Val Val Asp Ser Ser Lys Ser Phe Val Met Glu Asn
1               5                   10                  15

Phe Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
                35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Val Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
                195                 200                 205

Ile Arg Asp Lys Thr Lys Thr Lys Ile Glu Ser Leu Lys Glu His Gly
        210                 215                 220
```

```
Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
    275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
        340                 345                 350

Ile Gly Phe Ala Ala Tyr Asn Phe Val Glu Ser Ile Ile Asn Leu Phe
    355                 360                 365

Gln Val Val His Asn Ser Tyr Asn Arg Pro Ala Tyr Ser Pro Gly His
370                 375                 380

Lys Thr Gln Pro Phe Gly Gly Gly Ser Gly Gly Gly Ser Gly
385                 390                 395                 400

Gly Gly Gly Ser Cys Lys Thr Cys Thr Thr Pro Ala Gln
                405                 410
```

```
<210> SEQ ID NO 87
<211> LENGTH: 427
<212> TYPE: PRT
<213> ORGANISM: Artificial sequence
<220> FEATURE:
<223> OTHER INFORMATION: synthesized

<400> SEQUENCE: 87

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

Ala Met Tyr Glu Tyr Met Ala Gln Ala Cys Ala Gly Asn Arg Val Arg
                180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
370                 375                 380

Lys Thr Gln Pro Phe Gly Gly Gly Ser Gly Gly Gly Ser Gly
385                 390                 395                 400

Gly Gly Gly Ser Ser Ser Thr Ser Thr Gly Pro Cys Lys Thr Cys
                405                 410                 415

Thr Thr Pro Ala Gln Gly Thr Ser Met Phe Pro
            420                 425

<210> SEQ ID NO 88
<211> LENGTH: 442
<212> TYPE: PRT
<213> ORGANISM: Artificial sequence
<220> FEATURE:
<223> OTHER INFORMATION: synthesized

<400> SEQUENCE: 88

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Phe Ile Lys Arg Phe Gly
            115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
370                 375                 380

Lys Thr Gln Pro Phe Gly Gly Gly Ser Gly Gly Gly Ser Gly
385                 390                 395                 400

Gly Gly Gly Ser Pro Gly Ser Ser Thr Thr Ser Thr Gly Pro Cys Lys
                405                 410                 415

Thr Cys Thr Thr Pro Ala Gln Gly Thr Ser Met Phe Pro Ser Cys Cys
            420                 425                 430

Cys Thr Lys Pro Thr Asp Gly Asn Cys Thr
        435                 440

<210> SEQ ID NO 89
<211> LENGTH: 408
<212> TYPE: PRT
<213> ORGANISM: Artificial sequence
<220> FEATURE:
<223> OTHER INFORMATION: synthesized

<400> SEQUENCE: 89

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

-continued

```
Lys Gly Ile Gln Lys Pro Lys Ser Gly Thr Gln Gly Asn Tyr Asp Asp
             35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Val Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Phe Ile Lys Arg Phe Gly
            115                 120                 125

Asp Gly Ala Ser Arg Val Val Leu Ser Leu Pro Phe Ala Glu Gly Ser
            130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
    370                 375                 380

Lys Thr Gln Pro Phe Gly Gly Gly Ser Gly Gly Gly Ser Gly
385                 390                 395                 400

Gly Gly Gly Ser Cys Lys Thr Cys
                405
```

<210> SEQ ID NO 90
<211> LENGTH: 212
<212> TYPE: PRT
<213> ORGANISM: Artificial sequence
<220> FEATURE:
<223> OTHER INFORMATION: synthesized

<400> SEQUENCE: 90

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Gly Ser Gly Gly Gly Gly Ser Gly Pro Cys
        195                 200                 205

Lys Thr Cys Thr
        210

<210> SEQ ID NO 91
<211> LENGTH: 212
<212> TYPE: PRT
<213> ORGANISM: Artificial sequence
<220> FEATURE:
<223> OTHER INFORMATION: synthesized

<400> SEQUENCE: 91

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
            115                 120                 125

```
Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Gly Ser Gly Gly Gly Ser Gly Pro Cys
            195                 200                 205

Arg Thr Cys Thr
    210
```

<210> SEQ ID NO 92
<211> LENGTH: 220
<212> TYPE: PRT
<213> ORGANISM: Artificial sequence
<220> FEATURE:
<223> OTHER INFORMATION: synthesized

<400> SEQUENCE: 92

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
    115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Gly Ser Gly Gly Gly Ser Ser Thr Thr
            195                 200                 205

Thr Ser Thr Gly Pro Cys Lys Thr Cys Thr Thr Pro
    210                 215                 220
```

<210> SEQ ID NO 93
<211> LENGTH: 216
<212> TYPE: PRT
<213> ORGANISM: Artificial sequence
<220> FEATURE:
<223> OTHER INFORMATION: synthesized

<400> SEQUENCE: 93

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Ser Gly Gly Gly Ser Thr Thr Ser
        195                 200                 205

Thr Gly Pro Cys Lys Thr Cys Thr
        210                 215

<210> SEQ ID NO 94
<211> LENGTH: 214
<212> TYPE: PRT
<213> ORGANISM: Artificial sequence
<220> FEATURE:
<223> OTHER INFORMATION: synthesized

<400> SEQUENCE: 94

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Ser Gly Gly Gly Ser Cys Lys Thr
        195                 200                 205

Cys Thr Thr Pro Ala Gln
    210

<210> SEQ ID NO 95
<211> LENGTH: 228
<212> TYPE: PRT
<213> ORGANISM: Artificial sequence
<220> FEATURE:
<223> OTHER INFORMATION: synthesized

<400> SEQUENCE: 95

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Ser Gly Gly Gly Ser Ser Ser Thr
        195                 200                 205

Thr Ser Thr Gly Pro Cys Lys Thr Cys Thr Thr Pro Ala Gln Gly Thr
    210                 215                 220

Ser Met Phe Pro
225

<210> SEQ ID NO 96
<211> LENGTH: 243
<212> TYPE: PRT
<213> ORGANISM: Artificial sequence
<220> FEATURE:
<223> OTHER INFORMATION: synthesized

```
<400> SEQUENCE: 96

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Gly Gly
            180                 185                 190

Gly Gly Ser Gly Gly Gly Ser Gly Gly Gly Ser Pro Gly Ser
        195                 200                 205

Ser Thr Thr Ser Thr Gly Pro Cys Lys Thr Cys Thr Thr Pro Ala Gln
    210                 215                 220

Gly Thr Ser Met Phe Pro Ser Cys Cys Cys Thr Lys Pro Thr Asp Gly
225                 230                 235                 240

Asn Cys Thr

<210> SEQ ID NO 97
<211> LENGTH: 209
<212> TYPE: PRT
<213> ORGANISM: Artificial sequence
<220> FEATURE:
<223> OTHER INFORMATION: synthesized

<400> SEQUENCE: 97

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110
```

-continued

```
Pro Leu Met Glu Gln Val Gly Thr Glu Glu Phe Ile Lys Arg Phe Gly
        115                 120                 125
Asp Gly Ala Ser Arg Val Val Leu Ser Leu Pro Phe Ala Glu Gly Ser
        130                 135                 140
Ser Ser Val Glu Tyr Ile Asn Asn Trp Glu Gln Ala Lys Ala Leu Ser
145                 150                 155                 160
Val Glu Leu Glu Ile Asn Phe Glu Thr Arg Gly Lys Arg Gly Gln Asp
                165                 170                 175
Ala Met Tyr Glu Tyr Met Ala Gln Ala Cys Ala Gly Asn Arg Gly Gly
            180                 185                 190
Gly Gly Ser Gly Gly Gly Gly Ser Gly Gly Gly Gly Ser Cys Lys Thr
            195                 200                 205
Cys
```

POLYPEPTIDES AND ANTIBODIES FOR TREATING HBV INFECTION AND RELATED DISEASES

CROSS-REFERENCE

This application is a Divisional Application of U.S. patent application Ser. No. 14/406,940, filed Dec. 10, 2014, issued Sep. 5, 2017 as U.S. Pat. No. 9,751,914 which claims priority under 35 U.S.C. § 371 to Patent Cooperation Treaty application PCT/CN2013/076832, filed Jun. 6, 2013, which claims the benefit of Chinese patent application no. 201210190329.X, filed Jun. 11, 2012, the entire contents of which are incorporated herein by reference

SEQUENCE LISTING

This application incorporates in its entirety the Sequence Listing entitled "2015-05-07_235427-366228_SE-Q_LIST_ST25" is 156,291 bytes in size, was created on May 7, 2015 and filed electronically herewith.

TECHNICAL FIELD

The invention relates to the field of molecular virology and immunology, particularly the field concerning the treatment of Hepatitis B virus (HBV) infection. In particular, the invention relates to epitope peptides or (mutants thereof) for treating HBV infection, recombinant proteins comprising said epitope peptides (or mutants thereof) and carrier proteins, and uses of said epitope peptides (or mutants thereof) and said recombinant proteins. The invention also relates to antibodies against said epitope peptides, cell lines for producing said antibodies, and uses thereof. The invention also relates to vaccines or pharmaceutical composition for treating or alleviating one or more symptoms associated with HBV infection, comprising the recombinant proteins or antibodies, respectively.

BACKGROUND ART

HBV infection, particularly chronic HBV infection is one of the most important public sanitation problems globally (Dienstag J L. Hepatitis B virus infection. N Engl J Med 2008 Oct. 2; 359(14): 1486-1500). Chronic HBV infection may cause a series of liver diseases such as Chronic hepatitis B (CHB), Liver cirrhosis (LC) and Hepatocellular carcinoma (HCC) (Liaw Y F, Chu C M. Hepatitis B virus infection. Lancet 2009 Feb. 14; 373(9663): 582-592). It is reported that there are about 2 billion persons infected by HBV, and there are about 350 million persons infected with chronic HBV in the whole world now. Among these infected persons, the risk of finally dying of liver diseases associated with HBV infection reaches up to 15%-25%, and more than 1 million persons die of these diseases every year in the whole world (Dienstag J L., vide supra; and Liaw Y F et al., vide supra).

The therapeutic agents for chronic HBV infection now may be divided mainly into Interferons (IFNs) and nucleoside or nucleotide analogues (NAs) (Dienstag J L., vide supra; Kwon H, Lok A S. Hepatitis B therapy. Nat Rev Gastroenterol Hepatol 2011 May; 8(5): 275-284; and Liaw Y F et al., vide supra). The former includes common interferon (IFN) and Peg-interferon (Peg-IFN), which achieve the effect of inhibiting HBV and treating CHB mainly by enhancing the overall immunocompetennce in patients; the latter mainly includes lamivudine (LMV), adefovir dipivoxil (ADV), Entecavir (ETV), Telbivudine (LdT) and Tenofovir, which inhibit the HBV replication mainly by directly inhibiting polymerase activity of HBV. For HBV infected persons (e.g, CHB patients), said agents alone or in combination have already effectively inhibited virus replication in vivo, and greatly reduced HBV DNA level; in particular, after such a treatment for 52 weeks or longer, response rate that HBV DNA level was lower than the detection limit (virological response) in patients reached 40-80% (Kwon H et al., vide supra). However, the treatment with said agents alone or in combination cannot completely clear up HBV viruses in infected persons, and the response rate of the negative conversion ratio of HBsAg or HBsAg serological conversion (a marker indicative of complete clearance of HBV viruses in patients) is generally lower than 5% (Kwon H et al., vide supra). Therefore, it is urgent and necessary to develop novel therapeutic methods and agents capable of more effectively clearing up HBV viruses, particularly clearing up HBsAg for HBV infected patients.

It is one of the important research directions in this field to develop new agents for treating chronic HBV infection based on immunological means. Immunotherapy of chronic HBV infection is generally performed in two manners, i.e. passive immunotherapy (corresponding to medicaments in the form of antibodies, etc.) and active immunotherapy (corresponding to medicaments in the form of vaccines, etc.). Passive immunotherapy (with antibody as an example) refers to the process of administering a therapeutic antibody to a HBV infected patient and preventing naïve hepatocytes from HBV infection by virtue of antibody-mediated virus neutralization, or clearing up viruses and infected hepatocytes in vivo by virtue of antibody-mediated immune clearance, thereby achieving a therapeutic effect. Now, Anti-HBs polyclonal antibodies, obtained from serum/plasma of responder immunized with hepatitis B vaccine or rehabilitee of HBV infection, i.e. high-titer hepatitis B immunoglobulin (HBIG), have been widely applied to blockage of mother-infant vertical transmission of HBV, prevention of chronic HBV infected patient from HBV re-infection after liver transplantation, and prevention of people accidently exposed to HBV from infection. However, the therapy concerning direct administration of HBIG to HBV-infected patients (e.g., CHB patients) has no significant therapeutic effect, and HBIG is restricted in many aspects such as relatively few sources of high-titer plasma, high cost, unstable property, and potential security problems. Active immunotherapy refers to the process of administering therapeutic vaccines (including protein vaccines, polypeptide vaccines, nucleic acid vaccines, etc.), stimulating chronic HBV-infected organism to raise cellular immunologic response (CTL effect, etc.) or/and humoral immunologic response (antibodies, etc.) to HBV, thereby achieving the purpose of inhibiting or clearing HBV. Now, there are no agents/vaccines for active immunotherapy that are definitely effective and are useful for treating chronic HBV infection yet.

Therefore, it is urgent and necessary to develop novel therapeutic methods and agents capable of more effectively treating HBV infection for HBV infected patients.

CONTENTS OF INVENTION

Although there are multiple B cell response (antibody response) epitopes on various proteins of HBV virus, an antibody against an arbitrary epitope is not necessarily useful in the treatment of HBV infection. Therefore, the key of developing immunotherapeutic agents/methods effective in treating HBV infection lies in identification of targets (epitopes) capable of inducing effective clearance of viruses and cells infected by viruses in vivo and the obtainment of antibodies against the targets (epitopes).

The invention identifies such targets (epitopes), and therefore provides epitope peptides (or mutants thereof) useful in treatment of HBV infection, recombinant proteins comprising said epitope peptides (or mutants thereof) and carrier proteins, and uses of said epitope peptides (or mutants thereof) and recombinant proteins. The invention also provides antibodies against such epitope peptides/epitopes, cell lines producing said antibodies, and uses thereof. The invention also provides vaccines or pharmaceutical compositions useful in treating or relieving one or more symptoms associated with HBV infection, comprising recombinant proteins or antibodies according to the invention, respectively.

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "HBsAg" refers to surface antigen protein of hepatitis B virus (HBV), which is well known by a person skilled in the art (see, for example, NCBI GENBANK Database accession number: AAF24729.1).

As used herein, when the amino acid sequence of HBsAg is mentioned, it is described by the sequence set forth in SEQ ID NO: 39. For example, the expression "amino acid residues from positions 119 to 125 of HBsAg" refers to the amino acid residues from positions 119 to 125 of the polypeptide set forth in SEQ ID NO: 39. However, a person skilled in the art understands that mutations or variations (including, but not limited to, substitution, deletion and/or addition, for example, HBsAg of a different genotype or a different gene subtype) may occur naturally in or be introduced artificially into the amino acid sequence of HBsAg without affecting its biological properties. Therefore, in the invention, the term "HBsAg" intends to comprise all such polypeptides, for example, including the polypeptide set forth in SEQ ID NO: 39 and its natural or artificial mutants. In addition, when sequence fragments of HBsAg are described, they include not only the sequence fragments of SEQ ID NO: 39, but also the corresponding sequence fragments of its natural or artificial mutants. For example, the expression "amino acid residues from positions 119 to 125 of HBsAg" comprises amino acid residues from positions 119 to 125 of SEQ ID NO: 39 and the corresponding fragments of its mutants (natural or artificial mutants). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

As used herein, the term "HBcAg" refers to core antigen protein of hepatitis B virus (HBV), which is well known by a person skilled in the art (see, for example, NCBI GENBANK Database Accession No: AAO63517.1).

As used herein, when the amino acid sequence of HBcAg is mentioned, it is described by the sequence set forth in SEQ ID NO: 40. For example, the expression "amino acid residues from positions 79 to 81 of HBcAg" refers to the amino acid residues from positions 79 to 81 of the polypeptide set forth in SEQ ID NO: 40. However, a person skilled in the art understands that mutations or variations (including, but not limited to, substitution, deletion and/or addition, for example, HBcAg of a different genotype or a different gene subtype) may occur naturally in or be introduced artificially into the amino acid sequence of HBcAg without affecting its biological properties. Therefore, in the invention, the term "HBcAg" intends to comprise all such polypeptides, for example, including the polypeptide set forth in SEQ ID NO: 40 and its natural or artificial mutants. In addition, when sequence fragments of HBcAg are described, they include not only the sequence fragments of SEQ ID NO: 40, but also the corresponding sequence fragments of its natural or artificial mutants. For example, the expression "amino acid residues from positions 79 to 81 of HBcAg" comprises amino acid residues from positions 79 to 81 of SEQ ID NO: 40 and the corresponding fragments of its mutants (natural or artificial mutants). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

As used herein, the term "WHcAg" refers to woodchuck hepatitis virus core antigen, which is well known by a person skilled in the art (see, for example, NCBI GENBANK Database accession number: ADE19018.1).

As used herein, when the amino acid sequence of WHcAg is mentioned, it is described by the sequence set forth in SEQ ID NO: 41. For example, the expression "amino acid residues from positions 79 to 81 of WHcAg" refers to the amino acid residues from positions 79 to 81 of the polypeptide set forth in SEQ ID NO: 41. However, a person skilled in the art understands that mutations or variations (including, but not limited to, substitution, deletion and/or addition, for example, WHcAg of a different genotype or a different gene subtype) may occur naturally in or be introduced artificially into the amino acid sequence of WHcAg without affecting its biological properties. Therefore, in the invention, the term "WHcAg" intends to comprise all such polypeptides, for example, including the polypeptide set forth in SEQ ID NO: 41 and its natural or artificial mutants. In addition, when sequence fragments of WHcAg are described, they include not only the sequence fragments of SEQ ID NO: 41, but also the corresponding sequence fragments of its natural or artificial mutants. For example, the expression "amino acid residues from positions 79 to 81 of WHcAg" comprises amino acid residues from positions 79 to 81 of SEQ ID NO: 41 and the corresponding fragments of its mutants (natural or artificial mutants). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

As used herein, the term "CRM197 (Cross-Reacting Materials 197)" refers to a non-toxic mutant of diphtheria toxin (DT), which differs from a wild-type diphtheria toxin by an amino acid residue at position 52, which is changed from Gly to Glu (G. Giannini, R. Rappuoli, G. Ratti et al., Nucleic Acids Research. 1984. 12: 4063-4070). Diphtheria toxin is well known by a person skilled in the art (see, e.g., Choe S, Bennett M, Fujii G, et al., Nature. 1992. 357:216-222), the amino acid sequence of which may be found, for example, by reference to GenBank Database accession No. AAV70486.1.

As used herein, when the amino acid sequence of CRM197 is mentioned, it is described by the sequence set forth in SEQ ID NO: 42. For example, the expression "amino acid residues from positions 1 to 190 of CRM197" refers to the amino acid residues from positions 1 to 190 of SEQ ID NO: 42. However, a person skilled in the art understands that mutations or variations (including, but not limited to, substitution, deletion and/or addition) may occur naturally in or be introduced artificially into SEQ ID NO: 42 without affecting the biological properties of CRM197. Therefore, in the invention, the term "CRM197" intends to comprise all such polypeptides, for example, including the polypeptide set forth in SEQ ID NO: 42 and its natural or artificial mutants. In addition, when sequence fragments of CRM197 are described, they include not only the sequence fragments of SEQ ID NO: 42, but also the corresponding sequence fragments of its natural or artificial mutants. For example, the expression "amino acid residues from positions 1 to 190 of CRM197" comprises amino acid residues from positions 1 to 190 of SEQ ID NO: 42 and the corresponding fragments of its mutants (natural or artificial). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

As used herein, the term "antibody" generally refers to an immunoglobulin molecule consisting of two pairs of polypeptide chains (each has a light (L) chain and a heavy (H) chain). Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). A light chain constant region consists of a domain $C_L$. The constant region of an antibody can mediate the binding of an immunoglobulin to a host tissue or factor, including various cells (e.g., effector cells) of an immune system and a first component (C1q) of classical complement system. $V_H$ and $V_L$ region can also be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. The term "antibody" is not restricted by any specific method for producing antibodies. For example, antibodies include particularly, recombinant antibodies, monoclonal antibodies and polyclonal antibodies. Antibodies may be of different antibody isotypes, for example, IgG (e.g., IgG1, IgG2, IgG3 or IgG4 subtype), IgA1, IgA2, IgD, IgE or IgM antibody.

As used herein, the term "antigen binding fragment" refers to polypeptides comprising fragments of a full-length antibody, which retain the ability of specifically binding to an antigen that the full-length antibody specifically binds to, and/or compete with the full-length antibody for binding to the same antigen, also known as "antigen binding portion". Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')$_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides.

As used herein, the term "Fd fragment" refers to antibody fragment consisting of $V_H$ and $C_H1$ domain; the term "Fv fragment" refers to antibody fragment consisting of $V_L$ and $V_H$ domain of a single arm; the term "dAb fragment" refers to antibody fragment consisting of $V_H$ domain (Ward et al., Nature 341:544-546 (1989)); the term "Fab fragment" refers to antibody fragment consisting of $V_L$, $V_H$, $C_L$ and $C_H1$ domain; the term "F(ab')$_2$ fragment" refers to antibody fragment comprising two Fab fragments linked to each other via disulfide bridge(s) on hinge region.

Under some conditions, antigen binding fragments of an antibody are single chain antibodies (e.g. scFv), wherein $V_L$ and $V_H$ domain are paired to form a monovalent molecule via a linker that enables them to produce a single polypeptide chain (see, for example, Bird et al., Science 242:423-426 (1988) and Huston et al., Proc. Natl. Acad. Sci. USA 85:5879-5883 (1988)). Such scFv molecules generally have a common structure: $NH_2$—$V_L$-linker-$V_H$—COOH or $NH_2$—$V_H$-linker-$V_L$—COOH. Suitable linkers in the prior art consist of repeated GGGGS amino acid sequence or variants thereof. For example, a linker having an amino acid sequence (GGGGS)$_4$ may be used, and its variants may also be used (Holliger et al., (1993), Proc. Natl. Acad. Sci. USA 90: 6444-6448). Other linkers that may be used in the invention are described by Alfthan et al., (1995), Protein Eng. 8:725-731, Choi et al., (2001), Eur. J. Immunol. 31: 94-106, Hu et al., (1996), Cancer Res. 56:3055-3061, Kipriyanov et al., (1999), J. Mol. Biol. 293:41-56 and Roovers et al., (2001), Cancer Immunol.

Under some conditions, antigen binding fragments of an antibody may be diabodies, i.e. divalent antibodies, wherein $V_H$ and $V_L$ domain are expressed on a single polypeptide chain, however, the linker used is too short to allow the pairing of the two domains on the same chain, the domains have to be paired with the complementary domains on another chain to produce two antigen binding sites (see, for example, Holliger P. et al., Proc. Natl. Acad. Sci. USA 90:6444-6448 (1993), and Poljak R. J. et al., Structure 2:1121-1123 (1994)).

Antigen binding fragments (e.g. the antibody fragments as described above) of an antibody may be obtained from a given antibody (e.g., the monoclonal antibody E6F6 provided in the invention) by conventional techniques known by a person skilled in the art (e.g., recombinant DNA technique or enzymatic or chemical cleavage methods), and may be screened for specificity in the same manner by which inact antibodies are screened.

In the invention, unless specified definitely, when the term "antibody" is mentioned, it includes not only intact antibodies, but also antigen binding fragments of the antibodies.

As used herein, the term "MAb" and "monoclonal antibody" refer to an antibody or a fragment of an antibody from a population of highly homologous antibody molecules, i.e. a population of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. Monoclonal antibodies are generally obtained by hybridoma technique reported by Kohler et al. for the first time (Nature, 256:495, 1975), and can also be obtained by recombinant DNA technique (see, for example, U.S. Pat. No. 4,816,567).

As used herein, monoclonal antibodies mentioned with their numbers are identical to the monoclonal antibodies obtained from the hybridomas with the same numbers. For example, monoclonal antibody HBs-E6F6 (E6F6 for short), HBs-E7G11 (E7G11 for short), HBs-G12F5 (G12F5 for short) and HBs-E13C5 (E13C5 for short) are identical to the antibodies obtained from hybridoma cell line HBs-E6F6 (E6F6 for short) or subclone or progeny cell thereof, HBs-E7G11 (E7G11 for short) or subclone or progeny cell thereof, HBs-G12F5 (G12F5 for short) or subclone or progeny cell thereof, and HBs-E13C5 (E13C5 for short) or subclone or progeny cell thereof, respectively.

As used herein, the term "chimeric antibody" refers to such an antibody wherein a part of its light chain and/or heavy chain is derived from an antibody (which may be originated from a specific species or belongs to a specific antibody type or subtype), and the other part of its light chain and/or heavy chain is derived from another antibody (which may be originated from an identical or different species or belongs to an identical or different antibody type or subtype), provided that the antibody still retains the activity of binding to the antigen of interest (U.S. Pat. No. 4,816,567 to Cabilly et al.; Morrison et al., Proc. Natl. Acad. Sci. USA, 81: 6851-6855 (1984)).

As used herein, the term "humanized antibody" refers to an antibody or antibody fragment in which all the CDR regions or a part of CDR regions of human immunoglobulin (receptor antibody) are replaced with the CDR regions of a non-human antibody (donor antibody), wherein the donor antibody may be non-human (e.g., mouse, rat or rabbit) antibody having the expected specificity, affinity or reactivity. In addition, some amino acids of framework regions (FRs) of a receptor antibody may also be replaced by the corresponding amino acid residues of a non-human antibody, or amino acid residues of another antibody, so as to further improve or optimize the properties of the antibody. With respect to more detailed contents relating to humanized antibodies, please see, for example, Jones et al., Nature, 321:522-525 (1986); Reichmann et al., Nature, 332:323-329 (1988); Presta, Curr. Op. Struct. Biol., 2:593-596 (1992); and Clark, Immunol. Today 21: 397-402 (2000).

As used herein, the term "neutralization antibody" refers to an antibody or antibody fragment that can eliminate or significantly reduce virulence (e.g. ability of infecting cells) of viruses of interest.

As used herein, the term "epitope" refers to a portion on antigen that an immunoglobulin or antibody specifically binds to. "Epitope" is also known as "antigenic determinant". Eptiope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein.

As used herein, the term "epitope peptide" refers to peptide fragment on antigen that acts as epitope. Under some conditions, epitope peptide alone can be specifically recognized/bound by an antibody against the epitope. Under some other conditions, epitope peptide has to be fused to a carrier protein to facilitate the epitope to be specifically recognized by an antibody. As used herein, the term "carrier protein" refers to such a protein that may act as a carrier of epitope peptide, i.e. the epitope peptide may be inserted into the protein at a specific position (for example, inner, N-terminal or C-terminal of the protein), so that the epitope peptide can be presented and thus can be recognized by an antibody or immune system. Such carrier proteins are well known by a person skilled in the art, including, for example, HPV L1 protein (into which the epitope peptide may be inserted between amino acids from positions 130 to 131 or amino acids from positions 426 to 427 of the protein, see Slupetzky, K. et al., Chimeric papillomavirus-like particles expressing a foreign epitope on capsid surface loops[J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16[J]. J Virol, 2003, 77: 8386-8393), HBV core antigen (the amino acids from positions 79 to 81 of the protein may be replaced with the epitope peptide, see, Koletzki, D., et al. HBV core particles allow the insertion and surface exposure of the entire potentially protective region of Puumala hantavirus nucleocapsid protein [J]. Biol Chem, 1999, 380: 325-333), woodchuck hepatitis virus core protein (the amino acids from positions 79 to 81 of the protein may be replaced with the epitope peptide, see, Sabine Konig, Gertrud Beterams and Michael Nassal, J. Virol. 1998, 72(6):4997), and CRM197 protein (the epitope peptide may be linked to the N-terminal or C-terminal of the protein or a fragment thereof). Optionally, a linker (e.g., a rigid or flexible linker) may be used between an epitope peptide and a carrier protein to promote their foldings, respectively.

Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. HBsAg protein). High-throughput methods for obtaining antibodies binding to the same epitope, which are based on their cross-competition, are described in an international patent application WO 03/48731. Therefore, antibodies and antigen binding fragments (i.e. antigen binding portions) thereof, which compete with monoclonal antibodies according to the invention (e.g. monoclonal antibody E6F6) for binding to the same epitopes on HBsAg protein, can be obtained by conventional techniques known by a person skilled in the art.

As used herein, the term "isolated" refers to a state obtained from natural state by artificial means. If a certain "isolated" substance or component is present in nature, it is possible because its natural environment changes, or the substance is isolated from natural environment, or both. For example, a certain unisolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other unpure substances that do not affect the activity of the isolated substance.

As used herein, the term "E. coli expression system" refers to an expression system consisting of E. coli (strain) and a vector, wherein the E. coli (strain) are derived from the commercially available strains, including, but not limited to: GI698, ER2566, BL21 (DE3), B834 (DE3), and BLR (DE3).

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovius, adeno-associated virus, herpes virus (such as herpes simplex virus), pox virus, baculovirus, papillomavirus, papova virus (such as SV40). A vector may comprises multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, prokaryotic cell such as E. coli or Bacillus subtilis, and fungal cell such as yeast cell or Aspergillus, insect cell such as S2 Drosophila cell or Sf9, or animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

As used herein, the term "immunogenicity" refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

As used herein, the term "specifically bind" refers to the binding of two molecules in a non-random manner, such as the reaction between an antibody and the antigen it directs to. In some embodiments, an antibody that specifically binds to an antigen (or an antibody specific for an antigen) refers to an antibody that binds to the antigen with an affinity ($K_D$) of less than about $10^{-5}$ M, e.g. of less than about $10^{-6}$ M, $10^{-7}$ M, $10^{-8}$ M, $10^{-9}$ M or $10^{-10}$ M or less.

As used herein, the term "$K_D$" refers to a dissociation constant of a specific antibody-antigen interaction, which is used to describe the binding affinity of an antibody to an antigen. Generally, an antibody (e.g., the monoclonal antibody E6F6 according to the invention) binds to an antigen (e.g., HBsAg) with a $K_D$ of less than about $10^{-5}$ M, e.g., less than about $10^{-6}$ M, $10^{-7}$ M, $10^{-8}$ M, $10^{-9}$ M or $10^{-10}$ M or less, determined by, for example, surface plasmon resonance (SPR) in BIACORE device.

As used herein, the term "monoclonal antibody" and the term "MAb" have the same meanings and are used interchangeably; the term "polyclonal antibody" and the term "PAb" have the same meanings and are used interchangeably; the term "polypeptide" and "protein" have the same meanings and are used interchangeably. Moreover, in the invention, amino acids are represented by single letter codes or three letter codes. For example, alanine may be represented by A or Ala.

As used herein, the term "hybridoma" and the term "hybridoma cell line" may be used interchangeably. When the term "hybridoma" and the term "hybridoma cell line" are mentioned, they also include subclone and progeny cell of hybridoma. For example, when hybridoma cell line E6F6 is mentioned, it also refers to the subclone and progeny cell of hybridoma cell line E6F6.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium *parvum*, lipopolysaccharide, cytokines, and the like. Freund's adjuvant is the most commonly used adjuvant in animal experiments now. Aluminum hydroxide adjuvant is more commonly used in clinical trials.

As used herein, the term "protein vaccine" refers to a polypeptide-based vaccine, optionally comprising an adjuvant. Polypeptides in vaccines may be obtained by genetic engineering techniques or by methods of chemical synthesis. As used herein, the term "nucleic acid vaccine" refers to a DNA or RNA-based vaccine (such as plasmid, e.g., expression plasmid), optionally comprising an adjuvant.

As used herein, the term "an effective amount" refers to an amount that is sufficient to achieve or at least partially achieve the expected effect. For example, an amount effective for preventing a disease (such as HBV infection or diseases associated with HBV infection) refers to an amount effective for preventing, suppressing, or delaying the occurrence of a disease (such as HBV infection or diseases associated with HBV infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

As used herein, the biological function of the epitope peptide according to the invention includes, but is not limited to one or more of:

1) specific binding to antibody E6F6, E7G11, G12F5 or E13C5;
2) ability of reducing serum level of HBV DNA and/or HBsAg in a subject (optionally, after fusing the epitope peptide to the carrier protein);
3) ability of inducing an antibody response of effective clearance of HBV and HBV-infected cells in vivo (optionally, after fusing the epitope peptide to the carrier protein); and
4) ability of treating HBV infection or diseases associated with HBV infection (e.g., hepatitis B) in a subject (optionally, after fusing the epitope peptide to the carrier protein).

Therefore, in one aspect, the invention provides an isolated epitope peptide consisting of amino acid residues from positions 119-125 of HBsAg protein, or a mutant thereof, wherein the mutant differs from the epitope peptide merely by conservative substitution of one or several (e.g., 1, 2, 3 or 4) amino acid residues and retains the biological function of the epitope peptide. In one preferred embodiment, the amino acid residues from positions 119-125 of HBsAg protein are shown in SEQ ID NO: 1. In one preferred embodiment, the amino acid sequence of the mutant is shown in SEQ ID NO: 2.

In another aspect, the invention provides an isolated epitope peptide consisting of amino acid residues from positions 113-135 of HBsAg protein, or a mutant thereof, wherein the mutant differs from the epitope peptide merely by conservative substitution of one or several (e.g., 1, 2, 3, 4, 5, 6, 7, 8 or 9) amino acid residues and retains the biological function of the epitope peptide. In one preferred embodiment, the amino acid residues from positions 113-135 of HBsAg protein are shown in SEQ ID NO: 6.

In another aspect, the invention provides an isolated epitope peptide consisting of 4-38 consecutive amino acid residues of HBsAg protein and comprising amino acid residues from positions 121-124 of HBsAg protein, or a mutant thereof, wherein the mutant differs from the epitope peptide merely by conservative substitution of one or several (e.g., 1, 2, 3, 4, 5, 6, 7, 8 or 9) amino acid residues and retains the biological function of the epitope peptide. In one preferred embodiment, the amino acid residues from positions 121-124 of HBsAg protein are shown in SEQ ID NO: 10.

In one preferred embodiment, the epitope peptide according to the invention consists of no more than 38, e.g., 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5 or 4 consecutive amino acid residues of HBsAg protein. For example, the epitope peptide or the mutant thereof according to the invention has an amino acid sequence selected from a group consisting of SEQ ID NO: 1-7 and 10.

Particularly, the epitope peptide or mutant thereof according to the invention may be fused to a carrier protein to enhance the immunogenicity of the epitope peptide or mutant thereof so that the epitope peptide or mutant thereof can be recognized by immune system in organisms and induce an antibody response of effective clearance of viruses and virus-infected cells in vivo.

Therefore, in one aspect, the invention also provides a recombinant protein comprising the isolated epitope peptide or mutant thereof according to the invention, and a carrier protein, wherein the recombinant protein is not a naturally occurring protein or a fragment thereof. In the recombinant protein, the epitope peptide or mutant thereof may be linked to the N-terminus or C-terminus of the carrier protein, be inserted into the carrier protein, or be used to replace a portion of the amino acid sequence of the carrier protein, depending on the carrier protein used. In addition, optionally, the epitope peptide or mutant thereof may be linked to the carrier protein via a linker (a rigid or flexible linker, e.g., $(GGGGS)_3$). The recombinant protein of the invention may be produced by any method, for example, by genetic engineering method (recombinant technique), or by method of chemical synthesis.

In one preferred embodiment, said carrier protein is selected from a group consisting of CRM197 protein or a fragment thereof, HBcAg and WHcAg.

In one preferred embodiment, the carrier protein is CRM197 protein or a fragment thereof, and the epitope peptide or mutant thereof according to the invention is linked to the N-terminus or C-terminus of CRM197 protein or a fragment thereof, optionally via a linker. In one preferred embodiment, the fragment of the CRM197 protein comprises aa 1-190 (aa represents amino acid; when aa is placed before n, it indicates the amino acid at position n (for example, aa 1-190 represents amino acids at positions 1-190); when aa is placed after n, it indicates that a polypeptide has a length of n amino acids (the same below)) of CRM197, e.g., comprising aa 1-389 of CRM197. In another preferred embodiment, the fragment of the CRM197 protein consists of aa 1-190 or aa 1-389 of CRM197 (which is designated as CRM A and CRM 389 in the invention, respectively).

In one preferred embodiment, the amino acid sequence of the linker is set forth in SEQ ID NO: 46. In one preferred embodiment, the recombinant protein according to the invention has an amino acid sequence selected from a group consisting of SEQ ID NO: 74-97.

In one preferred embodiment, the carrier protein is HBcAg or a fragment thereof, and the amino acids from positions 79 to 81 of HBcAg are replaced with the epitope peptide according to the invention. In one preferred embodiment, the epitope peptide is linked to HBcAg or a fragment thereof via a linker. In one preferred embodiment, the fragment of HBcAg comprises or consists of aa 1-149 of HBcAg. In one preferred embodiment, the recombinant protein according to the invention has an amino acid sequence selected from a group consisting of SEQ ID NO: 47-53, 56, and 58-65.

In one preferred embodiment, the carrier protein is WHcAg or a fragment thereof, and the amino acids from positions 79 to 81 of WHcAg are replaced with the epitope peptide according to the invention. In one preferred embodiment, the epitope peptide is linked to WHcAg or a fragment thereof via a linker. In one preferred embodiment, the fragment of WHcAg comprises or consists of aa 1-149 of WHcAg. In one preferred embodiment, the recombinant protein according to the invention has an amino acid sequence selected from a group consisting of SEQ ID NO: 66-73.

In another aspect, the invention also provides an isolated nucleic acid molecule, comprising a nucleotide sequence encoding the epitope peptide or mutant thereof according to the invention or the recombinant protein according to the invention. In another aspect, the invention also provides a vector, comprising said isolated nucleic acid molecule. The vector according to the invention may be a cloning vector, or an expression vector. In one preferred embodiment, the vector according to the invention may be, for example, plasmid, cosmid, phage, and the like. In one preferred embodiment, the vector can express the epitope peptide or mutant thereof according to the invention or the recombinant protein according to the invention in a subject (for example, mammalian, e.g. human).

In another aspect, the invention also provides a host cell comprising the isolated nucleic acid molecule or vector according to the invention. Such host cells include, but are not limited to, prokaryotic cell such as E. coli cell, and eukaryotic cell such as yeast cell, insect cell, plant cell and animal cell (such as mammalian cell, e.g., mouse cell, human cell, etc.). The cell according to the invention may be a cell line, such as 293T cell.

In another aspect, the invention also provides a method for preparing the recombinant protein according to the invention, comprising culturing the host cell according to the invention under suitable conditions, and recovering the recombinant protein according to the invention from the cell culture.

In another aspect, the invention provides a protein vaccine, comprising the epitope peptide (or mutant thereof) or the recombinant protein according to the invention, and a pharmaceutically acceptable carrier and/or excipient (e.g., adjuvant). In one preferred embodiment, the protein vaccine comprises one or more epitope peptides according to the invention, wherein said epitope peptides may be separate or tandem, modified or unmodified, coupled to another protein or not.

In another aspect, the invention provides a method for treating HBV infection or diseases associated with HBV infection (e.g., hepatitis B) in a subject, comprising administering a therapeutically effective amount of the epitope peptide (or mutant thereof), the recombinant protein or the protein vaccine according to the invention to a subject in need thereof.

In another aspect, the invention provides use of the epitope peptide (or mutant thereof) or the recombinant protein according to the invention in manufacture of a protein vaccine for treating HBV infection or diseases associated with HBV infection (e.g., hepatitis B) in a subject.

In another aspect, the invention provides the epitope peptide (or mutant thereof) or the recombinant protein according to the invention for treating HBV infection or diseases associated with HBV infection (e.g., hepatitis B) in a subject.

In another aspect, the invention provides a gene vaccine comprising the isolated nucleic acid molecule or the vector according to the invention, and a pharmaceutically acceptable carrier and/or excipient (e.g., adjuvant). In one preferred embodiment, the gene vaccine comprises DNA or RNA. In such embodiments, the DNA or RNA may be naked or encapsulated into a shell having a delivery and/or protective function. In one further preferred embodiment, the shell may be the shell of adenovius, adeno-associated virus, lentivirus, retrovirus, etc., or may be another material that is synthesized by chemical methods and is capable of exerting a similar function.

In another aspect, the invention provides a method for treating HBV infection or diseases associated with HBV infection (e.g., hepatitis B) in a subject, comprising administering a therapeutically effective amount of the gene vaccine or isolated nucleic acid molecule or vector according to the invention to a subject in need thereof.

In another aspect, the invention provides use of the isolated nucleic acid molecule or vector according to the invention in manufacture of a gene vaccine for treating HBV infection or diseases associated with HBV infection (e.g., hepatitis B) in a subject.

In another aspect, the invention provides the isolated nucleic acid molecule or vector according to the invention for treating HBV infection or diseases associated with HBV infection (e.g., hepatitis B) in a subject.

In another aspect, the invention provides a pharmaceutical composition, comprising the epitope peptide (or mutant thereof), recombinant protein, isolated nucleic acid molecule, or vector according to the invention, and a pharmaceutically acceptable carrier and/or excipient (e.g., adjuvant). In one preferred embodiment, the pharmaceutical composition comprises one or more epitope peptides according to the invention, wherein the epitope peptides may be separate or tandem, modified or unmodified, coupled to another protein or not.

In another aspect, the invention provides a method for reducing serum level of HBV DNA and/or HBsAg in a subject, comprising administering an effective amount of the pharmaceutical composition, epitope peptide (or mutant thereof), recombinant protein, isolated nucleic acid molecule, or vector according to the invention to a subject in need thereof.

In another aspect, the invention provides use of the epitope peptide (or mutant thereof), recombinant protein, isolated nucleic acid molecule, or vector according to the invention in manufacture of a pharmaceutical composition for reducing serum level of HBV DNA and/or HBsAg in a subject.

In another aspect, the invention provides the epitope peptide (or mutant thereof), recombinant protein, isolated nucleic acid molecule, or vector according to the invention, for reducing serum level of HBV DNA and/or HBsAg in a subject.

In one aspect, the invention provides a monoclonal antibody and an antigen binding fragment thereof, wherein the monoclonal antibody can specifically bind to the epitope peptide according to the invention.

In one preferred embodiment, the monoclonal antibody or antigen binding fragment thereof is selected from a group consisting of Fab, Fab', F(ab')$_2$, Fd, Fv, dAb, complementary determining region fragment, single chain antibody (e.g., scFv), mouse antibody, rabbit antibody, humanized antibody, full-human antibody, chimeric antibody (e.g., human mouse chimeric antibody), or bispecific or poly-specific antibody.

In one preferred embodiment, the monoclonal antibody binds to the epitope peptide according to the invention or HBsAg protein with a $K_D$ of less than about $10^{-5}$ M, for example, less than about $10^{-6}$ M, $10^{-7}$ M, $10^{-8}$ M, $10^{-8}$ M or $10^{-10}$ M or less.

In one preferred embodiment, the monoclonal antibody comprises non-CDR region, and the non-CDR region is from species other than murine species, e.g., is from human antibody.

In one preferred embodiment, the monoclonal antibody can reduce serum level of HBV DNA and/or HBsAg in a subject.

In one preferred embodiment, the monoclonal antibody is derived from the following monoclonal antibodies or is selected from the following antibodies:
1) the monoclonal antibody produced by the hybridoma cell line HBs-E6F6, wherein the hybridoma cell line HBs-E6F6 is deposited in China Center for Type Culture Collection (CCTCC), with a deposition number of CCTCC NO. C201270;
2) the monoclonal antibody produced by the hybridoma cell line HBs-E7G11, wherein hybridoma cell line HBs-E7G11 is deposited in China Center for Type Culture Collection (CCTCC), with a deposition number of CCTCC NO. C201271;
3) the monoclonal antibody produced by the hybridoma cell line HBs-G12F5, wherein the hybridoma cell line HBs-G12F5 is deposited in China Center for Type Culture Collection (CCTCC), with a deposition number of CCTCC NO. C201272; and
4) the monoclonal antibody produced by the hybridoma cell line HBs-E13C5, wherein the hybridoma cell line HBs-E13C5 is deposited in China Center for Type Culture Collection (CCTCC), with a deposition number of CCTCC NO. C201273.

In another aspect, the invention provides a monoclonal antibody and an antigen binding fragment thereof, capable of blocking the binding of the epitope peptide according to the invention or HBsAg protein to the antibody produced by the hybridoma cell line HBs-E6F6, HBs-E7G11, HBs-G12F5 or HBs-E13C5 by at least 50%, preferably at least 60%, preferably at least 70%, preferably at least 80%, preferably at least 90%, preferably at least 95% or preferably at least 99%, wherein the hybridoma cell line HBs-E6F6, HBs-E7G11, HBs-G12F5 and HBs-E13C5 are deposited in China Center for Type Culture Collection (CCTCC), with a deposition number of CCTCC NO. C201270, CCTCC NO. C201271, CCTCC NO. C201272 and CCTCC NO. C201273, respectively.

The epitopes recognized by such monoclonal antibodies are identical to, or overlap spatially with the epitopes recognized by monoclonal antibody E6F6, E7G11, G12F5 or E13C5, so that such monoclonal antibodies can reduce the binding of monoclonal antibody E6F6, E7G11, G12F5 or E13C5 to the epitope peptide according to the invention or HBsAg protein by at least 50%, preferably at least 60%, preferably at least 70%, preferably at least 80%, preferably at least 90%, preferably at least 95% or preferably at least 99%.

The ability of a monoclonal antibody to be tested to reduce the binding of a known monoclonal antibody to HBsAg protein can be determined by conventional methods, such as the methods described in Antibodies: A Laboratory Manual, Cold Spring Harbor Laboratory, Ed Harlow and David Lane (1988). One exemplary method comprises: pre-coating an antigen to a microwell plate, adding a series of diluted unlabelled antibodies to be tested together with a given concentration of a known labeled monoclonal antibody to the pre-coated microwell plate and conducing incubation, and then determining the number of the known antibodies bound to the plate in the presence of the differently diluted antibody to be tested, after washing. The stronger the ability of an antibody to be tested to compete with a known antibody for binding to an antigen that the known antibody binds to is, the weaker the ability of the known antibody to bind to the antigen is, and the less the known antibodies that are bound to the plate are. Generally, antigens are coated on a 96-well microwell plate, and a monoclonal antibody to be tested may be tested for its ability of blocking a known labeled monoclonal antibody by radioactive labelling method or enzyme labelling method.

Monoclonal antibodies may be prepared by methods for preparing hybridomas reported by Kohler et al. (Nature 256: 495 (1975)). Firstly, mice or other suitable host animals are immunized by injection of immunogen (if necessary, adjuvants are added). The injection means of immunogens or adjuvants generally are subcutaneous multi-point injection or intraperitoneal injection. Pre-conjugation of immunogens to some known proteins (e.g. serum albumin) may promote immunogenicity of antigens in a host. Adjuvants may be Freund's adjuvant or MPL-TDM, etc. After immunization of animal, lymphocytes secreting antibodies that specifically bind to immunogen are produced in the animal. Lymphocytes of interest are collected and are fused to myeloma cells using a suitable fusion agent (such as PEG), thereby getting hybridoma cells (Goding, Monoclonal Antibodies: Principles and Practice, pp. 59-103, Academic Press, 1996).

The hybridoma cells prepared above are seeded to a suitable culture medium and grow in the medium, and the culture medium comprises one or more substances capable of inhibiting growth of unfused, parent myeloma cells. For example, in the case of parent myeloma cells deficient in hypoxanthine guanine phosphoribosyl transferase (HGPRT or HPRT), growth of HGPRT-deficient cells is inhibited by the addition of substances such as hypoxanthine, aminopterin and thymine (HAT culture medium) to the culture medium.

Preferred myeloma cells should have a high fusion rate, stable ability of secreting antibodies, be sensitive to HAT culture medium, and the like. The first choice of myeloma cells is murine myeloma, such as MOP-21 and MC-11 mouse tumor derived cell line (THE Salk Institute Cell Distribution Center, San Diego, Calif. USA), and SP-2/0 or X63-Ag8-653 cell line (American Type Culture Collection, Rockville, Md. USA). In addition, human myeloma and human-mouse heterogenous myeloma cell lines may be used to prepare human monoclonal antibodies (Kozbor, J. Immunol., 133: 3001 (1984); Brodeur et al., Monoclonal Antibody Production Techniques and Applications, pp. 51-63, Marcel Dekker, Inc., New York, 1987).

Culture media for growing hybridoma cells are used to detect the generation of monoclonal antibodies against specific antigens. The following methods may be used to determine the binding specificity of monoclonal antibodies produced in hybridoma cells, immunoprecipitation or in vitro binding assays, such as Radioimmunoassay (RIA) and enzyme linked immunosorbent assay (ELISA). For example, Scatchard assay described in Munson et al., Anal. Biochem. 107: 220 (1980) may be used to determine the affinity of monoclonal antibodies.

After determining the specificity, affinity and reactivity of antibodies produced in hybridomas, cell lines of interest may be subcloned by limiting dilution method described in Goding, Monoclonal Antibodies: Principles and Practice, pp. 59-103, Academic Press, 1996. A suitable culture medium may be DMEM or RPMI-1640, etc. In addition, hybridoma cells may grow in a form of ascites tumor in animal bodies.

By using traditional methods for purifying immunoglobulins, such as Protein A agarose gel, hydroxyapatite chromatography, gel electrophoresis, dialysis and affinity chromatography, monoclonal antibodies secreted by subclone cells may be isolated from cell culture, ascites or serum.

Monoclonal antibodies may be obtained by genetic engineering recombinant techniques. The nucleic acid primers that specifically bind to MAb heavy chain and light chain gene are subjected to PCR amplification, thereby isolating the DNA molecules encoding MAb heavy chain and light chain from hybridoma cells. The DNA molecules obtained are inserted into an expression vector, host cells (e.g. *E. coli* cells, COS cells, CHO cells, or other myeloma cells that do not produce immunoglobulin) are transfected with them and are cultured under suitable conditions to obtain antibodies of interest by recombinant expression.

The invention also provides an isolated nucleic acid molecule, encoding the monoclonal antibody or antigen binding fragment thereof according to the invention. Such nucleic acid molecules may be isolated from hybridoma cells, or may be obtained by genetic engineering recombinant technique or methods of chemical synthesis.

In one aspect, the invention provides an isolated nucleic acid molecule, comprising a nucleic acid sequence encoding the heavy chain variable region of the monoclonal antibody according to the invention.

In another aspect, the invention provides an isolated nucleic acid molecule, comprising a nucleic acid sequence encoding the light chain variable region of the monoclonal antibody according to the invention.

In another aspect, the invention provides a vector comprising the isolated nucleic acid molecule according to the invention. The vector according to the invention may be a cloning vector, or an expression vector.

In one preferred embodiment, the vector according to the invention is a plasmid, a cosmid, a phage, etc.

In another aspect, the invention also provides a host cell comprising the isolated nucleic acid molecule or vector according to the invention. Such host cells include, but are not limited to, prokaryotic cell such as *E. coli* cell, and eukaryotic cell such as yeast cell, insect cell, plant cell and animal cell (such as mammalian cell, e.g., mouse cell, human cell, etc.). The cell according to the invention may be a cell line, such as 293T cell.

In another aspect, the invention also provides a method for preparing the monoclonal antibody or antigen binding fragment thereof according to the invention, comprising culturing the host cell according to the invention under suitable conditions, and recovering the monoclonal antibody or antigen binding fragment thereof according to the invention from the cell culture.

In another aspect, the invention provides a hybridoma cell line selected from
1) hybridoma cell line HBs-E6F6, deposited in China Center for Type Culture Collection (CCTCC), with a deposition number of CCTCC NO. C201270;
2) hybridoma cell line HBs-E7G11, deposited in China Center for Type Culture Collection (CCTCC), with a deposition number of CCTCC NO. C201271;
3) hybridoma cell line HBs-G12F5, deposited in China Center for Type Culture Collection (CCTCC), with a deposition number of CCTCC NO. C201272; and
4) hybridoma cell line HBs-E13C5, deposited in China Center for Type Culture Collection (CCTCC), with a deposition number of CCTCC NO. C201273.

The amino acid sequences and/or nucleotide sequences of the heavy chain variable region, light chain variable region, heavy chain variable region CDR and light chain variable region CDR comprised in various antibodies can be determined from monoclonal antibody E6F6, E7G11, G12F5 and E13C5 by conventional methods.

In another aspect, the invention provides a kit comprising the monoclonal antibody or antigen binding fragment thereof according to the invention. In one preferred embodiment, the monoclonal antibody or antigen binding fragment thereof according to the invention may also comprise a detectable marker. In one preferred embodiment, the kit further comprises a second antibody that specifically binds to the monoclonal antibody or antigen binding fragment thereof according to the invention. Preferably, the second antibody further comprises a detectable marker. Such detectable markers, which are well known by a person skilled in the art, include, but are not limited to, radioisotope, fluorescent substance, luminescent substance, chromophoric substance and enzyme (e.g., horseradish peroxidase), etc.

In another aspect, the invention provides a method for detecting the presence or level of HBsAg protein in a sample, comprising using the monoclonal antibody or antigen binding fragment thereof according to the invention. In one preferred embodiment, the monoclonal antibody or antigen binding fragment thereof according to the invention further comprises a detectable marker. In another preferred embodiment, the method further comprises using a second antibody carrying a detectable marker to detect the monoclonal antibody or antigen binding fragment thereof according to the invention. The method may be used for diagnostic purpose or for non-diagnostic purpose (for example, said sample is a cell sample, rather than a sample from a patient).

In another aspect, the invention provides a method for diagnosing whether a subject is infected by HBV, comprising using the monoclonal antibody or antigen binding fragment thereof according to the invention to detect the presence of HBsAg protein in a sample from the subject. In one preferred embodiment, the monoclonal antibody or antigen binding fragment thereof according to the invention also comprises a detectable marker. In another preferred embodiment, the method further comprises using a second antibody carrying a detectable marker to detect the monoclonal antibody or antigen binding fragment thereof according to the invention.

In another aspect, the invention provides use of the monoclonal antibody or antigen binding fragment thereof according to the invention in manufacture of a kit for detecting the presence or level of HBsAg in a sample or for diagnosing whether a subject is infected by HBV.

In another aspect, the invention provides a pharmaceutical composition comprising the monoclonal antibody or antigen binding fragment thereof according to the invention, and a pharmaceutically acceptable carrier and/or excipient.

In another aspect, the invention provides a method for preventing or treating HBV infection or diseases associated with HBV infection (e.g., hepatitis B) in a subject, comprising administering a prophylactically or therapeutically effective amount of the monoclonal antibody or antigen binding fragment thereof according to the invention or the pharmaceutical composition according to the invention in a subject in need thereof.

In another aspect, the invention provides use of the monoclonal antibody or antigen binding fragment thereof according to the invention in manufacture of a pharmaceutical composition for preventing or treating HBV infection or diseases associated with HBV infection (e.g., hepatitis B) in a subject.

In another aspect, the invention provides the monoclonal antibody or antigen binding fragment thereof according to the invention for preventing or treating HBV infection or diseases associated with HBV infection (e.g., hepatitis B) in a subject.

In another aspect, the invention provides a method for reducing serum level of HBV DNA and/or HBsAg in a subject, comprising administering an effective amount of the monoclonal antibody or antigen binding fragment thereof according to the invention to a subject in need thereof. In another aspect, the invention provides use of the monoclonal antibody or antigen binding fragment thereof according to the invention in manufacture of a medicament for reducing serum level of HBV DNA and/or HBsAg in a subject.

The vaccine (protein vaccine and gene vaccine), medicament and pharmaceutical composition provided in the invention may be used alone or in combination, or may be used in combination with another pharmaceutically active agent (e.g., interferon agents, such as interferon or pegylated interferon).

Advantageous Effects of the Invention

As compared to the prior art, the epitope peptide according to the invention and the recombinant protein comprising the epitope peptide has significant advantages. Particularly, the epitope peptide and the recombinant protein according to the invention can induce antibody response with respect to effective clearance of HBV and HBV-infected cells, and thereby can reduce serum level of HBV DNA and/or HBsAg in a subject and can be useful in the treatment of HBV infection or diseases associated with HBV infection (e.g., hepatitis B) in a subject.

In addition, the invention also provides monoclonal antibodies and antigen binding fragments thereof that can specifically recognize and/or bind to the epitope peptides according to the invention. Such monoclonal antibodies and antigen binding fragments thereof can reduce serum level of HBV DNA and/or HBsAg in a subject, can effectively clear up HBV and HBV-infected cells in vivo, and therefor are useful in treating HBV infection or diseases associated with HBV infection (e.g., hepatitis B) in a subject.

The epitope peptides according to the invention also have the advantage that monoclonal antibodies and polyclonal antibodies against the epitope peptides can significantly reduce HBsAg level and HBV DNA level in a subject (e.g., HBV transgenic mouse), and keep effective in therapy for a longer period as compared to antibodies against other epitopes. The epitope peptides according to the invention also have the advantage that upon immunization of a subject (e.g., HBV transgenic mouse) with a vaccine comprising the same as active ingredient, HBsAg level and HBV DNA level can be reduced for a long time in the subject.

The embodiments of the invention are described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF THE DRAWINGS

FIG. 2A: Decrease in HBsAg level in serum after treating HBV transgenic mice with mouse monoclonal antibodies and entecavir (ETV), respectively; FIG. 2B: Decrease in HBV DNA level in serum after treating HBV transgenic mice with mouse monoclonal antibodies and entecavir (ETV), respectively; FIG. 2C: Changes in alanine aminotransferase (ALT) level in serum after treating HBV transgenic mice with mouse monoclonal antibodies and entecavir (ETV), respectively.

FIG. 3A: Decrease in HBsAg level in serum after injecting HBV transgenic mice with HBs-E6F6; FIG. 3B: Decrease in HBV DNA level in serum after injecting HBV transgenic mice with HBs-E6F6.

FIG. 5A: Scheme of construction of pC149-SEQ clone; FIG. 5B: Results of SDS-PAGE detection and electron microscopic observation of 9 recombinant proteins.

Figure 8B:
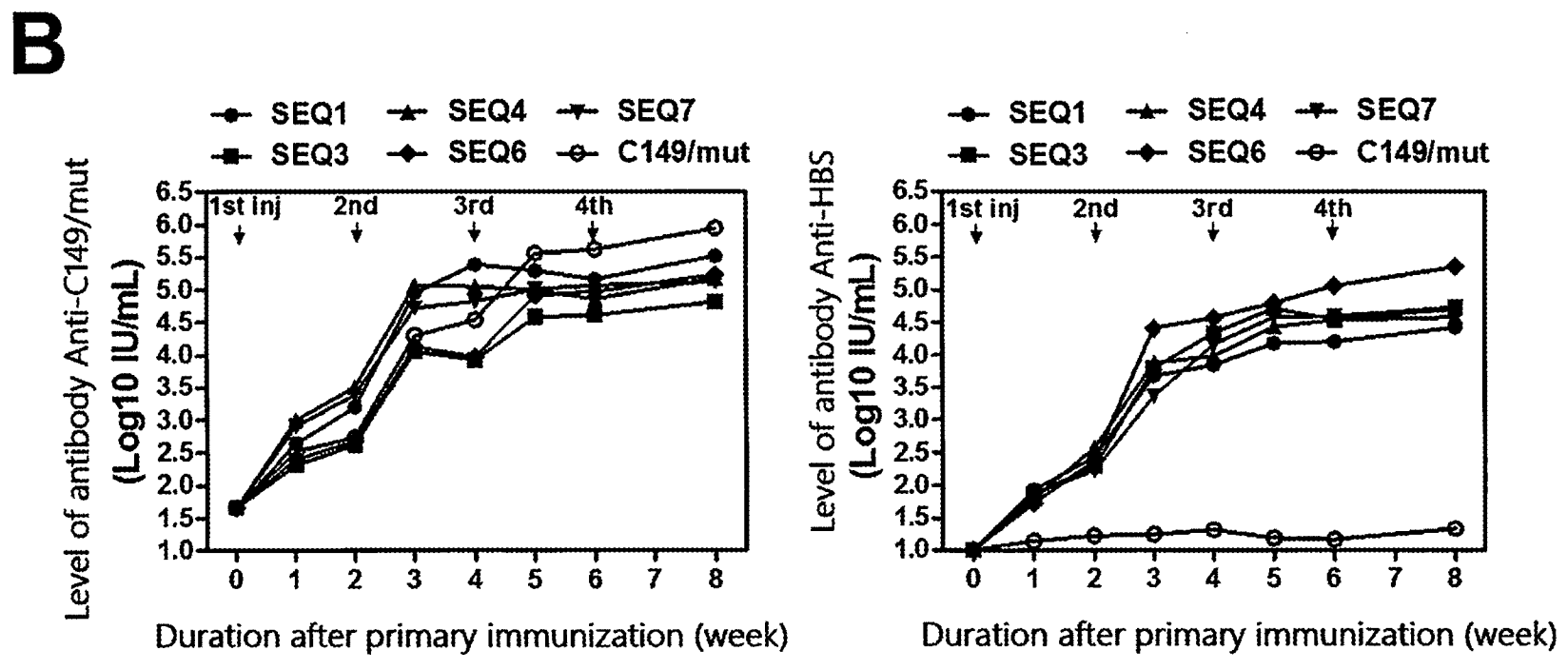

FIGS. 8A-8B: The preparation of 5 recombinant proteins comprising epitope peptides and evaluation of their immunogenicity. FIG. 8A: Results of SDS-PAGE detection and electron microscopic observation of said 5 recombinant proteins. FIG. 8B: Changes in antibody titer in serum after immunizing BALB/C mice with said 5 recombinant proteins.

FIG. 11A: Results of SDS-PAGE detection and electron microscopic observation of said 3 recombinant proteins. FIGS. 11B-11E: Changes in serum HBsAg level, serum HBV DNA level, Anti-HBsAg antibody level, and anti-carrier protein antibody level in mice after immunizing HBV transgenic mice with said 3 recombinant proteins.

SEQUENCE INFORMATION

Figure 1A:
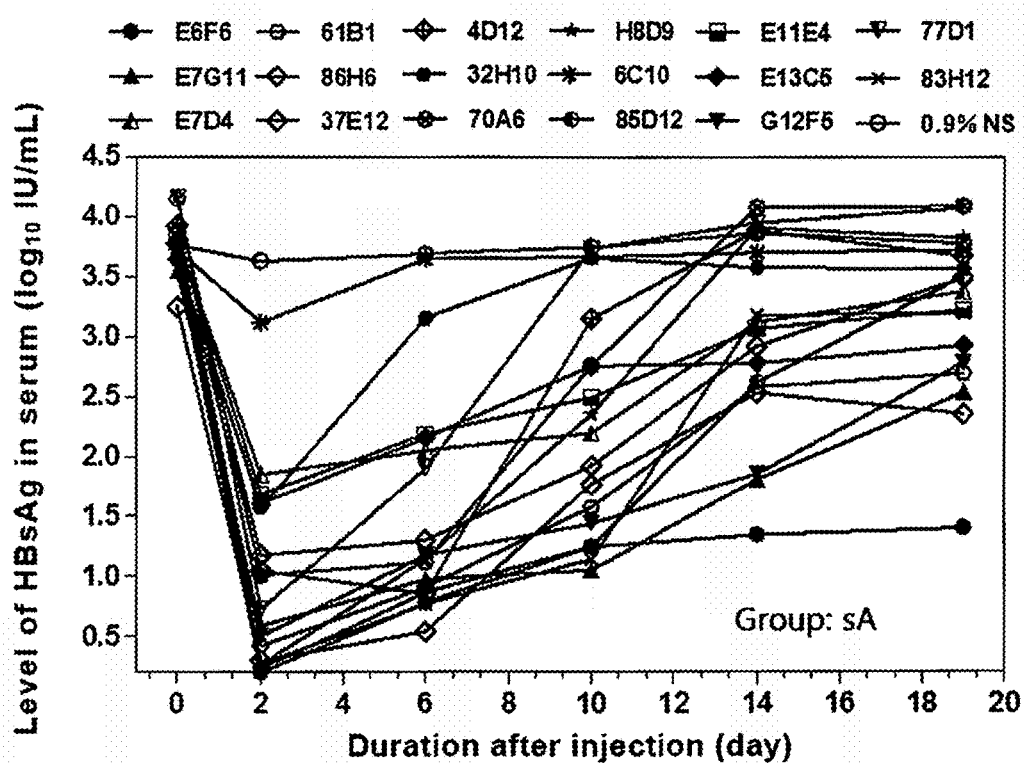
FIGS. 1A-1H: Evaluation of efficacy of different mouse monoclonal antibodies in the treatment of HBV transgenic mice.
Figure 1B:
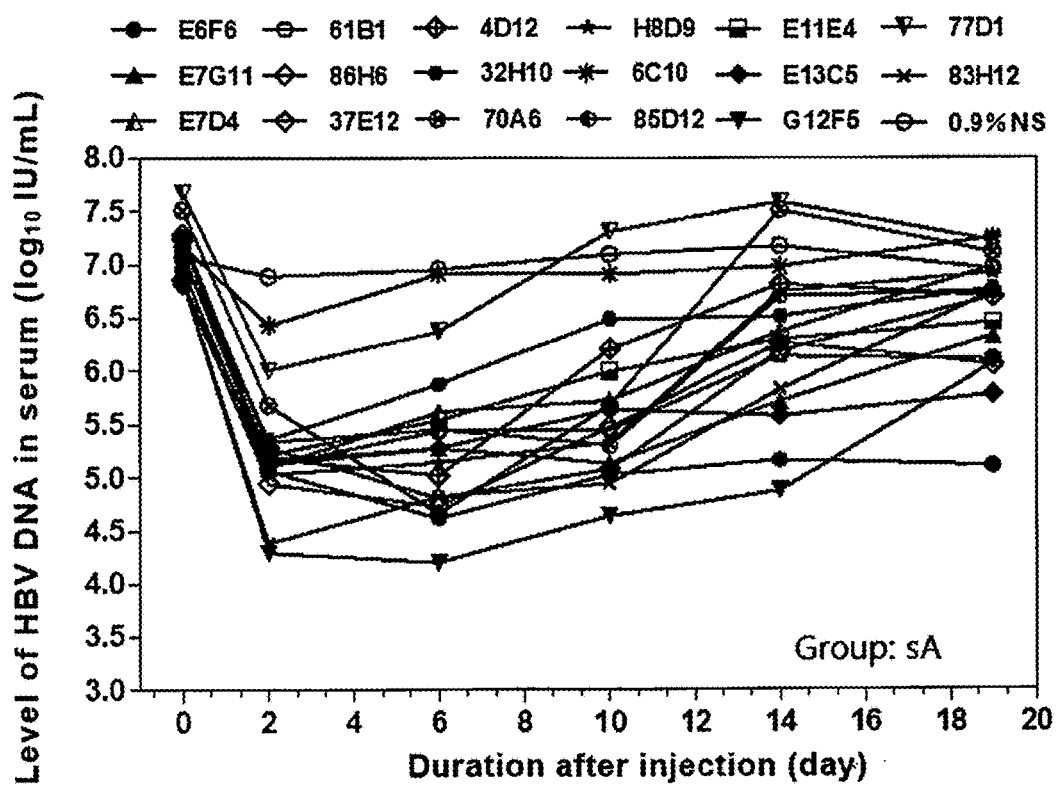
Figure 1C:
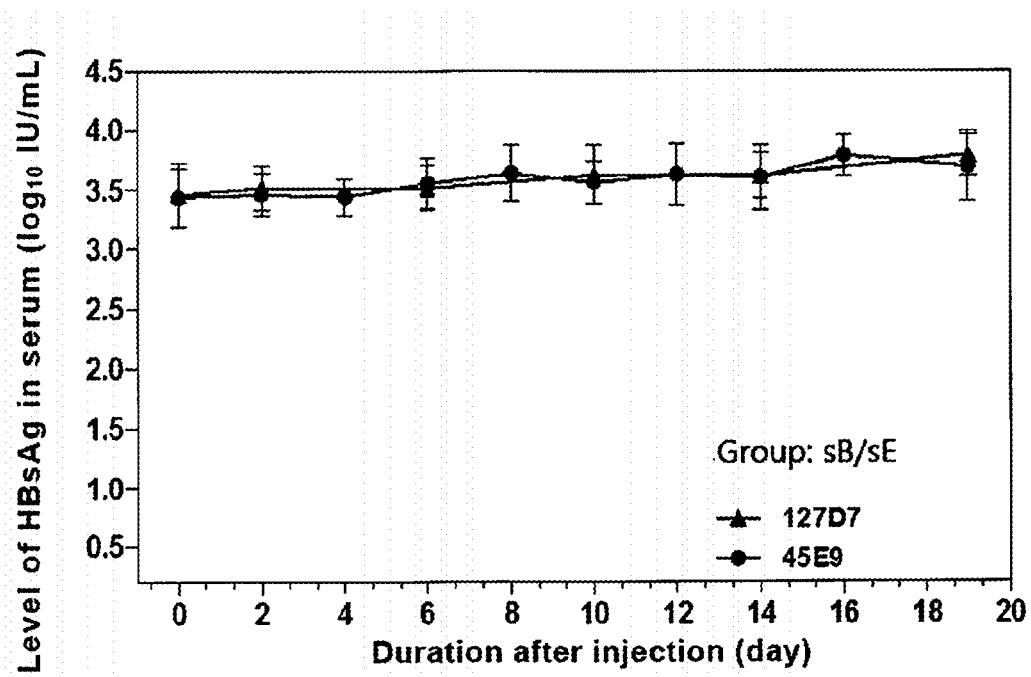
Figure 1D:
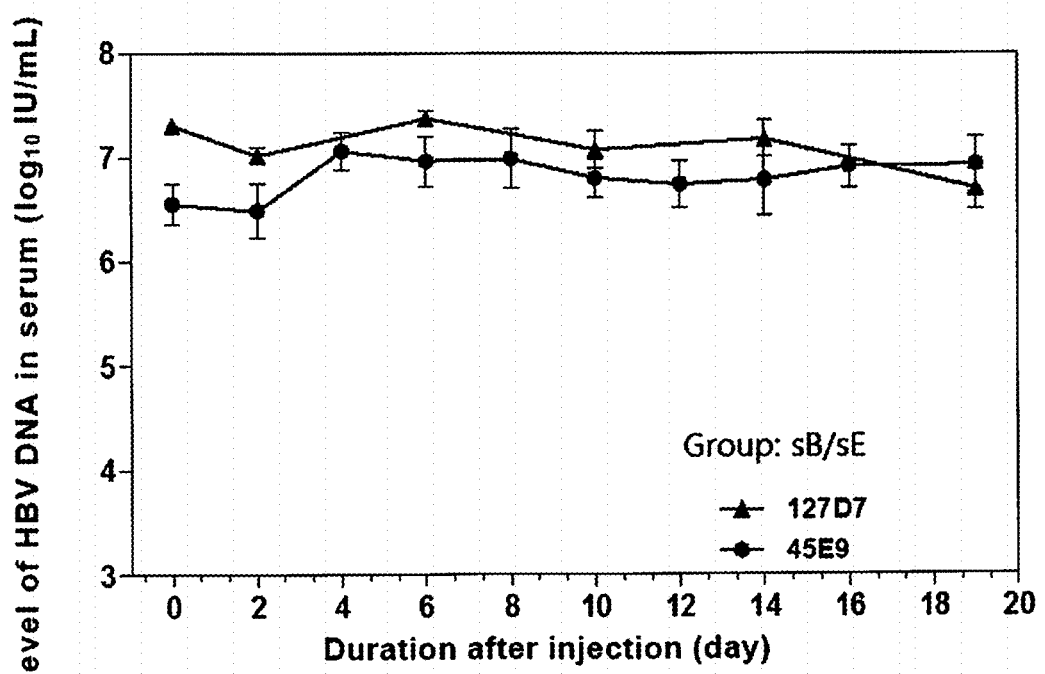
Figure 1E:
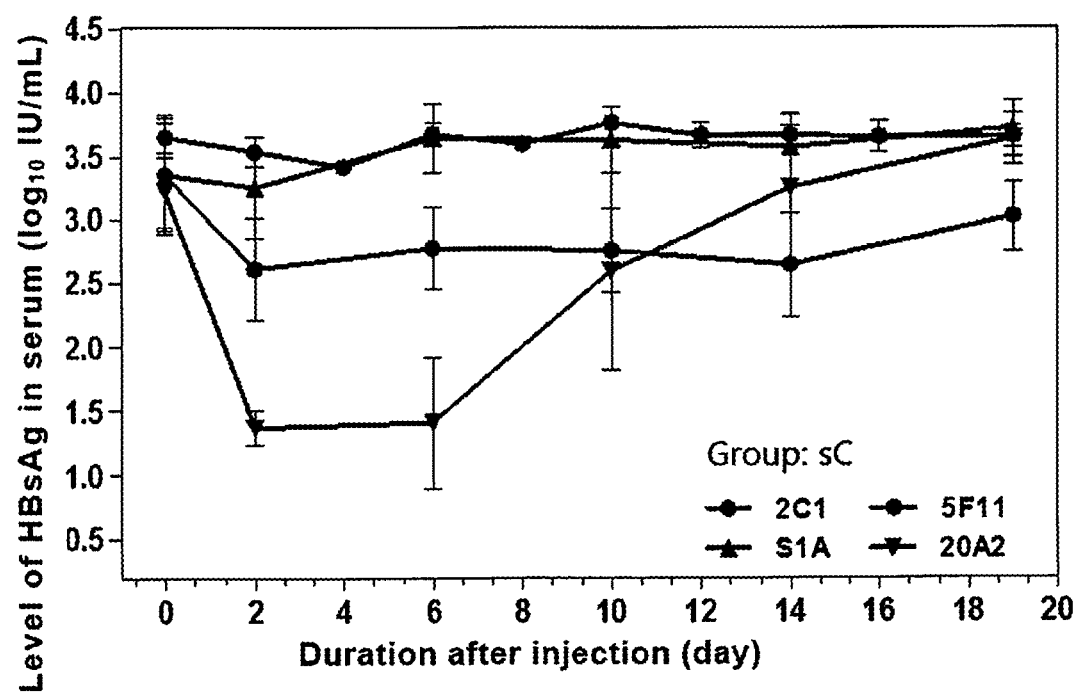
Figure 1F:
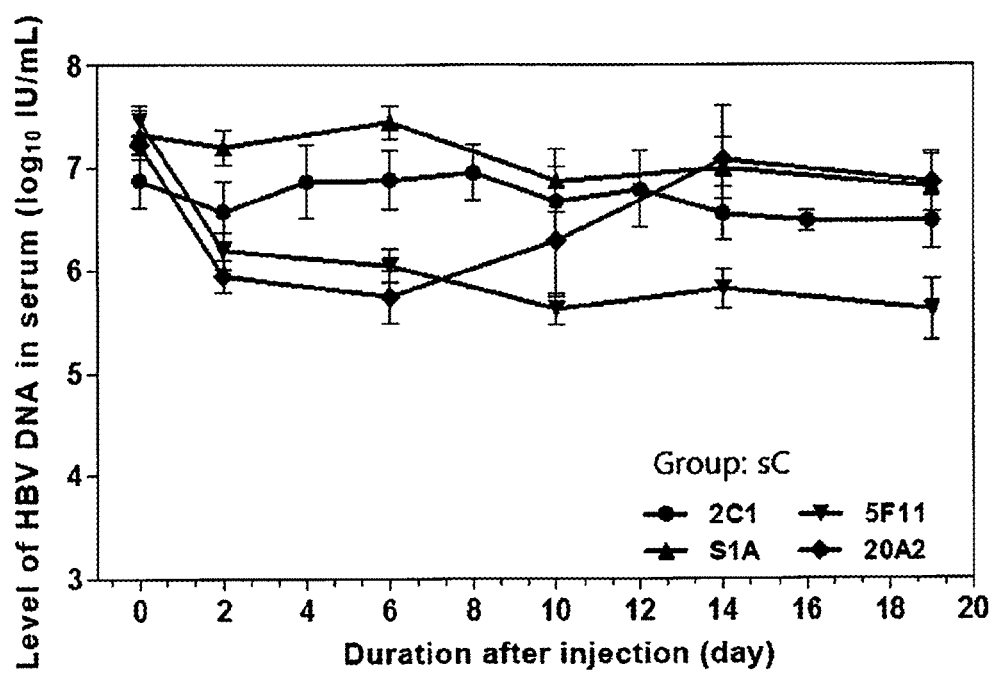
Figure 1G:
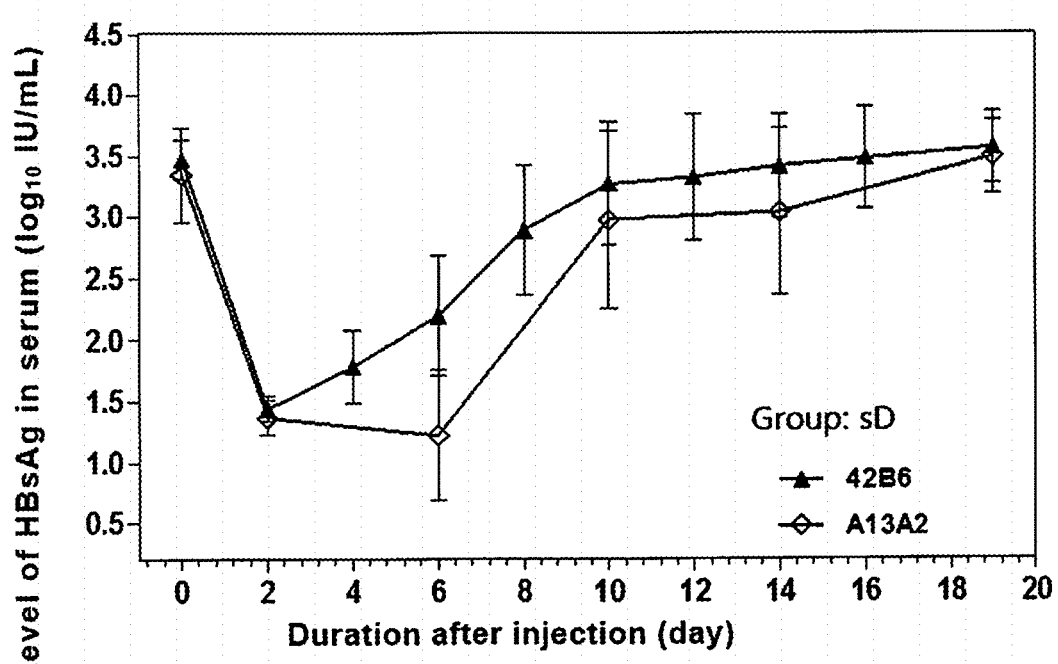
Figure 1H:
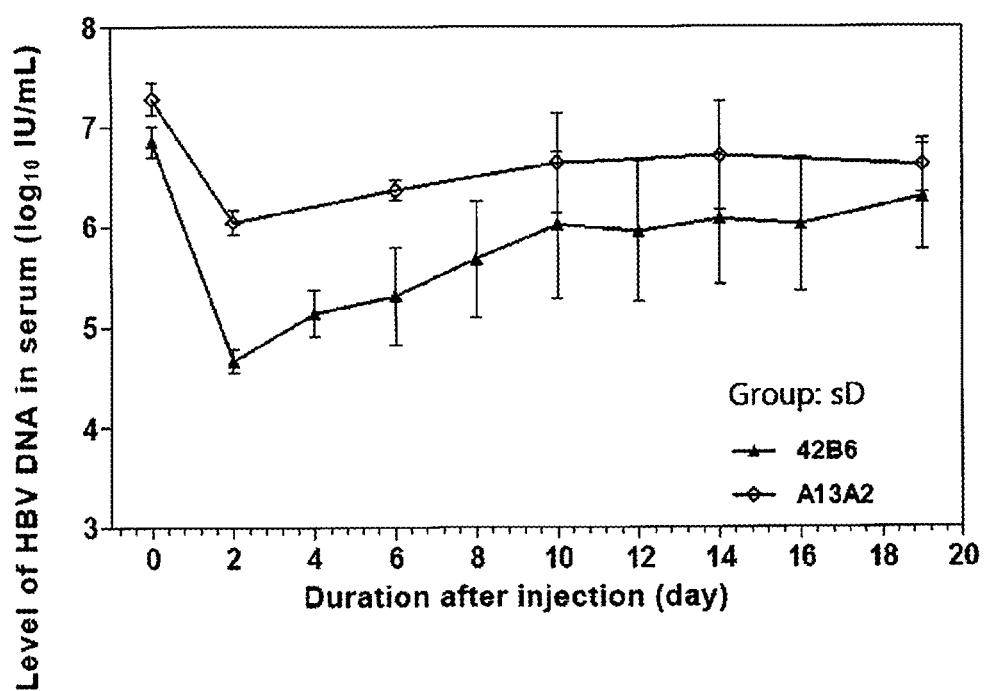

The information on sequences involved in the invention is provided in the following Table 1.

| SEQ ID NO | Name | Sequence information |
|---|---|---|
| 1 | SEQ1 | GPCKTCT |
| 2 | SEQ2 | GPCRTCT |
| 3 | SEQ3 | STTTSTGPCKTCTTP |
| 4 | SEQ4 | TTSTGPCKTCT |
| 5 | SEQ5 | CKTCTTPAQ |
| 6 | SEQ6 | SSTTSTGPCKTCTTPAQGTSMFP |
| 7 | SEQ7 | PGSSTTSTGPCKTCTTPAQGTSMFPSCCCTKPTDGNCT |
| 8 | SEQ8 | STTTSTGPC |
| 9 | SEQ9 | STGPCKT |
| 10 | SEQ10 | CKTC |
| 11 | SEQ11 | TCTTPAQGNSMFPAQ |
| 12 | S1 | MENIASGLLGPLLVL |
| 13 | S2 | LGPLLVLQAGFFLLT |
| 14 | S3 | AGFFLLTKILTIPQS |
| 15 | S4 | ILTIPQSLDSWWTSL |
| 16 | S5 | DSWWTSLNFLGGTPV |
| 17 | S6 | FLGGTPVCLGQNSQS |
| 18 | S7 | LGQNSQSQISSHSPT |
| 19 | S8 | ISSHSPTCCPPICPG |
| 20 | S9 | CPPICPGYRWMCLRR |
| 21 | S10 | RWMCLRRFIIFLCIL |

| SEQ ID NO | Name | Sequence information |
|---|---|---|
| 22 | S11 | IIFLCILLLCLIFLL |
| 23 | S12 | LCLIFLLVLLDYQGM |
| 24 | S13 | LLDYQGMLPVCPLIP |
| 25 | S14 | PVCPLIPGSSTTSTG |
| 26 | S15 | SSTTSTGPCKTCTTP |
| 27 | S16 | CKTCTTPAQGTSMFP |
| 28 | S17 | QGTSMFPSCCCTKPT |
| 29 | S18 | CCCTKPTDGNCTCIP |
| 30 | S19 | GNCTCIPIPSSWAFA |
| 31 | S20 | PSSWAFAKYLWEWAS |
| 32 | S21 | YLWEWASVRFSWLSL |
| 33 | S22 | RFSWLSLLVPFVQWF |
| 34 | S23 | VPFVQWFVGLSPTVW |
| 35 | S24 | GLSPTVWLSVIWMMW |
| 36 | S25 | SVIWMMWFWGPSLYN |
| 37 | S26 | WGPSLYNILSPFMPL |
| 38 | S27 | LSPFMPLLPIFFCLWVYI |
| 39 | HBsAg | MENIASGLLGPLLVLQAGFFLLTKILTIPQSLDSWWTSLNFLGGTPVCLGQ NSQSQISSHSPTCCPPICPGYRWMCLRRFIIFLCILLLCLIFLLVLLDYQGM LPVCPLIPGSSTTSTGPCKTCTTPAQGTSMFPSCCCTKPTDGNCTCIPIPS SWAFAKYLWEWASVRFSWLSLLVPFVQWFVGLSPTVWLSVIWMMWFW GPSLYNILSPFMPLLPIFFCLWVYI |
| 40 | HBcAg | MDIDPYKEFGASVELLSFLPSDFFPSIRDLLDTASALYREALESPEHCSPH HTALRQAILCWGELMNLATWVGSNLEDPASRELVVSYVNVNMGLKIRQL LWFHISCLTFGRETVLEYLVSFGVWIRTPPAYRPPNAPILSTLPETTVVRR RGRSPRRRTPSPRRRRSQSPHRRRSQSRESQC |
| 41 | WHcAg | MDIDPYKEFGSSYQLLNFLPLDFFPDLNALVDTATALYEEELTGREHCSP HHTTIRQALVCWDELTKLIAWMSSNITSEQVRTIIVNYVNDTWGLKVRQSL WFHLSCLTFGQHTVQEFLVSFGVWIRTPAPYRPPNAPILSTLPEHTVIRRR GGARASRSPRRRTPSPRRRRSQSPRRRRSQSPSANC |
| 42 | CRM197 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKTVDHTKVNSKLSLFFEIKS |
| 43 | C149/mut | MDIDPYKEFGASVELLSFLPSDFFPSIRDLLDTASALYREALESPEHCSPH HTALRQAILCWGELMNLATWVGSNLEDGGGGSGGGGTGSFEFGGGGS GGGGSRELVVSYVNVNMGLKIRQLLWFHISCLTFGRETVLEYLVSFGVWI RTPPAYRPPNAPILSTLPETTVV |
| 44 | C183/mut | MDIDPYKEFGASVELLSFLPSDFFPSIRDLLDTASALYREALESPEHCSPH HTALRQAILCWGELMNLATWVGSNLEDGGGGSGGGGTGSFEFGGGGS GGGGSRELVVSYVNVNMGLKIRQLLWFHISCLTFGRETVLEYLVSFGVWI RTPPAYRPPNAPILSTLPETTVVRRRGRSPRRRTPSPRRRRSQSPHRRR SQSRESQC |

| SEQ ID NO | Name | Sequence information |
|---|---|---|
| 45 | WHC149/ mut | MDIDPYKEFGSSYQLLNFLPLDFFPDLNALVDTATALYEEELTGREHCSP HHTTIRQALVCWDELTKLIAWMSSNITSGGGGSGGGGTGSFEFGGGGS GGGGSRTIIVNYVNDTWGLKVRQSLWFHLSCLTFGQHTVQEFLVSFGVW IRTPAPYRPPNAPILSTLPEHTVI |
| 46 | Linker | GGGGSGGGGSGGGGS |
| 47 | C149-SEQ1 | MDIDPYKEFGASVELLSFLPSDFFPSIRDLLDTASALYREALESPEHCSPH HTALRQAILCWGELMNLATWVGSNLEDGGGGSGGGGTGSGPCKTCTEF GGGGSGGGGSRELVVSYVNVNMGLKIRQLLWFHISCLTFGRETVLEYLV SFGVWIRTPPAYRPPNAPILSTLPETTVV |
| 48 | C149-SEQ2 | MDIDPYKEFGASVELLSFLPSDFFPSIRDLLDTASALYREALESPEHCSPH HTALRQAILCWGELMNLATWVGSNLEDGGGGSGGGGTGSGPCRTCTEF GGGGSGGGGSRELVVSYVNVNMGLKIRQLLWFHISCLTFGRETVLEYLV SFGVWIRTPPAYRPPNAPILSTLPETTVV |
| 49 | C149-SEQ3 | MDIDPYKEFGASVELLSFLPSDFFPSIRDLLDTASALYREALESPEHCSPH HTALRQAILCWGELMNLATWVGSNLEDGGGGSGGGGTGSSTTTSTGPC KTCTTPEFGGGGSGGGGSRELVVSYVNVNMGLKIRQLLWFHISCLTFGR ETVLEYLVSFGVWIRTPPAYRPPNAPILSTLPETTVV |
| 50 | C149-SEQ4 | MDIDPYKEFGASVELLSFLPSDFFPSIRDLLDTASALYREALESPEHCSPH HTALRQAILCWGELMNLATWVGSNLEDGGGGSGGGGTGSTTSTGPCKT CTEFGGGGSGGGGSRELVVSYVNVNMGLKIRQLLWFHISCLTFGRETVL EYLVSFGVWIRTPPAYRPPNAPILSTLPETTVV |
| 51 | C149-SEQ5 | MDIDPYKEFGASVELLSFLPSDFFPSIRDLLDTASALYREALESPEHCSPH HTALRQAILCWGELMNLATWVGSNLEDGGGGSGGGGTGSCKTCTTPAQ EFGGGGSGGGGSRELVVSYVNVNMGLKIRQLLWFHISCLTFGRETVLEY LVSFGVWIRTPPAYRPPNAPILSTLPETTVV |
| 52 | C149-SEQ6 | MDIDPYKEFGASVELLSFLPSDFFPSIRDLLDTASALYREALESPEHCSPH HTALRQAILCWGELMNLATWVGSNLEDGGGGSGGGGTGSSSTTSTGPC KTCTTPAQGTSMFPEFGGGGSGGGGSRELVVSYVNVNMGLKIRQLLWF HISCLTFGRETVLEYLVSFGVWIRTPPAYRPPNAPILSTLPETTVV |
| 53 | C149-SEQ7 | MDIDPYKEFGASVELLSFLPSDFFPSIRDLLDTASALYREALESPEHCSPH HTALRQAILCWGELMNLATWVGSNLEDGGGGSGGGGTGSPGSSTTSTG PCKTCTTPAQGTSMFPSCCCTKPTDGNCTEFGGGGSGGGGSRELVVSY VNVNMGLKIRQLLWFHISCLTFGRETVLEYLVSFGVWIRTPPAYRPPNAPI LSTLPETTVV |
| 54 | C149-SEQ8 | MDIDPYKEFGASVELLSFLPSDFFPSIRDLLDTASALYREALESPEHCSPH HTALRQAILCWGELMNLATWVGSNLEDGGGGSGGGGTGSSTTTSTGPC EFGGGGSGGGGSRELVVSYVNVNMGLKIRQLLWFHISCLTFGRETVLEY LVSFGVWIRTPPAYRPPNAPILSTLPETTVV |
| 55 | C149-SEQ9 | MDIDPYKEFGASVELLSFLPSDFFPSIRDLLDTASALYREALESPEHCSPH HTALRQAILCWGELMNLATWVGSNLEDGGGGSGGGGTGSSTGPCKTEF GGGGSGGGGSRELVVSYVNVNMGLKIRQLLWFHISCLTFGRETVLEYLV SFGVWIRTPPAYRPPNAPILSTLPETTVV |
| 56 | C149-SEQ10 | MDIDPYKEFGASVELLSFLPSDFFPSIRDLLDTASALYREALESPEHCSPH HTALRQAILCWGELMNLATWVGSNLEDGGGGSGGGGTGSCKTCEFGG GGSGGGGSRELVVSYVNVNMGLKIRQLLWFHISCLTFGRETVLEYLVSF GVWIRTPPAYRPPNAPILSTLPETTVV |
| 57 | C149-SEQ11 | MDIDPYKEFGASVELLSFLPSDFFPSIRDLLDTASALYREALESPEHCSPH HTALRQAILCWGELMNLATWVGSNLEDGGGGSGGGGTGSTCTTPAQG NSMFPAQEFGGGGSGGGGSRELVVSYVNVNMGLKIRQLLWFHISCLTFG RETVLEYLVSFGVWIRTPPAYRPPNAPILSTLPETTVV |
| 58 | C183-SEQ1 | MDIDPYKEFGASVELLSFLPSDFFPSIRDLLDTASALYREALESPEHCSPH HTALRQAILCWGELMNLATWVGSNLEDGGGGSGGGGTGSGPCKTCTEF GGGGSGGGGSRELVVSYVNVNMGLKIRQLLWFHISCLTFGRETVLEYLV SFGVWIRTPPAYRPPNAPILSTLPETTVVRRRGRSPRRRTPSPRRRRSQS PHRRRSQSRESQC |
| 59 | C183-SEQ2 | MDIDPYKEFGASVELLSFLPSDFFPSIRDLLDTASALYREALESPEHCSPH HTALRQAILCWGELMNLATWVGSNLEDGGGGSGGGGTGSGPCRTCTEF GGGGSGGGGSRELVVSYVNVNMGLKIRQLLWFHISCLTFGRETVLEYLV SFGVWIRTPPAYRPPNAPILSTLPETTVVRRRGRSPRRRTPSPRRRRSQS PHRRRSQSRESQC |

-continued

| SEQ ID NO | Name | Sequence information |
|---|---|---|
| 60 | C183-SEQ3 | MDIDPYKEFGASVELLSFLPSDFFPSIRDLLDTASALYREALESPEHCSPH HTALRQAILCWGELMNLATWVGSNLEDGGGGSGGGGTGSSTTTSTGPC KTCTTPEFGGGGSGGGGSRELVVSYVNVMGLKIRQLLWFHISCLTFGR ETVLEYLVSFGVWIRTPPAYRPPNAPILSTLPETTVVRRRGRSPRRRTPS PRRRRSQSPHRRRSQSRESQC |
| 61 | C183-SEQ4 | MDIDPYKEFGASVELLSFLPSDFFPSIRDLLDTASALYREALESPEHCSPH HTALRQAILCWGELMNLATWVGSNLEDGGGGSGGGGTGSTTSTGPCKT CTEFGGGGSGGGGSRELVVSYVNVMGLKIRQLLWFHISCLTFGRETVL EYLVSFGVWIRTPPAYRPPNAPILSTLPETTVVRRRGRSPRRRTPSPRRR RSQSPHRRRSQSRESQC |
| 62 | C183-SEQ5 | MDIDPYKEFGASVELLSFLPSDFFPSIRDLLDTASALYREALESPEHCSPH HTALRQAILCWGELMNLATWVGSNLEDGGGGSGGGGTGSCKTCTTPAQ EFGGGGSGGGGSRELVVSYVNVMGLKIRQLLWFHISCLTFGRETVLEY LVSFGVWIRTPPAYRPPNAPILSTLPETTVVRRRGRSPRRRTPSPRRRRS QSPHRRRSQSRESQC |
| 63 | C183-SEQ6 | MDIDPYKEFGASVELLSFLPSDFFPSIRDLLDTASALYREALESPEHCSPH HTALRQAILCWGELMNLATWVGSNLEDGGGGSGGGGTGSSSTTSTGPC KTCTTPAQGTSMFPEFGGGGSGGGGSRELVVSYVNVMGLKIRQLLWF HISCLTFGRETVLEYLVSFGVWIRTPPAYRPPNAPILSTLPETTVVRRRGR SPRRRTPSPRRRRSQSPHRRRSQSRESQC |
| 64 | C183-SEQ7 | MDIDPYKEFGASVELLSFLPSDFFPSIRDLLDTASALYREALESPEHCSPH HTALRQAILCWGELMNLATWVGSNLEDGGGGSGGGGTGSPGSSTTSTG PCKTCTTPAQGTSMFPSCCCTKPTDGNCTEFGGGGSGGGGSRELVVSY VNVMGLKIRQLLWFHISCLTFGRETVLEYLVSFGVWIRTPPAYRPPNAPI LSTLPETTVVRRRGRSPRRRTPSPRRRRSQSPHRRRSQSRESQC |
| 65 | C183-SEQ10 | MDIDPYKEFGASVELLSFLPSDFFPSIRDLLDTASALYREALESPEHCSPH HTALRQAILCWGELMNLATWVGSNLEDGGGGSGGGGTGSCKTCEFGG GGSGGGGSRELVVSYVNVMGLKIRQLLWFHISCLTFGRETVLEYLVSF GVWIRTPPAYRPPNAPILSTLPETTVVRRRGRSPRRRTPSPRRRRSQSP HRRRSQSRESQC |
| 66 | WHC149-SEQ1 | MDIDPYKEFGSSYQLLNFLPLDFFPDLNALVDTATALYEEELTGREHCSP HHTTIRQALVCWDELTKLIAWMSSNITSGGGGSGGGGTGSGPCKTCTEF GGGGSGGGGSRTIIVNYVNDTWGLKVRQSLWFHLSCLTFGQHTVQEFLV SFGVWIRTPAPYRPPNAPILSTLPEHTVI |
| 67 | WHC149-SEQ2 | MDIDPYKEFGSSYQLLNFLPLDFFPDLNALVDTATALYEEELTGREHCSP HHTTIRQALVCWDELTKLIAWMSSNITSGGGGSGGGGTGSGPCRTCTEF GGGGSGGGGSRTIIVNYVNDTWGLKVRQSLWFHLSCLTFGQHTVQEFLV SFGVWIRTPAPYRPPNAPILSTLPEHTVI |
| 68 | WHC149-SEQ3 | MDIDPYKEFGSSYQLLNFLPLDFFPDLNALVDTATALYEEELTGREHCSP HHTTIRQALVCWDELTKLIAWMSSNITSGGGGSGGGGTGSSTTTSTGPC KTCTTPEFGGGGSGGGGSRTIIVNYVNDTWGLKVRQSLWFHLSCLTFGQ HTVQEFLVSFGVWIRTPAPYRPPNAPILSTLPEHTVI |
| 69 | WHC149-SEQ4 | MDIDPYKEFGSSYQLLNFLPLDFFPDLNALVDTATALYEEELTGREHCSP HHTTIRQALVCWDELTKLIAWMSSNITSGGGGSGGGGTGSTTSTGPCKT CTEFGGGGSGGGGSRTIIVNYVNDTWGLKVRQSLWFHLSCLTFGQHTV QEFLVSFGVWIRTPAPYRPPNAPILSTLPEHTVI |
| 70 | WHC149-SEQ5 | MDIDPYKEFGSSYQLLNFLPLDFFPDLNALVDTATALYEEELTGREHCSP HHTTIRQALVCWDELTKLIAWMSSNITSGGGGSGGGGTGSCKTCTTPAQ EFGGGGSGGGGSRTIIVNYVNDTWGLKVRQSLWFHLSCLTFGQHTVQE FLVSFGVWIRTPAPYRPPNAPILSTLPEHTVI |
| 71 | WHC149-SEQ6 | MDIDPYKEFGSSYQLLNFLPLDFFPDLNALVDTATALYEEELTGREHCSP HHTTIRQALVCWDELTKLIAWMSSNITSGGGGSGGGGTGSSSTTSTGPC KTCTTPAQGTSMFPEFGGGGSGGGGSRTIIVNYVNDTWGLKVRQSLWF HLSCLTFGQHTVQEFLVSFGVWIRTPAPYRPPNAPILSTLPEHTVI |
| 72 | WHC149-SEQ7 | MDIDPYKEFGSSYQLLNFLPLDFFPDLNALVDTATALYEEELTGREHCSP HHTTIRQALVCWDELTKLIAWMSSNITSGGGGSGGGGTGSPGSSTTSTG PCKTCTTPAQGTSMFPSCCCTKPTDGNCTEFGGGGSGGGGSRTIIVNYV NDTWGLKVRQSLWFHLSCLTFGQHTVQEFLVSFGVWIRTPAPYRPPNAP ILSTLPEHTVI |
| 73 | WHC149-SEQ10 | MDIDPYKEFGSSYQLLNFLPLDFFPDLNALVDTATALYEEELTGREHCSP HHTTIRQALVCWDELTKLIAWMSSNITSGGGGSGGGGTGSCKTCEFGGG |

| SEQ ID NO | Name | Sequence information |
|---|---|---|
| | | GSGGGGSRTIIVNYVNDTWGLKVRQSLWFHLSCLTFGQHTVQEFLVSFG VWIRTPAPYRPPNAPILSTLPEHTVI |
| 74 | CRM197-SEQ1 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKWDHTKVNSKLSLFFEIKSGGGGSGGGGSGGGGSG PCKTCT |
| 75 | CRM197-SEQ2 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKTVDHTKVNSKLSLFFEIKSGGGGSGGGGSGGGGSG PCRTCT |
| 76 | CRM197-SEQ3 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKTVDHTKVNSKLSLFFEIKSGGGGSGGGGSGGGGSS TTTSTGPCKTCTTP |
| 77 | CRM197-SEQ4 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKIKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKTVDHTKVNSKLSLFFEIKSGGGGSGGGGSGGGGST TSTGPCKTCT |
| 78 | CRM197-SEQ5 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFLHDGYAVSWNT VEDSIIRTGFQGESGHDIKITAENTPLPIAGVLLPTIPGKLDVNKSKTHISVN GRKIRMRCRAIDGDVTFCRPKSPVYVGNGVHANLHVAFHRSSSEKIHSN EISSDSIGVLGYQKTVDHTKVNSKLSLFFEIKSGGGGSGGGGSGGGGSC KTCTTPAQ |
| 79 | CRM197-SEQ6 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL |

| SEQ ID NO | Name | Sequence information |
|---|---|---|
| | | VDIGFAAYNFVESIINLFQVVHNSYNRPAYSPGHKTQPFLHDGYAVSWNT<br>VEDSIIRTGFQGESGHDIKITAENTPLPIAGVLLPTIPGKLDVNKSKTHISVN<br>GRKIRMRCRAIDGDVTFCRPKSPVYVGNGVHANLHVAFHRSSSEKIHSN<br>EISSDSIGVLGYQKTVDHTKVNSKLSLFFEIKSGGGGSGGGGSGGGGSS<br>STTSTGPCKTCTTPAQGTSMFP |
| 80 | CRM197-SEQ7 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFLHDGYAVSWNT<br>VEDSIIRTGFQGESGHDIKITAENTPLPIAGVLLPTIPGKLDVNKSKTHISVN<br>GRKIRMRCRAIDGDVTFCRPKSPVYVGNGVHANLHVAFHRSSSEKIHSN<br>EISSDSIGVLGYQKTVDHTKVNSKLSLFFEIKSGGGGSGGGGSGGGGSP<br>GSSTTSTGPCKTCTTPAQGTSMFPSCCCTKPTDGNCT |
| 81 | CRM197-SEQ10 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFLHDGYAVSWNT<br>VEDSIIRTGFQGESGHDIKITAENTPLPIAGVLLPTIPGKLDVNKSKTHISVN<br>GRKIRMRCRAIDGDVTFCRPKSPVYVGNGVHANLHVAFHRSSSEKIHSN<br>EISSDSIGVLGYQKTVDHTKVNSKLSLFFEIKSGGGGSGGGGSGGGGSC<br>KTC |
| 82 | CRM389-SEQ1 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFGGGGSGGGGS<br>GGGGSGPCKTCT |
| 83 | CRM389-SEQ2 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFGGGGSGGGGS<br>GGGGSGPCRTCT |
| 84 | CRM389-SEQ3 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFGGGGSGGGGS<br>GGGGSSTTTSTGPCKTCTTP |
| 85 | CRM389-SEQ4 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY<br>INNWEQAKALSVELEINFETRGKRGQDAMYEYMAQACAGNRVRRSVGS<br>SLSCINLDWDVIRDKTKTKIESLKEHGPIKNKMSESPNKTVSEEKAKQYLE<br>EFHQTALEHPELSELKTVTGTNPVFAGANYAAWAVNVAQVIDSETADNLE<br>KTTAALSILPGIGSVMGIADGAVHHNTEEIVAQSIALSSLMVAQAIPLVGEL<br>VDIGFAAYNFVESIINLFQVVHNSYNRPAYSPGHKTQPFGGGGSGGGGS<br>GGGGSTTSTGPCKTCT |
| 86 | CRM389-SEQ5 | GADDVVDSSKSFVMENFSSYHGTKPGYVDSIQKGIQKPKSGTQGNYDDD<br>WKEFYSTDNKYDAAGYSVDNENPLSGKAGGVVKVTYPGLTKVLALKVDN<br>AETIKKELGLSLTEPLMEQVGTEEFIKRFGDGASRVVLSLPFAEGSSSVEY |

| SEQ ID NO | Name | Sequence information |
|---|---|---|
| | | INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFGGGGSGGGGS GGGGSCKTCTTPAQ |
| 87 | CRM389-SEQ6 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFGGGGSGGGGS GGGGSSSTTSTGPCKTCTTPAQGTSMFP |
| 88 | CRM389-SEQ7 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFGGGGSGGGGS GGGGSPGSSTTSTGPCKTCTTPAQGTSMFPSCCCTKPTDGNCT |
| 89 | CRM389-SEQ10 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRVRRSVGS SLSCINLDWDVIRDKTKTKIESLKEHGPIKNKMSESPNKTVSEEKAKQYLE EFHQTALEHPELSELKTVTGTNPVFAGANYAAWAVNVAQVIDSETADNLE KTTAALSILPGIGSVMGIADGAVHHNTEEIVAQSIALSSLMVAQAIPLVGEL VDIGFAAYNFVESIINLFQVVHNSYNRPAYSPGHKTQPFGGGGSGGGGS GGGGSCKTC |
| 90 | CRMA-SEQ1 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSGPCKTCT |
| 91 | CRMA-SEQ2 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSGPCRTCT |
| 92 | CRMA-SEQ3 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSSTTTSTGPCKTCTTP |
| 93 | CRMA-SEQ4 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSTTTSTGPCKTCT |
| 94 | CRMA-SEQ5 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSCKTCTTPAQ |
| 95 | CRMA-SEQ6 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSSSTTSTGPCKTCTTPAQGTSMFP |
| 96 | CRMA-SEQ7 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN |

| SEQ ID NO | Name | Sequence information |
|---|---|---|
| | | AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSPGSSTTSTGPCKTCTTPAQGTSMFPSCCCTKPTDGNCT |
| 97 | CRMA-SEQ10 | GADDVVDSSKSFVMENFSSYHGTKPGYVDSIQKGIQKPKSGTQGNYDDD WKEFYSTDNKYDAAGYSVDNENPLSGKAGGVVKVTYPGLTKVLALKVDN AETIKKELGLSLTEPLMEQVGTEEFIKRFGDGASRVVLSLPFAEGSSSVEY INNWEQAKALSVELEINFETRGKRGQDAMYEYMAQACAGNRGGGGSGG GGSGGGGSCKTC |

Description of Deposition of Biological Materials

The invention relates to the following biological materials deposited in China Center for Type Culture Collection (CCTCC, Wuhan University, Wuhan, China):

1) hybridoma cell line HBs-E6F6, with an deposition number of CCTCC NO. C201270, deposited on Jun. 7, 2012;
2) hybridoma cell line HBs-E7G11, with an deposition number of CCTCC NO. C201271, deposited on Jun. 7, 2012;
3) hybridoma cell line HBs-G12F5, with an deposition number of CCTCC NO. C201272, deposited on Jun. 7, 2012; and
4) hybridoma cell line HBs-E13C5, with an deposition number of CCTCC NO. C201273, deposited on Jun. 7, 2012.

Specific Modes for Carrying Out the Invention

The present invention is illustrated by reference to the following examples (which are used only for the purpose of illustration and are not intended to limit the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. The reagents used in the present invention, whose manufacturers are not indicated, are conventional products in the art or commercially available. Those skilled in the art understand that the examples are used for illustrating the present invention, but not intended to limit the protection scope of the present invention.

Example 1: Preparation and Property Analysis of Mouse Monoclonal Antibodies

Purpose: obtainment of mouse monoclonal antibodies specific for HBsAg 1.1 Preparation of Anti-HBsAg Mouse Monoclonal Antibodies 1.1.1 Immunization of Mice 1.1.1.1 Preparation of immunogen: immunogen was a recombinant HBV surface antigen protein expressed by CHO (HBsAg, purchased from BEIJING WANTAI BIOLOGY PHARMACY CO., LTD.). The recombinant protein was diluted to a concentration of 0.4 mg/mL, and was mixed with an equivalent volume of Freund's adjuvant, to form a water-in-oil emulsion (a method for determining whether the mixed solution was completely emulsified: a drop of the mixed solution was dropped on the liquid surface of clean water, if the mixed solution aggregated and was not dispersed, it can be believed that the solution was substantially mixed homogeneously). Freund's complete adjuvant was used for primary immunization, and Freund's incomplete adjuvant was used for the subsequent boost immunization, no adjuvant was added for the last boost immunization which was conducted 72 h before fusion.

1.1.1.2 Fundamental immunization of mice: 6-8 week old BALB/c female mice were immunized by subcutaneous multi-point injection of said immunogen at an amount of 400 μL per mouse per time, and 200 μL venous blood of eyeball was collected before each immunization, for titer assay. A boost immunization was performed every two weeks. Indirect ELISA was used to determine serum titer, and when the serum titer of mice was in plateau phase, immunization of mice was stopped and the fusion was performed after resting for 2 months.

1.1.1.3 Final boost 72 h before fusion: final boost of spleen was performed 72 h before fusion of mouse spleen cell and mouse myeloma cell, the immunogen for this boost comprised no adjuvants, injection of 100 μl 0.5 mg/mL recombinant protein was performed. Before immunization of spleen, mice were anaesthetized with ether, abdominal cavity was opened by cutting skin of abdominal wall to take spleen, the spleen was injected with 100 μL antigen vertically, and the cut on skin of abdominal wall was rapidly sutured surgically.

1.1.2 Preparation and Screening of Fused Hybridomas

After final boost which was conducted 72 h before fusion, mouse spleen was taken and was prepared into cell suspension and was subjected to cell fusion with mouse myeloma cells Sp2/0 to obtain hybridoma cells. Previous to this, feeder cells were prepared. During the culture of hybridoma cells, a large number of myeloma cells and splenocytes died one after another in 1640-HAT culture medium after fusion, a single cell or a few scattered cells were not easy to survive, and other cells had to be added to make them survive. The living cells added were known as feeder cells. The laboratory used mouse peritoneal macrophages or thymocytes of 13-day old mice as feeder cells.

1.1.2.1 Preparation of mouse macrophages comprised the following steps. (i) A 6-week old BALB/c mouse was killed by cervical dislocation. The mouse was washed with running water, and bathed in 75% ethanol solution for 5 min; the mouse was placed on a superclean bench, with abdomen upward; skin of the mouse abdomen was lifted with a pair of tweezers; a small hole was cut; the skin was tore upward and downward with a bigger pair of tweezers to ensure sufficient explosure of abdomen. (ii) A pair of aseptic ophthalmic tweezers were used to lift the peritoneum, a small hole was cut in the middle of the peritoneum with another pair of scissors, 1 mL pipette was used to inject a suitable amount of culture medium into the abdominal cavity via the hole, the solution was stirred carefully with the pipette in the abdominal cavity, and the culture medium was sucked out and put in a centrifugation tube. (iii) The cell solution from the abdominal cavity was dissolved in HAT culture medium or HT culture medium, to get macrophagous feeder cells at a concentration of 2×105 cells/mL. (iv) 0.1 mL the feeder cells was added to each well of a 96-well cell culture plate, and was cultured in an incubator; or was added to a 96-well cell culture plate after mixing with fusion cells.

1.1.2.2 Preparation of mouse thymocytes comprised the following steps. (i) A 13-week old BALB/c mouse was killed by cervical dislocation. The mouse was washed with running water and bathed in 75% ethanol solution for 5 min; the mouse was placed on a superclean bench, with abdomen upward. (ii) Skin of the mouse abdomen was lifted with a pair of tweezers, and the outer skin of abdomen and chest was cut. (iii) Another pair of clean scissors was used to cut the thoracic cavity, ivory-white thymus gland was taken out with a pair of tweezers, after grinding, the resultant mixture passed through a 200-mesh cell sieve to get a thymic feeder cell solution.

1.1.2.3 Preparation of mouse myeloma cells comprising the following steps. (i) Mouse myeloma cell line Sp2/0-Ag14 (Sp2/0) was the most ideal fusion cell now as the cell line was easy to culture and has a high fusion rate; however, Sp2/0 myeloma cell line was more sensitive to the culture conditions as compared to NS-1, and did not grow well when it was over-diluted (at a density of less than 3×105/mL) and at basic pH (pH higher than 7.3). (ii) Cells in logarithmic growth phase were chosen for fusion. (iii) Before fusion, myeloma cells were removed from culture flask to a centrifugation tube, and were washed with RPMI-1640 culture medium for three times (1000 rpm×5 min); the cells were re-suspended in RPMI-1640 culture medium, and the cells were counted. (iv) Generally, mouse myeloma cells were thawn 5 days before fusion, and about 6 bottles of 35 cm2 Sp2/0 cells were needed for each fusion.

1.1.2.4 Preparation of immunological splenocyte comprised the following steps. (i) BALB/C mice to be fused were used, the eyeballs were removed and the mice bled to death, the collected blood was used to prepare antiserum, which was used as positive control for antibody detection. The mice were washed with running water and bathed in 75% ethanol solution for 5 min; and the mice was placed on a superclean bench, with right arm recumbent. (ii) Abdominal cavity was opened and spleen was taken out by aseptic operation, the spleen was cut into small pieces, and the small pieces were placed on a 200-mesh cell sieve and were squeezed and ground by a grinding rod (plunger) whilst adding RPMI-1640 culture medium dropwise with a blowpipe. (iii) A suitable amount of RPMI-1640 culture medium was added, and the mixture was kept standing for 3-5 min, the upper ⅔ of the suspension was removed to a 50 mL plastic centrifugation tube; the operation was repeated for 2-3 times. (iv) The cells were washed with RPMI-1640 culture medium for three times (1000 rpm×10 min). (v) The cells were re-suspended in RPMI-1640 culture medium, and the number of cells was counted.

1.1.2.5 The preparation of hybridomas by fusion using PEG fusogen comprised the following steps. (i) Before fusion, 1 mL PEG-1500 and 10 mL RPMI-1640 serum-free culture medium and 200 mL complete medium were preheated to 37° C. (ii) The prepared myeloma cells and splenocytes were mixed in a 50 mL centrifuge tube (1×108 splenocytes+1×107 myeloma cells, about 10:1), and were centrifugated at 1500 rpm×8 min; after centrifugation, the tube was flicked at the bottom to make the cells loose and be paste. (iii) 1 mL suction pipet was used to remove 0.8 mL (1×108 splenocytes+0.8 mL PEG) to a centrifugation tube under slight stirring, and the addition of PEG was finished within 60 s, followed by the addition of 10 mL RPMI-1640 complete medium that was preheated to 37° C., under mild stirring. Finally, RPMI-1640 culture medium was added to 40 mL, and centrifugation at 1000 rpm×5 min was performed. (iv) The supernatant was discarded, and a few amount of HT culture medium was used to blow off the cells carefully, and the cells were removed to a prepared HT culture medium and were added to a 96-well cell culture plate, at 0.1 mL per well; and were cultured in a CO2 incubator. (v) After 12 h, a suitable amount of HAT complete medium was prepared, and 0.1 mL of the medium was added to each well; 5 days later, HT complete medium was used to replace 50-100% of the cell supernatant in wells; about 9-14 days later, the supernatant was taken for detection.

1.1.2.6 Screening of hybridomas: by indirect ELISA screening, the plate was coated with the recombinant antigen HBsAg at 100 ng/well, 50 uL cell supernant was added, and positive clone wells were picked.

1.1.2.7 Cloning of hybridoma cells: limiting dilution assay was used, cells were firstly diluted to a given concentration gradient, and then were seeded to each well of a 96-well cell culture plate, with one cell grew in each well as far as possible. Hybridoma monoclonal positive cell line generally had to be cloned repeatedly for 2-3 times, and was regarded as stable clone line until 100% positive was reached.

1.1.3 Production of MAb Ascites 2-3 BALB/c mice were used, and 0.5 mL saxol was injected to abdominal cavity. After 1 week, hybridoma cells in logarithmic growth phase were centrifugated at 1000 rpm for 5 min, and the supernatant was discarded. The hybridoma cells were suspended in serum-free culture medium, and the number of cells was adjusted to (1-2)×106/mL, and 0.5 mL of the suspension was injected to abdominal cavity of each mouse. 7-10 d later, mice were killed by cervical dislocation when the abdominal cavity was inflated obviously. The mice were washed with running water, embathed, and bathed in 75% ethanol for 5 min. The abdomen of the mouse was upward, and the four limbs were fixed onto a dissecting table with syringe needles. Skin of the mouse abdomen was lifted with a pair of tweezers, a small hole was cut, and then the skin was cut from both sides to dorsum of the mouse. The skin was tore upward and downward with a bigger pair of tweezers to ensure sufficient explosure of abdomen. A pair of aspetic ophthalmic tweezers was used to lift the peritoneum, a small hole was cut in the middle of the peritoneum, and then 1 mL pipette was used to take all the ascites from the abdominal cavity. The ascites collected was mixed and centrifugated in a centrifuge tube at 3000 rpm for 20 min. The supernatant was collected after centrifugation.

1.1.4 Purification of MAb Ascites

After ammonium sulfate precipitation and Protein A affinity chromatography (purchased from US GE Co.), purified monoclonal antibodies were obtained.

1.2 Analysis on Properties of Anti-HBsAg Mouse Monoclonal Antibodies 1.2.1 Synthesis of Polypeptides HBV sequence (GenBank ID: AAF24729.1) was used as reference sequence, and 27 polypeptides were synthesized (synthesized by XiaMen Jingju Biology Science Co., Ltd.). Said 27 polypeptides (S1-S27) together covered full-length 226 amino acids of HBsAg. Information on polypeptides S1-S27 was shown in Table 2. The full-length amino acid sequence of HBsAg was set forth in SEQ ID NO: 42.

TABLE 2

Information on polypeptides S1-S27

| Name | Amino acid position | Amino acid sequence |
|---|---|---|
| S1 | HBsAg-aa1-aa15 | MENIASGLLGPLLVL |
| S2 | HBsAg-aa9-aa23 | LGPLLVLQAGFFLLT |
| S3 | HBsAg-aa17-aa31 | AGFFLLTKILTIPQS |
| S4 | HBsAg-aa25-aa39 | ILTIPQSLDSWWTSL |
| S5 | HBsAg-aa33-aa47 | DSWWTSLNFLGGTPV |
| S6 | HBsAg-aa41-aa55 | FLGGTPVCLGQNSQS |
| S7 | HBsAg-aa49-aa63 | LGQNSQSQISSHSPT |
| S8 | HBsAg-aa57-aa71 | ISSHSPTCCPPICPG |
| S9 | HBsAg-aa65-aa79 | CPPICPGYRWMCLRR |
| S10 | HBsAg-aa73-aa87 | RWMCLRRFIIFLCIL |
| S11 | HBsAg-aa81-aa95 | IIFLCILLLCLIFLL |
| S12 | HBsAg-aa89-aa103 | LCLIFLLVLLDYQGM |
| S13 | HBsAg-aa97-aa111 | LLDYQGMLPVCPLIP |
| S14 | HBsAg-aa105-aa119 | PVCPLIPGSSTTSTG |
| S15 | HBsAg-aa113-aa127 | SSTTSTGPCKTCTTP |
| S16 | HBsAg-aa121-aa135 | CKTCTTPAQGTSMFP |
| S17 | HBsAg-aa129-aa143 | QGTSMFPSCCCTKPT |
| S18 | HBsAg-aa137-aa151 | CCCTKPTDGNCTCIP |
| S19 | HBsAg-aa145-aa159 | GNCTCIPIPSSWAFA |
| S20 | HBsAg-aa153-aa167 | PSSWAFAKYLWEWAS |
| S21 | HBsAg-aa161-aa175 | YLWEWASVRFSWLSL |
| S22 | HBsAg-aa169-aa183 | RFSWLSLLVPFVQWF |
| S23 | HBsAg-aa177-aa191 | VPFVQWFVGLSPTVW |
| S24 | HBsAg-aa185-aa199 | GLSPTVWLSVIWMMW |
| S25 | HBsAg-aa193-aa207 | SVIWMMWFWGPSLYN |
| S26 | HBsAg-aa201-aa215 | WGPSLYNILSPFMPL |
| S27 | HBsAg-aa209-aa226 | LSPFMPLLPIFFCLWVYI |

1.2.2 Assay on Reactivity of Anti-HBsAg Mouse Monoclonal Antibodies with Polypeptides S1-S27

(1.2.2.1) Preparation of Reaction Plates

The polypeptides were diluted with pH9.6 50 mM CB buffer (NaHCO3/Na2CO3 buffer, a final concentration of 50 mM, pH 9.6) to a final concentration of 1 µg/mL; to each well of a 96-well ELISA plate, 100 µL coating solution was added, the coating was performed at 2~8° C. for 16~24 h, and then was performed at 37° C. for 2 h. The plate was washed with PBST solution (20 mM PB7.4, 150 mM NaCl, 0.1% Tween20) once; 200 µL blocking solution (pH 7.4 20 mM $Na_2HPO_4$/$NaH_2PO_4$ buffer containing 20% fetal bovine serum and 1% casein) was then added to each well, and the blocking was performed at 37° C. for 2 h; the blocking solution was discarded. After drying, the plate was packaged in an aluminum foil bag and was stored at 2-8° C. for further use.

(1.2.2.2) ELISA of Anti-HBsAg Mouse Monoclonal Antibodies

25 Anti-HBsAg mouse monoclonal antibodies obtained in 1.1 were diluted with PBS solution containing 20% newborn calf serum to a concentration of 1 µg/mL, for qualitative ELISA.

Sample reaction: 100 µL diluted sample was added to each well of 27 ELISA plates coated with polypeptides, and the plates were placed in an incubator at 37° C. for 30 min.

Enzyme labelling reaction: after sample reaction step was finished, the ELISA plate was washed with PBST solution (20 mM PB7.4, 150 mM NaCl, 0.1% Tween20) for 5 times, 100 µL HRP-labelled goat anti-mouse IgG (GAM) (purchased from BEIJING WANTAI BIOLOGY PHARMACY CO., LTD) was added to each well, and the plate was placed in an incubator at 37° C. for 30 min.

Color development reaction: After the enzyme labelling reaction, the ELISA plate was washed with PBST solution (20 mM PB7.4, 150 mM NaCl, 0.1% Tween20) for 5 times, 50 µL TMB colour developing reagent (purchased from BEIJING WANTAI BIOLOGY PHARMACY CO., LTD) was added to each well, and the plate was placed in an incubator at 37° C. for 15 min.

Stopping reaction and value readout: After the color development reaction step was finished, 50 µL stopping buffer (purchased from BEIJING WANTAI BIOLOGY PHARMACY CO., LTD) was added to each well of the ELISA plate, and OD450/630 value was readout with ELIASA for each well.

Determination of reactivity of Anti-HBsAg mouse monoclonal antibodies with 27 polypeptides: the reactivity was determined by the read values. If test value/background value was above 5, the sample was regarded as positive.

(1.2.2.3) Analysis of Recognization Properties of Anti-HBsAg Mouse Monoclonal Antibodies The results were shown in Table 3. The types recognized by 25 Anti-HBsAg mouse monoclonal antibodies may be divided into 5 groups (depending on the recognization properties), i.e. sA, sB, sC, sD, sE, wherein antibodies of sA group recognized polypeptides S15 and S16; the antibodies of sB group recognized polypeptide S16; antibodies of group sC showed negative in the reaction with said 27 polypeptides; the antibodies of sD group recognized the polypeptide S18; and the antibodies of sE group recognized the polypeptide S8.

TABLE 3

Analysis of properities of Anti-HBsAg mouse monoclonal antibodies

| Group | Recognized polypeptides | Antibody name | Antibody subtype |
|---|---|---|---|
| sA | S15, S16 | HBs-E7G11 | IgG1 |
| sA | S15, S16 | HBs-G12F5 | IgG1 |
| sA | S15, S16 | HBs-E6F6 | IgG1 |
| sA | S15, S16 | HBs-E13C5 | IgG1 |

TABLE 3-continued

Analysis of properities of Anti-HBsAg mouse monoclonal antibodies

| Group | Recognized polypeptides | Antibody name | Antibody subtype |
|---|---|---|---|
| sA | S15, S16 | HBs-3E9 | IgG1 |
| sA | S15, S16 | HBs-77D1 | IgG2a |
| sA | S15, S16 | HBs-86H6 | IgG2b |
| sA | S15, S16 | HBs-4D12 | IgG2b |
| sA | S15, S16 | HBs-32H10 | IgG1 |
| sA | S15, S16 | HBs-70A6 | IgG1 |
| sA | S15, S16 | HBs-6C10 | IgM |
| sA | S15, S16 | HBs-61B1 | IgG1 |
| sA | S15, S16 | HBs-37E12 | IgG2b |
| sA | S15, S16 | HBs-85D12 | IgG1 |
| sA | S15, S16 | HBs-H8D9 | IgG1 |
| sA | S15, S16 | HBs-E11E4 | IgG2a |
| sA | S15, S16 | HBs-83H12 | IgG1 |
| sB | S16 | HBs-127D7 | IgG1 |
| sC | no | HBs-2C1 | IgG1 |
| sC | no | HBs-S1A | IgG2a |
| sC | no | HBs-5F11 | IgG2a |
| sC | no | HBs-20A2 | IgG2b |
| sD | S18 | HBs-42B6 | IgG1 |
| sD | S18 | HBs-A13A2 | IgG2b |
| sE | S8 | HBs-45E9 | IgG3 |

Example 2: Evaluation of Efficacy of Anti-HBsAg Mouse Monoclonal Antibodies in the Treatment of HBV Transgenic Mice Purpose:

Evaluation of efficacy of Anti-HBsAg mouse monoclonal antibodies in the treatment of HBV transgenic mice 2.1 Establishment of Denaturation-Chemiluminescence Quantitative Assay of HBsAg After treatment, a large number of antibodies were present in serum, and therefore the determination of HBsAg might be disturbed by antigen-antibody complexes. Thus, it needs to establish a method for quantitative determination of HBsAg without interference from antibodies. The inventors had the antigen-antibody complexes lyzed in samples by denaturation method so as to exclude interference from antibodies and to carry out accurate quantitative assay of HBsAg.

2.1.1 Preparation of Reaction Plates

The mouse monoclonal antibody HBs-45E9 was diluted with pH7.4 20 mM PB buffer (Na2HPO4/NaH2PO4 buffer, a final concentration of 50 mM, pH 7.4) to a final concentration of 2 µg/mL; to each well of a 96-well ELISA plate, 100 µL coating solution was added, the coating was performed at 2~8° C. for 16~24 h, and then at 37° C. for 2 h. The plate was washed with PBST solution (20 mM PB7.4, 150 mM NaCl, 0.1% Tween20) once; 200 µL blocking solution (pH 7.4 20 mM Na2HPO4/NaH2PO4 buffer containing 20% fetal bovine serum and 1% casein) was then added to each well, the blocking was performed at 37° C. for 2 h; and the blocking solution was discarded. After drying, the plate was packaged in an aluminum foil bag and was stored at 2-8° C. for further use.

2.1.2 Denaturation-Chemiluminescence Quantitative Assay of HBsAg

Sample dilution: mouse serum was diluted with PBS solution containing 20% new-born calf serum to 2 gradient concentrations, i.e. 1:30 and 1:150.

Sample denaturation: 15 µL said diluted sample was mixed with 7.5 µL denaturation buffer (15% SDS, dissolved in 20 mM PB7.4), the mixed solution was incubated at 37° C. for 1 h, and 90 µL neutralization buffer (4% CHAPS, dissolved in 20 mM PB7.4) was then added to the mixed solution, and the resultant solution was mixed homogeneously.

Sample reaction: 100 µL said mixed solution sample obtained by the denaturation treatment was added to the reaction plate. The plate was placed in an incubator at 37° C. for 60 min.

Enzyme labelling reaction: after sample reaction step was finished, the chemiluminescent reaction plate was washed with PBST solution (20 mM PB7.4, 150 mM NaCl, 0.1% Tween20) for 5 times, 100 µL HBs-A6A7-HRP solution (provided by BEIJING WANTAI BIOLOGY PHARMACY CO., LTD) was added to each well, and the plate was placed in an incubator at 37° C. for 60 min.

Luminous reaction and determination: after enzyme labelling reaction step was finished, the chemiluminescent reaction plate was washed with PBST solution (20 mM PB7.4, 150 mM NaCl, 0.1% Tween20) for 5 times, Luminous solution (provided by BEIJING WANTAI BIOLOGY PHARMACY CO., LTD) was added for determining light intensity.

The obtainment of HBsAg concentration in a sample to be tested: standard substances were used for the same experiment, and standard curve was plotted with the results of the standard substances (linear regression of the light intensity values and concentration values); according to the standard curve, the HBsAg concentration in a sample to be tested was obtained by calculation.

2.2 Real-Time Fluorescent Quantitative Assay of HBV DNA

Real-time fluorescent quantitative assay kit of HBV DNA was purchased from SHANGHAI KEHUA BIO-ENGINEERING CO., LTD., and real-time fluorescent quantitative assay of HBV DNA was conducted according to the instruction of the kit.

2.3 Efficacy of Anti-HBsAg Mouse Monoclonal Antibodies in the Treatment of HBV Transgenic Mice 25 antibodies obtained in Example 1 were injected to caudal vein of HBV transgenic mice at a single dose of 20 mg/kg. HBV transgenic mice injected with normal saline (0.9% NS) were used as negative control group. Each group included 4 HBV transgenic mice, two were male and the other two were female. Mouse blood was taken from periorbital venous plexus, and HBsAg and HBV DNA level in mouse serum were monitored.

The results are shown in FIGS. 1A-1H. The results indicated that after HBV transgenic mice were treated with five groups of Anti-HBsAg mouse monoclonal antibodies against different epitopes, antibodies of sA and sD groups showed the effect of significant viral clearance; HBsAg and HBV DNA level were significantly decreased in serum of mice from treatment group using the two groups of antibodies; After treatment with the other three groups of antibodies, HBsAg and HBV DNA level were not significantly decreased in mouse serum. Among the antibodies of sA and sD groups, HBsAg and HBV DNA level in serum were decreased to a larger extent after treatment with antibodies of sA group relative to the treatment with antibodies of sD group, and the four antibodies with the longest duration of inhibition belonged to antibodies of sA group, which were HBs-E6F6, HBs-E7G11, HBs-G12F5, HBs-E13C5, respectively.

Example 3: Efficacy and Side-Effect of Mouse Monoclonal Antibodies of sA Group in the Treatment of HBV Transgenic Mice Purpose: evaluation of efficacy and side-effect of mouse monoclonal antibodies of sA group in the treatment of HBV transgenic mice, monitoring the duration of effective inhibition of viruses after treatment with a single dose of an antibody, and monitoring ALT.

Four antibodies HBs-E6F6, HBs-E7G11, HBs-G12F5, HBs-E13C5 having the best therapeutic effect, as screened in Example 2, were chosen for the experiment, and were injected to caudal vein of HBV transgenic mice at a single dose of 20 mg/kg. HBV transgenic mice treated with normal saline (0.9% NS) were used as negative control group, and HBV transgenic mice treated with 3.2 mg/kg/d entecavir (ETV) administrated by intragastric route were used as effective drug control group. Each group included 4 HBV transgenic mice, two were male and the other two were female. Mouse blood was taken from periorbital venous plexus, and HBsAg, HBV DNA, ALT level in mouse serum were monitored.

According to the methods described in Example 2, HBsAg and HBV DNA level were determined, and ALT was determined by alanine aminotransferase (ALT) assay kit provided by BEIJING WANTAI BIOLOGY PHARMACY CO., LTD.

Figure 2A:
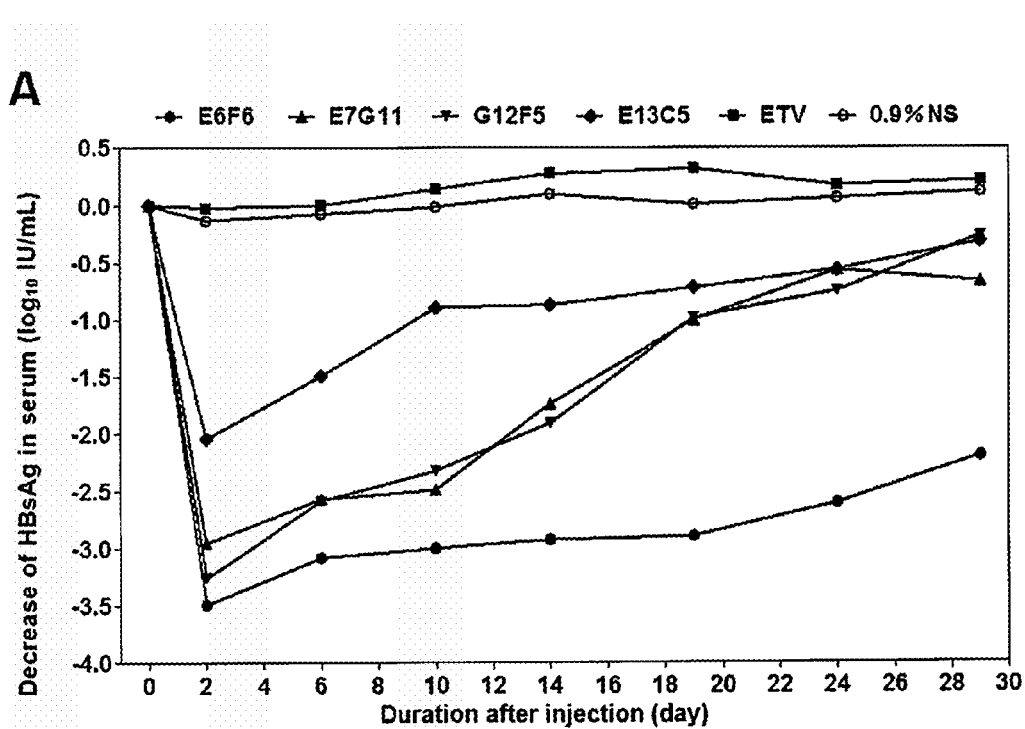
FIGS. 2A-2C: Evaluation of efficacy of HBs-E6F6, HBs-E7G11, HBs-G12F5, HBs-E13C5, 0.9% NS and entecavir (ETV) in the treatment of HBV transgenic mice. The values shown therein are the average values of 4 mice in each experimental group.
Figure 2B:
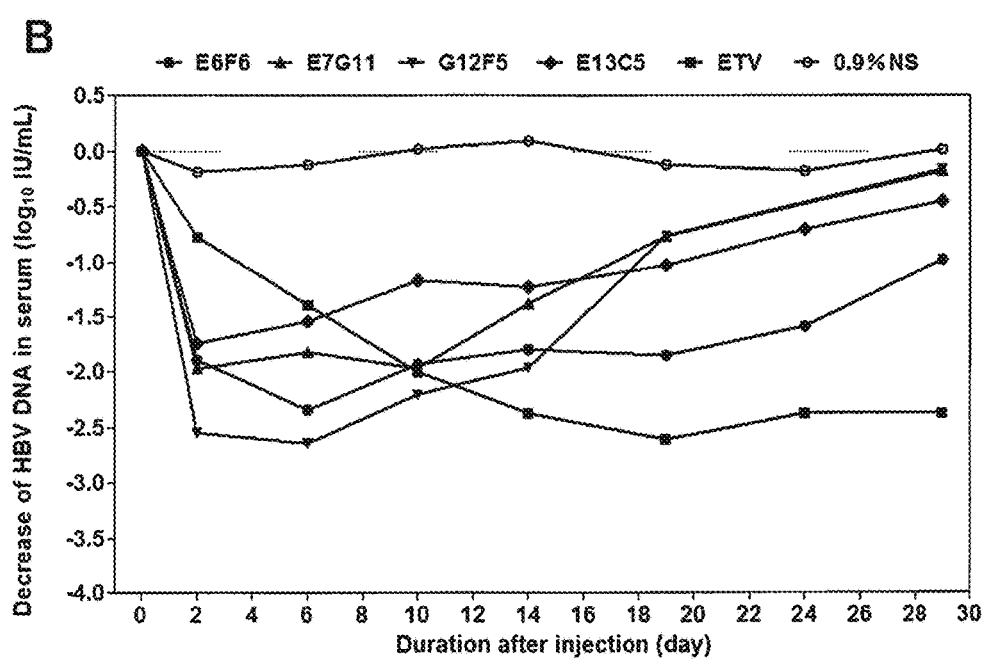
Figure 2C:
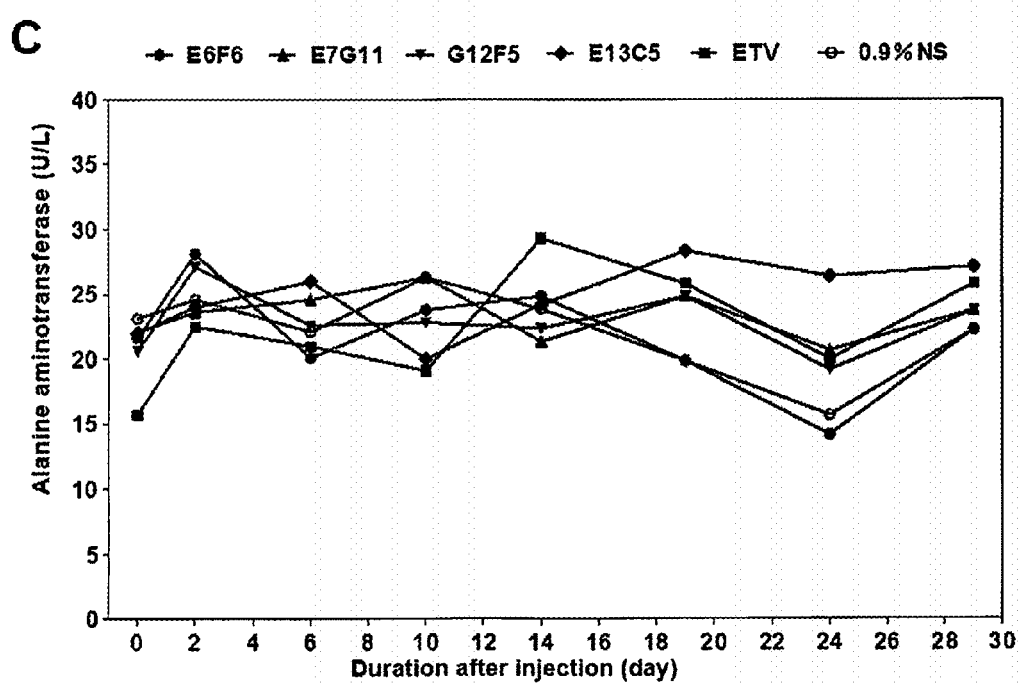

The results of treating HBV transgenic mice with HBs-E6F6, HBs-E7G11, HBs-G12F5, HBs-E13C5, 0.9% NS or entecavir (ETV) are shown in FIGS. 2A-2C (the values showed were the average values of four mice of each experimental group). The results indicated that after treatment with single dose of monoclonal antibody HBs-E6F6, HBs-E7G11, HBs-G12F5 or HBs-E13C5, HBsAg and HBV DNA level were significantly decreased in serum of HBV transgenic mice, wherein the antibody treatment group was comparable to ETV treatment group with respect to the decrease in HBV DNA level. By contrast, HBsAg level did not significantly decrease in serum of mice of ETV treatment group, while HBsAg level decreased significantly in serum in antibody treatment group. In addition, during the treatment with any of the antibodies, no increase in ALT was observed.

Example 4: Dynamic Changes in HBV DNA and HBsAg after the Injection of HBs-E6F6

Purpose: study on the shortest time that monoclonal antibodies take to exert the maximal efficacy The mouse monoclonal antibody HBs-E6F6 having the best effect was selected from four antibodies used in Example 3, and was injected to caudal vein of HBV transgenic mice at a single dose of 20 mg/kg. In the experiment, 4 male mice were used, and dynamic changes in HBV DNA and HBsAg in mouse serum were monitored.

According to the methods described in Example 2, HBsAg and HBV DNA level in serum were determined.

Figure 3A:
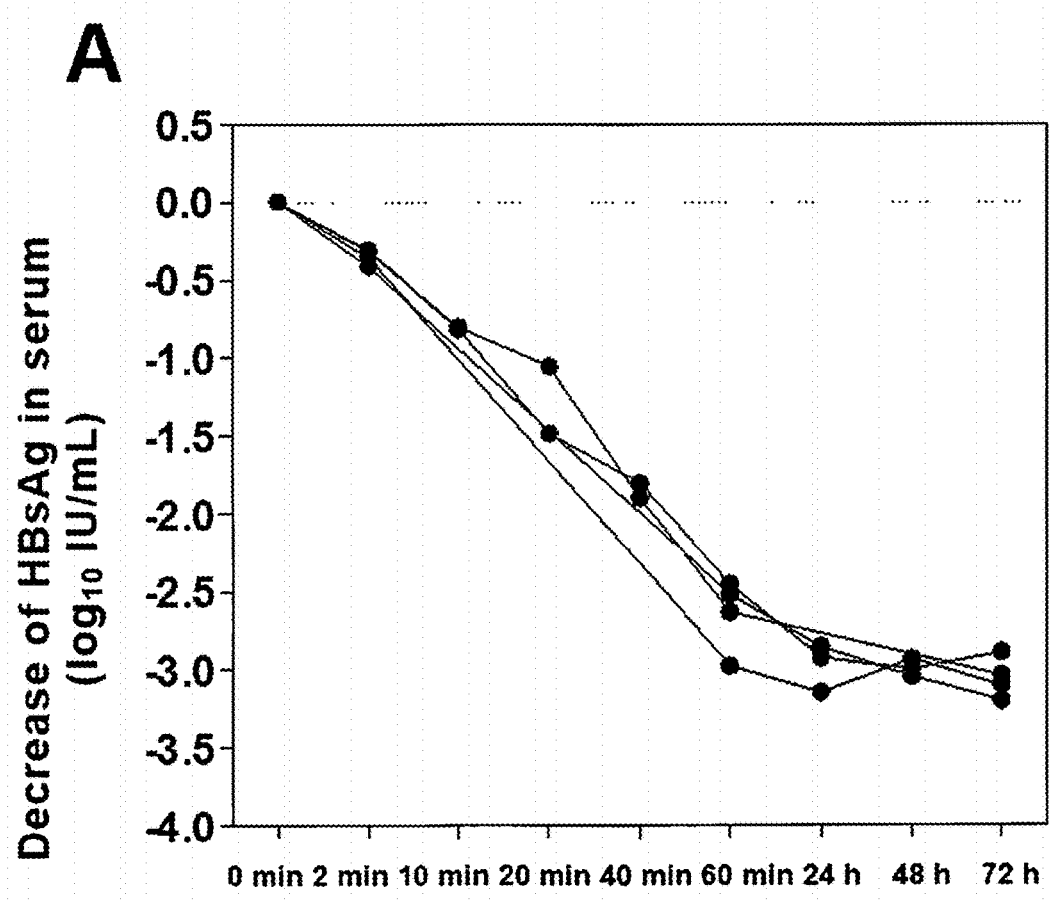
FIGS. 3A-3B: Dynamic changes in HBV DNA and HBsAg after the injection of HBs-E6F6.
Figure 3B:
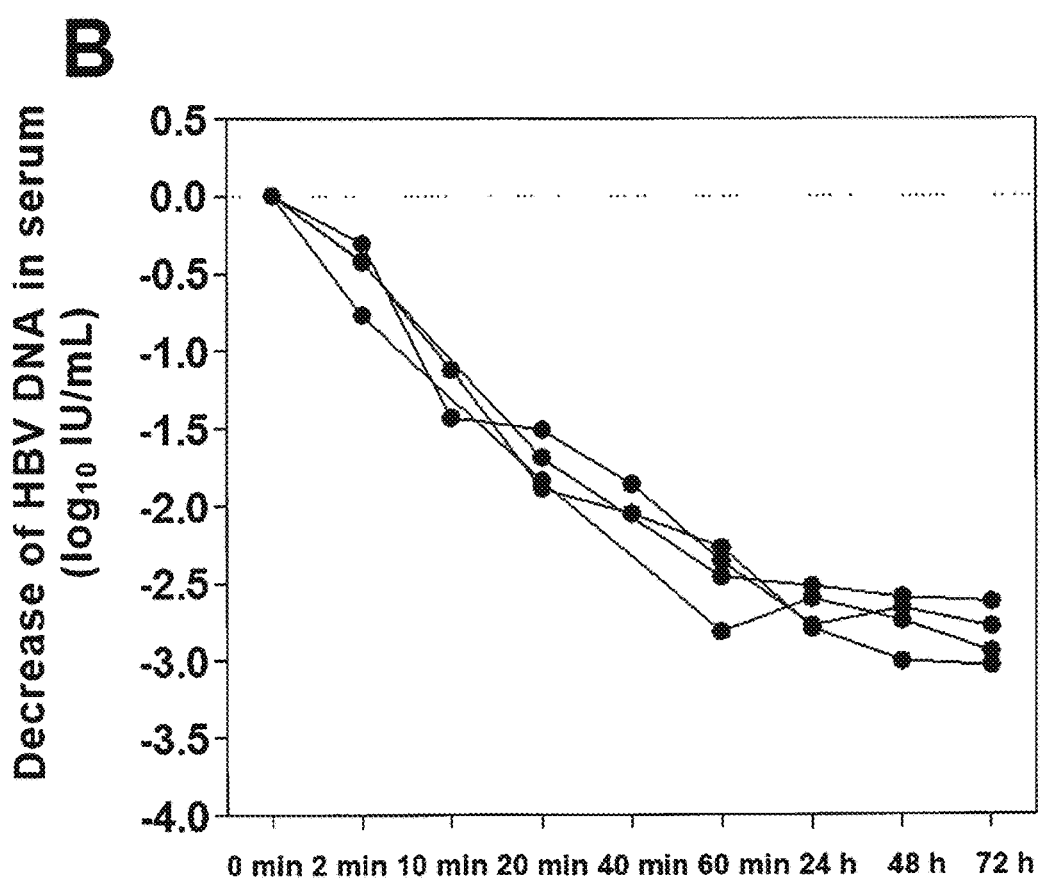

The results are shown in FIGS. 3A-3B. The results indicated that HBsAg and HBV DNA level in mouse serum decreased to the maximal inhibition level within 1 to 24 h after the injection.

Example 5: Evaluation of Therapeutic Effect of Human-Mouse Chimeric Antibody HBs-E6F6 and HBs-E7G11

Purpose: evaluation of therapeutic effect of chimeric antibodies

Figure 4A:
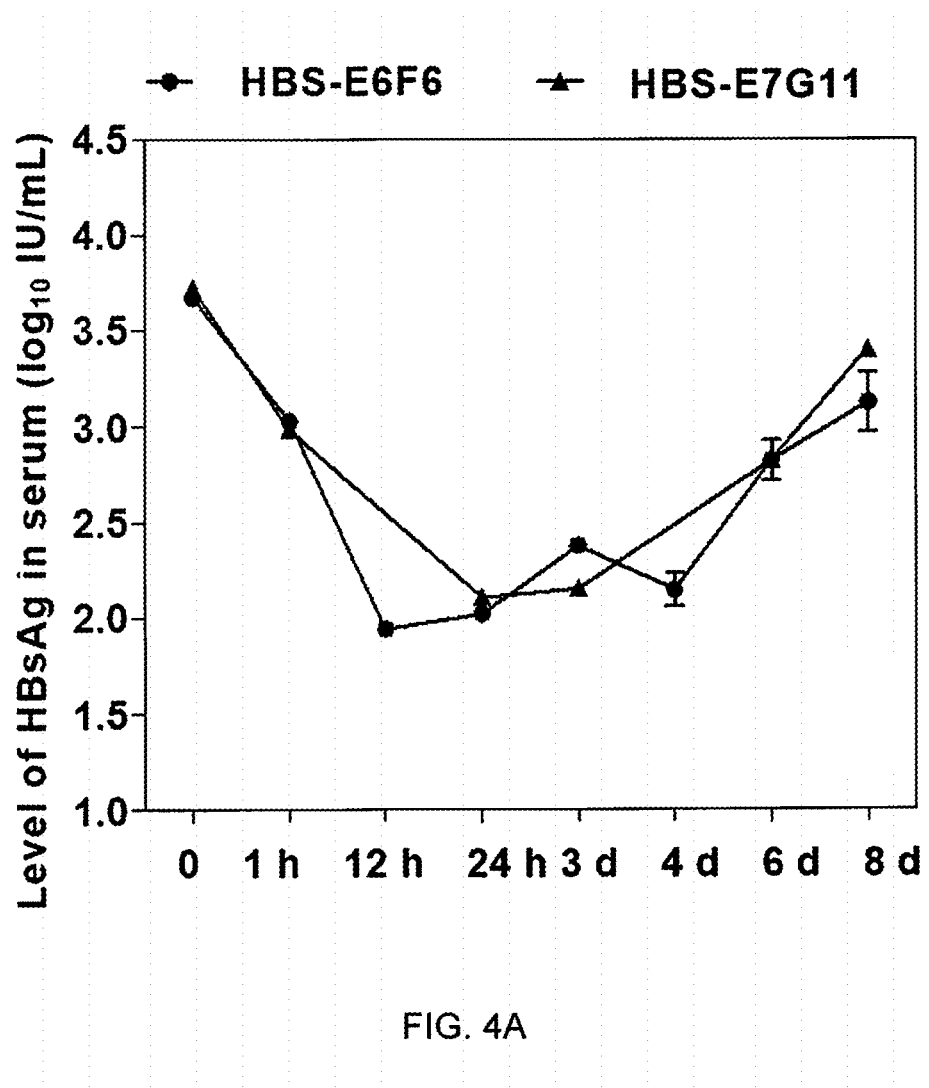
FIGS. 4A-4B: Evaluation of efficacy of chimeric antibodies in the treatment of HBV transgenic mice.
Figure 4B:
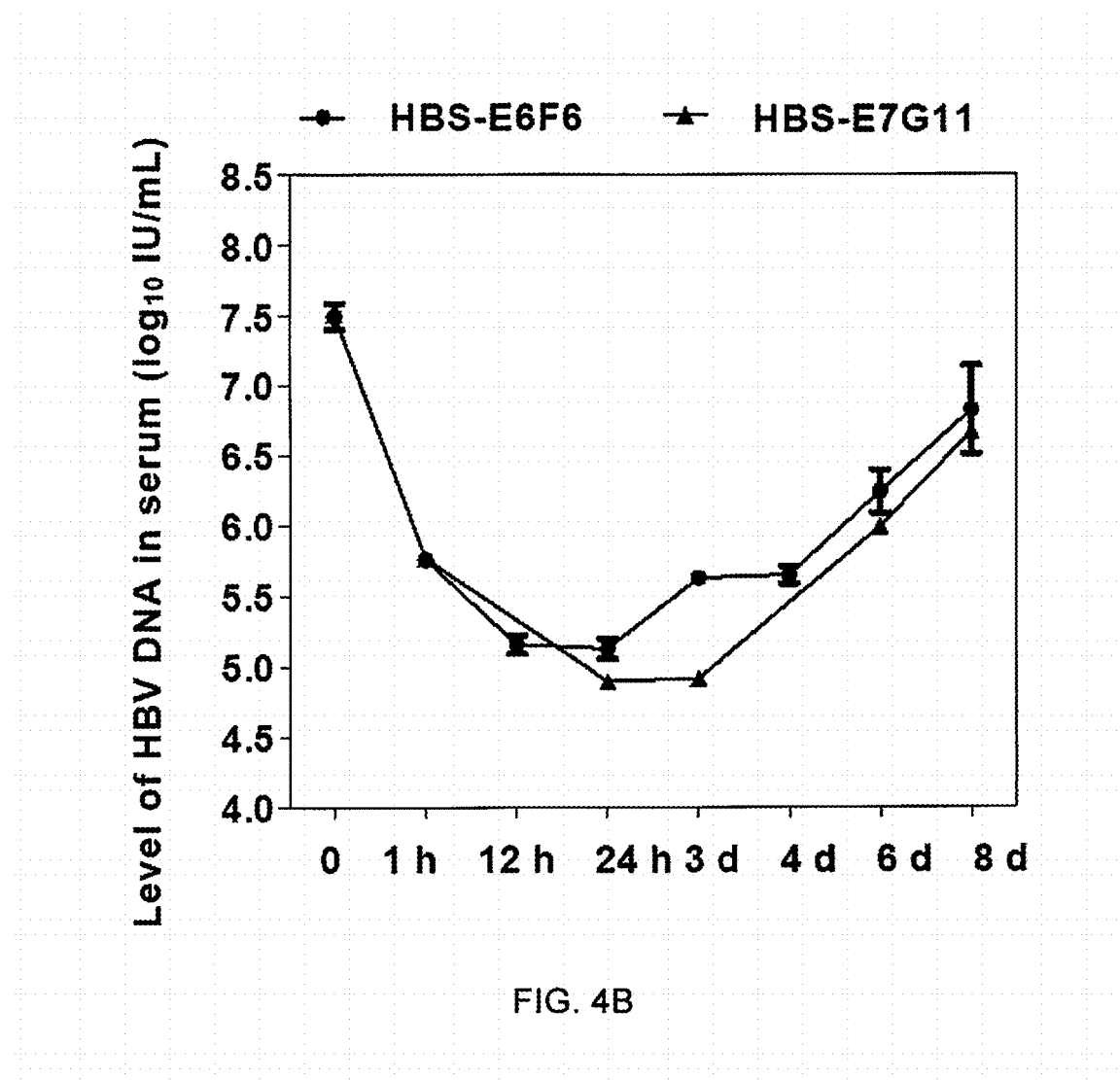

Igv gene of HBs-E6F6 and HBs-E7G11 antibody was linked to Igc gene encoding human antibody constant region, and the chimeric antibody HBs-E6F6 and the chimeric antibody HBs-E7G11 were obtained through recombinant expression in CHO cells and purification. The chimeric antibodies were injected to caudal vein of HBV transgenic mice at a single dose of 10 mg/kg. Dynamic changes in HBV DNA and HBsAg in mouse serum were monitored. The results are shown in FIGS. 4A-4B. The results indicated that both the chimeric antibody HBs-E6F6 and the chimeric antibody HBs-E7G11 can effectively eliminate HBsAg and HBV DNA in mice.

Example 6: Identification of Epitopes Recognized by Antibodies of sA Group

Purpose: Identification of epitopes recognized by antibodies of sA group and determination of the recognized core amino acid sequence 6.1 Construction of pC149-SEQ Clone When HBcAg was used as a carrier protein, full-length HBcAg protein or a fragment thereof (e.g., N-terminal aa 1-149 of HBcAg protein) might be used (see, Yang Haijie et al., Construction of Peptide Display Vector Based on HBV Core Protein, JOURNAL OF XIAMEN UNIVERSITY (NATURAL SCIENCE), 2004.05, Vol. 43, No. 4). In this experiment, a fragment of HBcAg protein (aa 1-149) was used as a carrier protein to construct a series of clones.

Figure 5A:
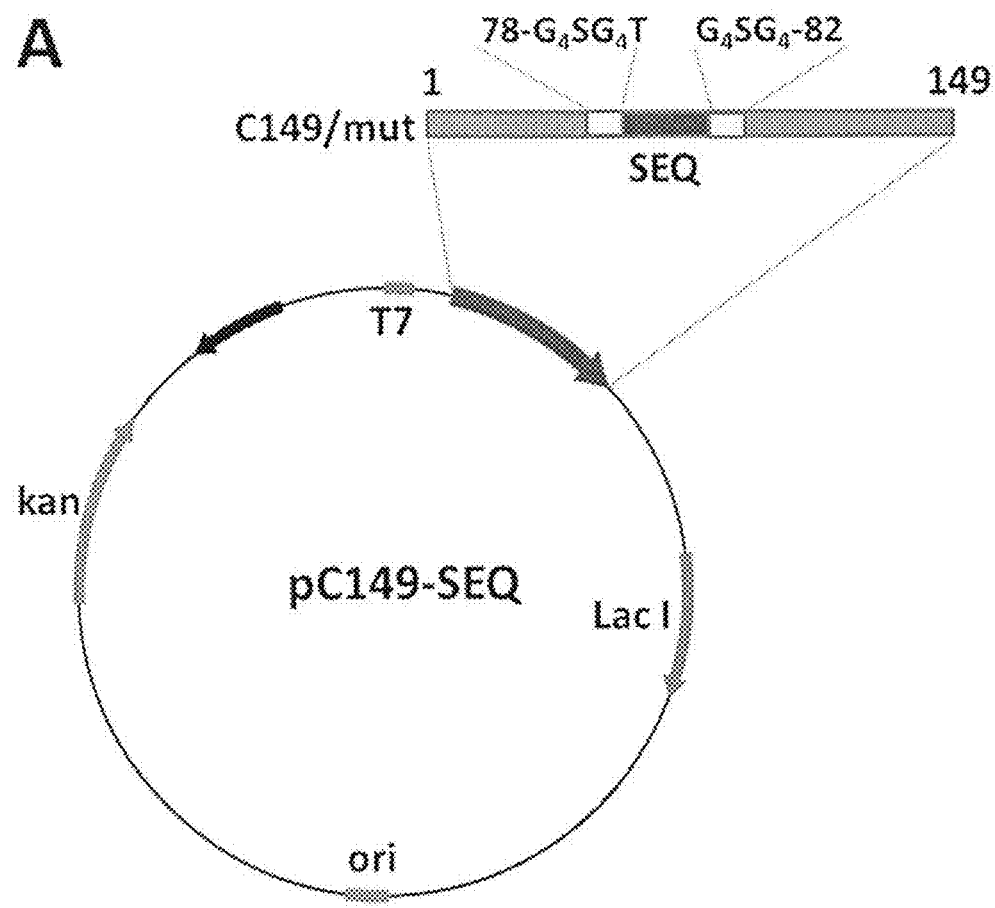
FIGS. 5A-5B: Construction, expression, purification and electron microscopic observation of 9 recombinant proteins.

The sequence encoding HBcAg aa79-81 was deleted from the nucleotide sequence encoding a fragment of HBcAg protein (aa 1-149) by site-directed mutagenesis, two linkers were separately introduced to the two ends of the deletion, BamH I/EcoR I digestion site was designed between the two linkers, and thus the sequence encoding the carrier protein C149/mut (the amino acid sequence of C149/mut was set forth in SEQ ID NO: 43, with a structure of HBc (1-78)-G4SG4T-GS-G4SG4-HBc (82-149); in C149/mut, 3 amino acids (aa 79-81) of HBcAg were replaced with the flexible linker rich in Gly, G4SG4T-GS-G4SG4) was obtained. The sequence encoding C149/mut was cloned into pTO-T7 prokaryotic expression vector (Luo Wenxin, et al., Chinese Journal of Biotechnology, 2000, 16:53-57), to get the recombinant plasmid pC149/mut, which encoded the protein C149/mut. Later, by using BamH I/EcoR I digestion site, the sequence encoding the polypeptide of interest (represented by SEQ in FIG. 5A) was cloned between the flexible linkers to obtain the recombinant vector pC149-SEQ, which encoded the recombinant protein C149-SEQ (comprising the carrier protein C149/mut and the polypeptide of interest SEQ). The clone design and structure of the recombinant vector pC149-SEQ are shown in FIG. 5A.

The gene sequences of the 9 polypeptides shown in Table 4 were separately ligated to the recombinant plasmid pC149/mut, to obtain 9 pC149-SEQ recombinant vectors (pC149-SEQ1, 3, 4, 5, 6, 8, 9, 10, 11), which encoded the recombinant protein C149-SEQ1, 3, 4, 5, 6, 8, 9, 10, 11, respectively.

TABLE 4

Polypeptides of interest presented by C149/mut

| Polypeptide name | Polypeptide position | Amino acid sequence |
|---|---|---|
| SEQ1 | HBsAg-aa119-aa125 | GPCKTCT |
| SEQ3 | HBsAg-aa113-aa127 | STTTSTGPCKTCTTP |
| SEQ4 | HBsAg-aa115-aa125 | TTSTGPCKTCT |
| SEQ5 | HBsAg-aa121-aa129 | CKTCTTPAQ |

TABLE 4-continued

Polypeptides of interest presented by C149/mut

| Polypeptide name | Polypeptide position | Amino acid sequence |
|---|---|---|
| SEQ6 | HBsAg-aa113-aa135 | STTTSTGPCKTCTTPAQGNSMFP |
| SEQ8 | HBsAg-aa113-aa121 | STTTSTGPC |
| SEQ9 | HBsAg-aa117-aa123 | STGPCKT |
| SEQ10 | HBsAg-aa121-aa124 | CKTC |
| SEQ11 | HBsAg-aa123-aa137 | TCTTPAQGNSMFPAQ |

6.2 Expression and Purification of C149-SEQ Proteins

Expression and purification of a recombinant protein were described by using C149-SEQ6 as an example.

(6.2.1) Obtainment of high-efficiency expression strains: according to the method described in 6.1, the vector of interest pC149-SEQ6 was constructed, after identification with DNA sequencing, the vector of interest was transformed into *E. coli* ER2566 strain (*E. coli*, ER2566), to get an expression strain.

(6.2.2) Expression of C149-SEQ6 protein: the expression strain was seeded to a triangular flask (500 mL), and was cultured in a shaking table at 37° C. until OD was about 1.0. Isopropyl β-D-Thiogalactopyranoside (IPTG) was added to a final concentration of 0.5 mM, the expression was induced under shaking at 25° C. for 6 h.

(6.2.3) Purification of C149-SEQ6 protein:

(6.2.3.1) Ultrasonication of bacteria: bacteria in 6.2.2 were collected by centrifugation; bacteria were subjected to ultrasonication, the ultrasonication buffer comprising the components: 20 mM phosphate buffer (PH6.0) +300 mM NaCl.

(6.2.3.2) Primary purification of proteins of interest: since proteins of interest were thermotolerant, the ultrasonated mixture was put in water bath at 65° C. for 30 min, and the supernatant was collected after centrifugation. The supernant was added to a saturated ammonium sulfate solution at a volume ratio of 1:1, and the precipitate was collected after centrifugation. An appropriate volume of buffer was added to resuspend the precipitate to get primarily purified proteins of interest, wherein the buffer comprised 20 mM phosphate buffer (pH=7.4)+150 mM NaCl.

(6.2.3.3) Chromatographic purification of proteins of interest: the proteins obtained in 6.2.3.2 were further purified by Sepharose 4FF (GE) molecular sieve column chromatography to obtain the purified proteins of interest. The purified proteins of interest were subjected to SDS-PAGE, and the assembly state of the particles of the proteins of interest was observed by transmission electron microscope (TEM).

Figure 5B:
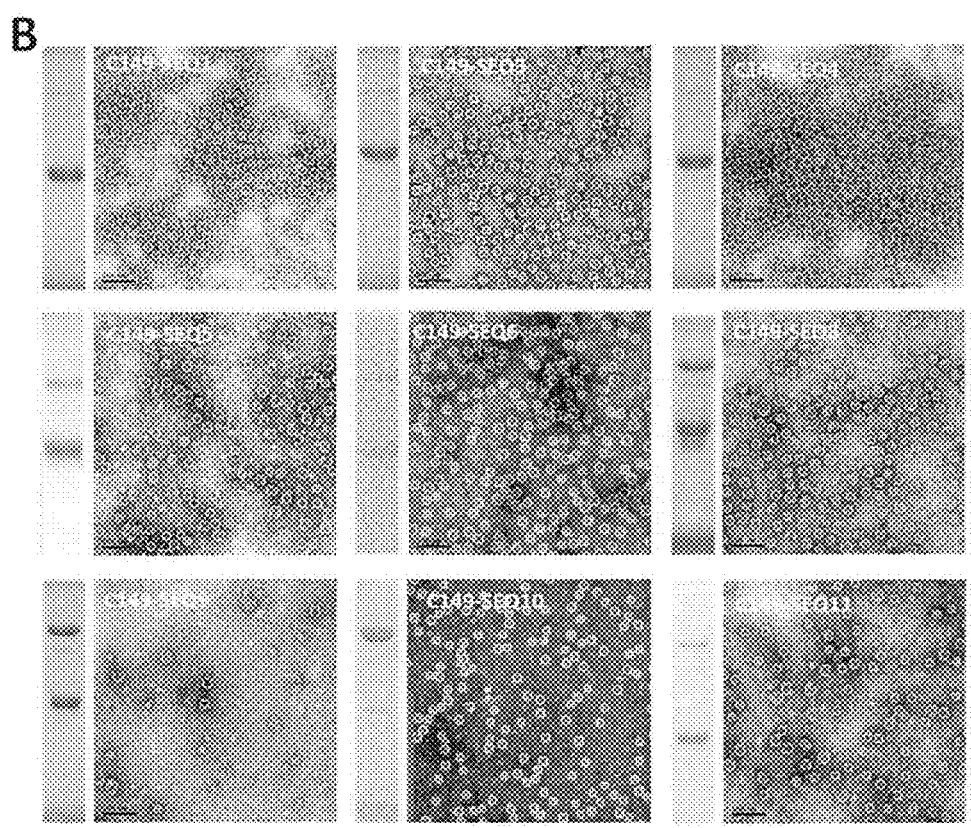

FIG. 5B showed the SDS-PAGE and TEM results of said 9 recombinant proteins. The results indicated that said 9 recombinant proteins had a purity of above 95%, and could be assembled into protein particles of a uniform size.

6.2 Evaluation of Reactivity of Said 9 Recombinant Proteins with Antibodies of sA Group 6.2.1 Preparation of Reaction Plates According to the method described in Example 1-1.2, reaction plates were prepared, and the coating antigens are said 9 recombinant proteins presenting polypeptides of interest.

6.2.2 Determination of reactivity of HBs-E6F6, HBs-E7G11, HBs-G12F5, HBs-E13C5 with said recombinant proteins by ELISA According to the method described in Example 1-1.2, the reactivity of HBs-E6F6, HBs-E7G11, HBs-G12F5, HBs-E13C5 with said recombinant proteins was determined.

6.2.3 Analysis on epitopes recognized by HBs-E6F6, HBs-E7G11, HBs-G12F5, HBs-E13C5

Figure 6:
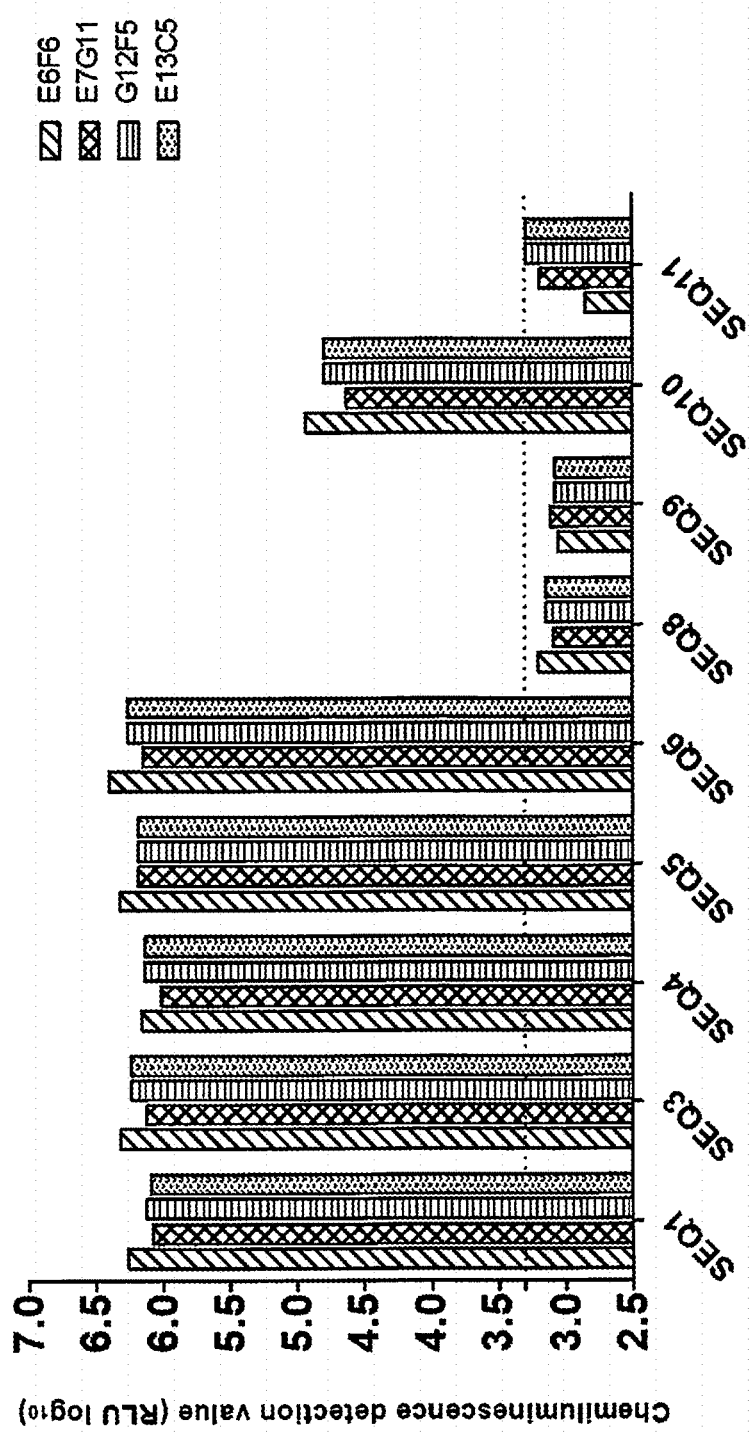
FIG. 6: Analysis on epitopes of HBs-E6F6, HBs-E7G11, HBs-G12F5, and HBs-E13C5.

The ELISA results in 6.2.2 are shown in FIG. 6. The results indicated that HBs-E6F6, HBs-E7G11, HBs-G12F5, HBs-E13C5 had good reactivity with the recombinant proteins presenting polypeptides SEQ1, SEQ3, SEQ4, SEQ5, SEQ6, SEQ10, but had no reactivity with the recombinant proteins presenting polypeptides SEQ8, SEQ9, SEQ11. The sequence analysis of these polypeptides showed that the common feature of the polypeptides SEQ1, SEQ3, SEQ4, SEQ5, SEQ6, SEQ10 lies in comprising HBsAg aa121-aa124, and the common feature of SEQ8, SEQ9, SEQ11 resided in not comprising an intact HBsAg aa121-124. Therefore, it could be concluded that HBs-E6F6, HBs-E7G11, HBs-G12F5, HBs-E13C5 recognized the same epitope, and the amino acid sequence of the shortest epitope recognized by them was HBsAg aa121-124, i.e. CKTC. ELISA results showed that the recombinant proteins C149-SEQ1 and 3-6 had comparable reactivity with antibodies, and had reactivity higher than C149-SEQ10. Therefore, the polypeptides SEQ1 and 3-6 were the preferred epitope peptides recognized by antibodies HBs-E6F6, HBs-E7G11, HBs-G12F5, HBs-E13C5. In addition, since the sequence of SEQ1 was shorter than SEQ3-6, SEQ1 was regarded as the preferred core epitope.

Example 7: Analysis on Sensitivity of HBs-E6F6 and HBs-E7G11 to the Amino Acid Mutations of the Epitope Peptide SEQ1

SEQ1 (GPCKTCT) was subjected to amino acid point-mutation, and 7 mutants were prepared. The amino acid sequences of said 7 mutant polypeptides were shown in Table 5. According to the method described in Example 6, recombinant proteins comprising the mutant polypeptides and C149/mut were prepared, and HBs-E6F6 and HBs-E7G11 were evaluated for their reactivity with said 7 mutant polypeptides.

TABLE 5

Amino acid sequences of mutant polypeptides

| Name | Mutated amino acid | Amino acid sequence |
|---|---|---|
| M1 | P120S | GSCKTCT |
| M2 | P120T | GTCKTCT |
| M3 | C121S | GPSKTCT |
| M4 | K122R | GPCRTCT |
| M5 | T123I | GPCKICT |
| M6 | C124S | GPCKTST |
| M7 | C121S/C124S | GPSKTST |
| SEQ1 | HBsAg aa119-aa125 | GPCKTCT |

Figure 7A:
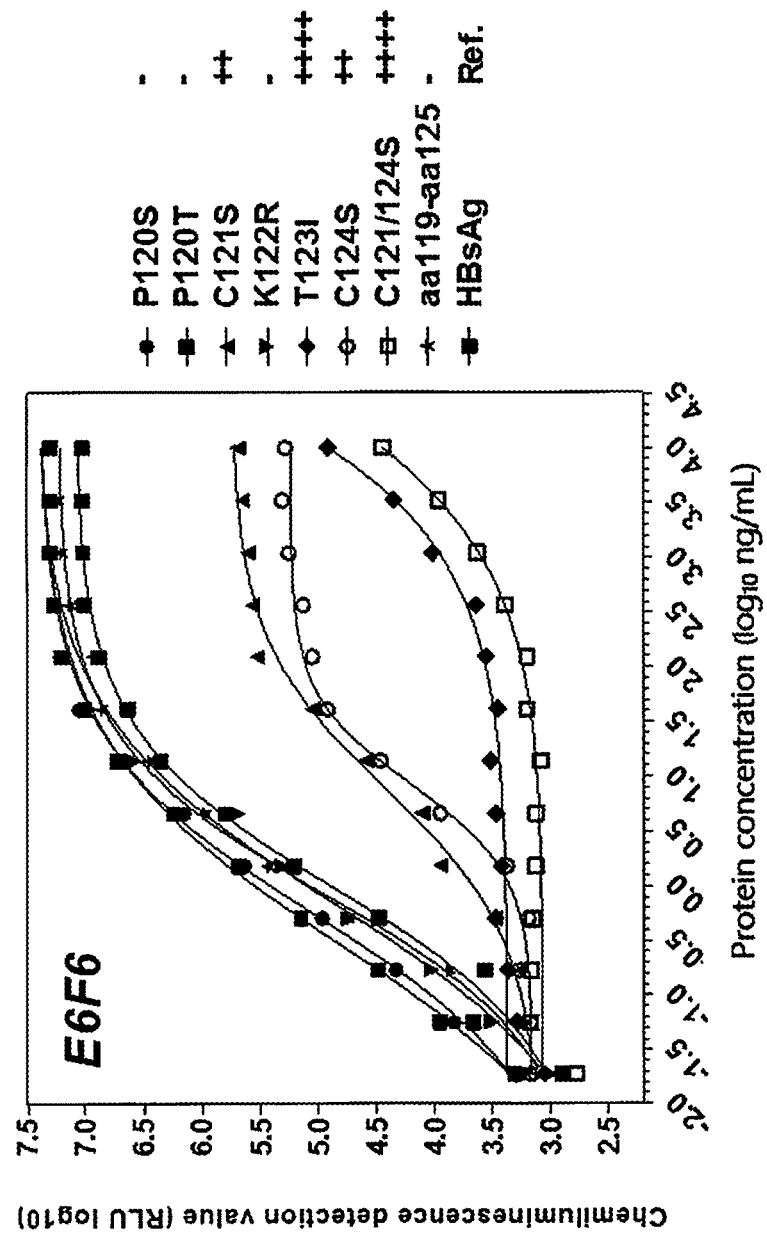
FIGS. 7A-7B: Analysis on sensitivity of HBs-E6F6/HBs-E7G11 to the amino acid mutations of the epitope peptide SEQ1, wherein "Ref." means that HBsAg is used as a reference antigen indicating antibody reactivity, "–" means that the reactivity is identical to that of HBsAg, "++" means that the reactivity is lower than that of HBsAg by 2 orders of magnitude ($\log_{10}$), "++++" means that the reactivity is lower than that of HBsAg by 4 orders of magnitude ($\log_{10}$).
Figure 7B:
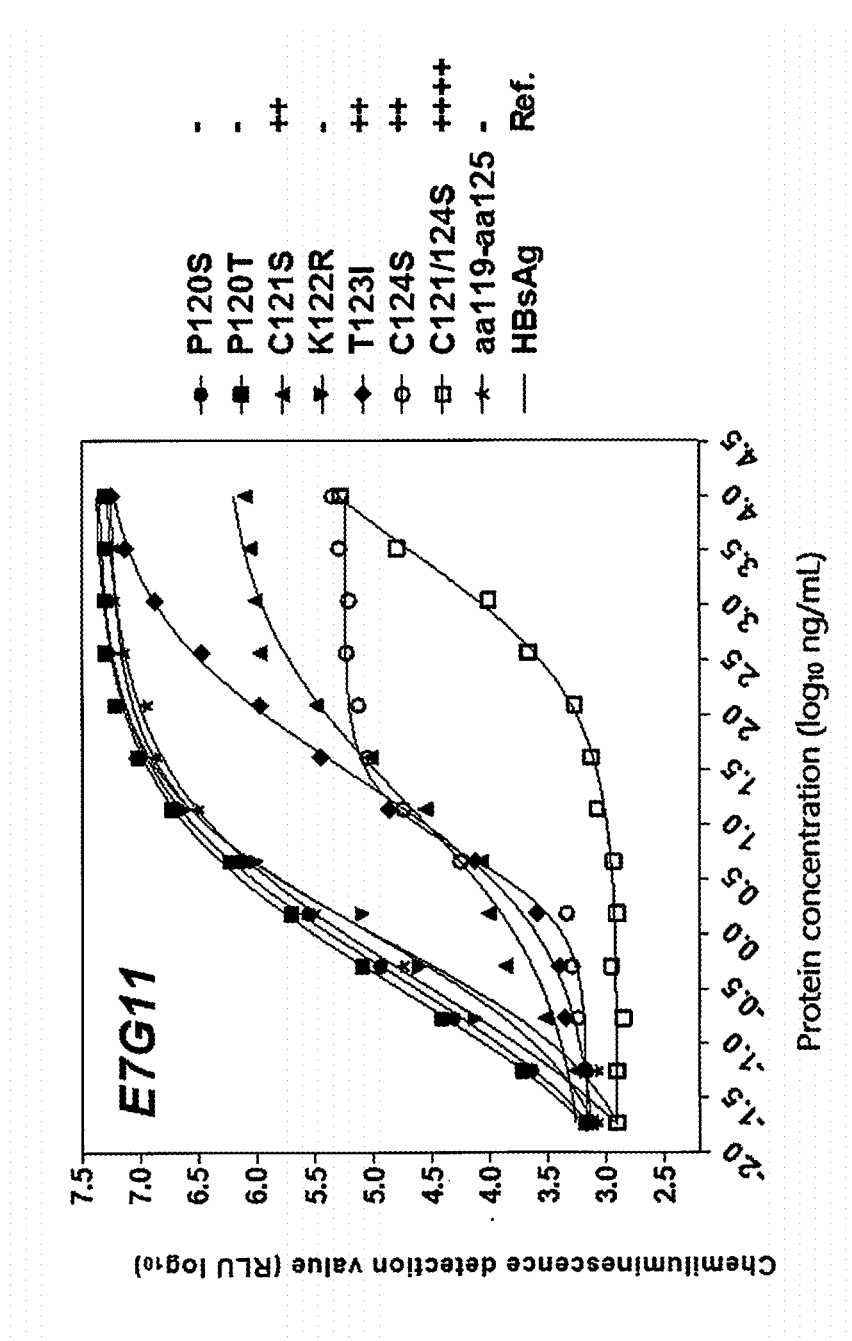
Figure 8A:
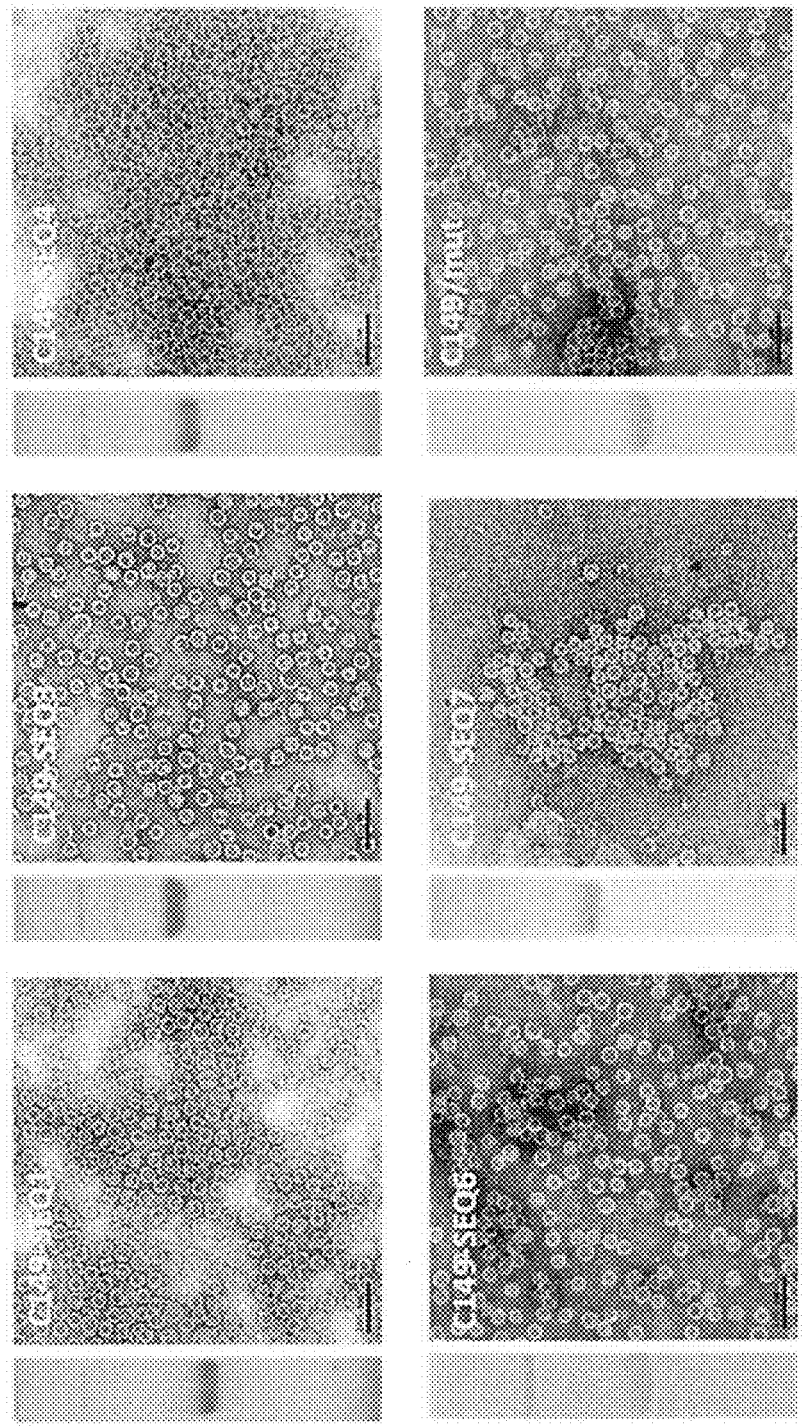
Figure 9A:
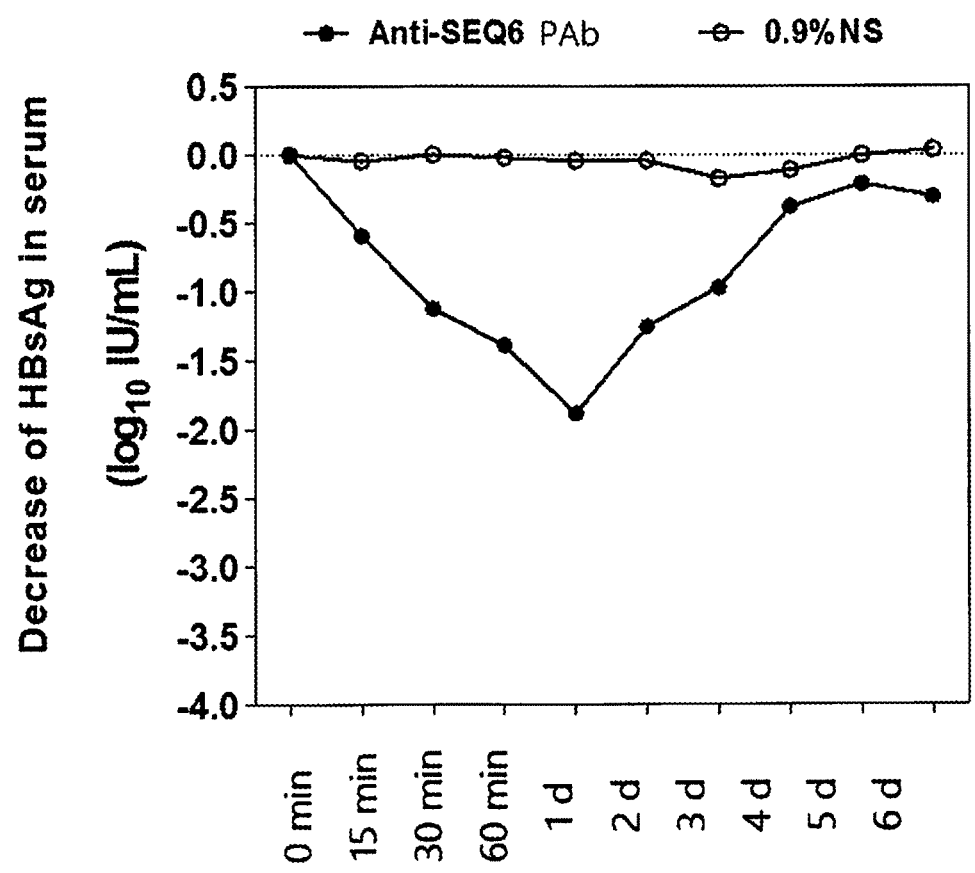
FIGS. 9A-9B: Evaluation of therapeutic effects of mouse blood-derived polyclonal antibodies.
Figure 9B:
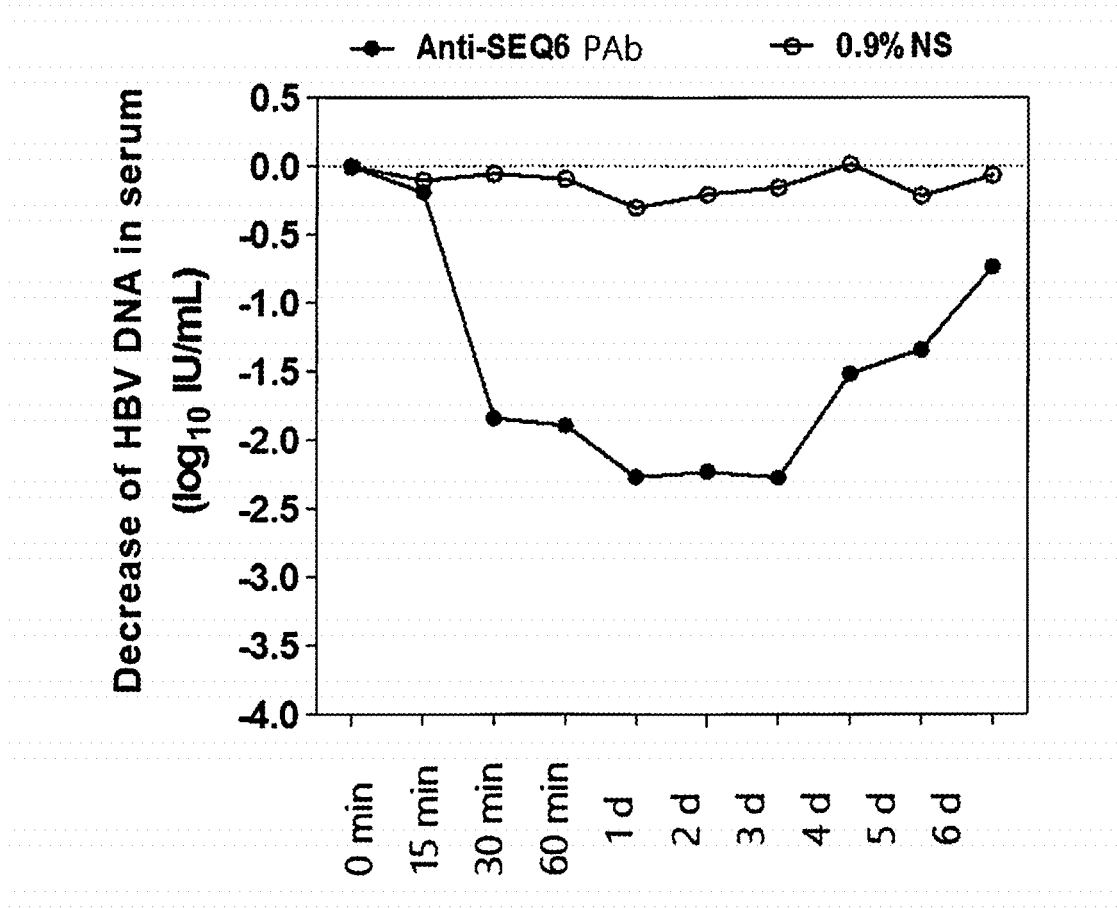
Figure 10A:
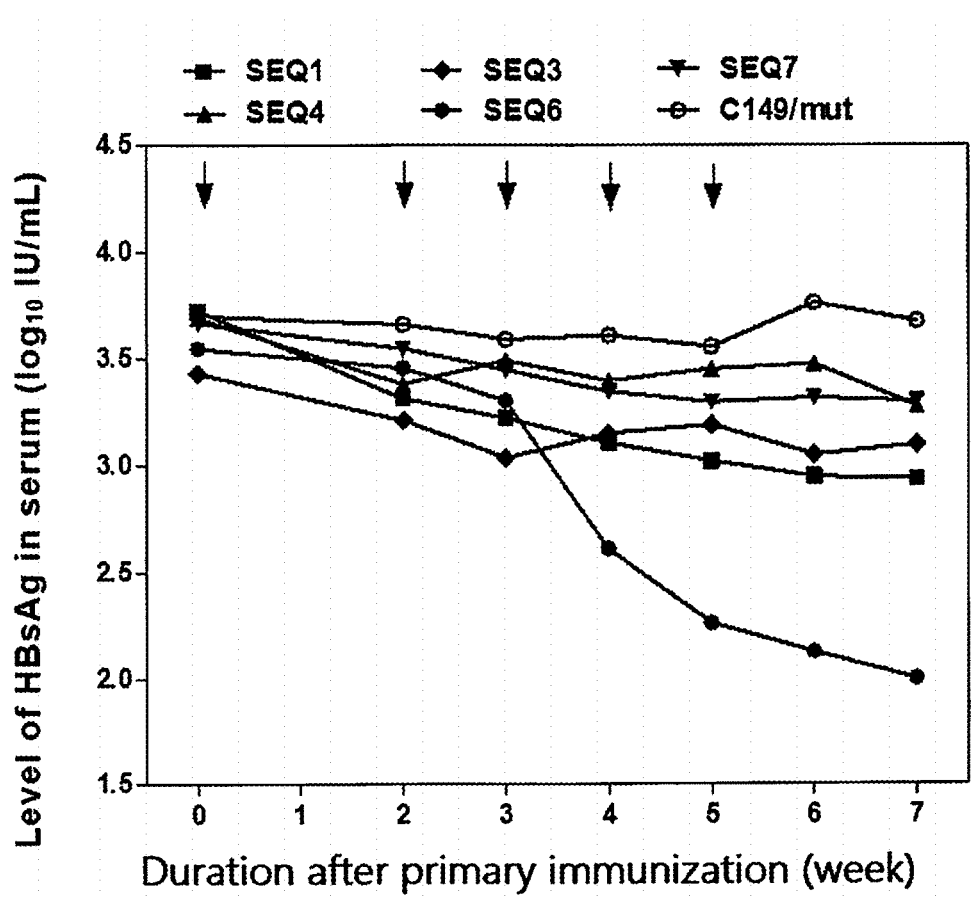
FIGS. 10A-10D: Evaluation of effects of said 5 recombinant proteins in the treatment of HBV transgenic mice.
Figure 10B:
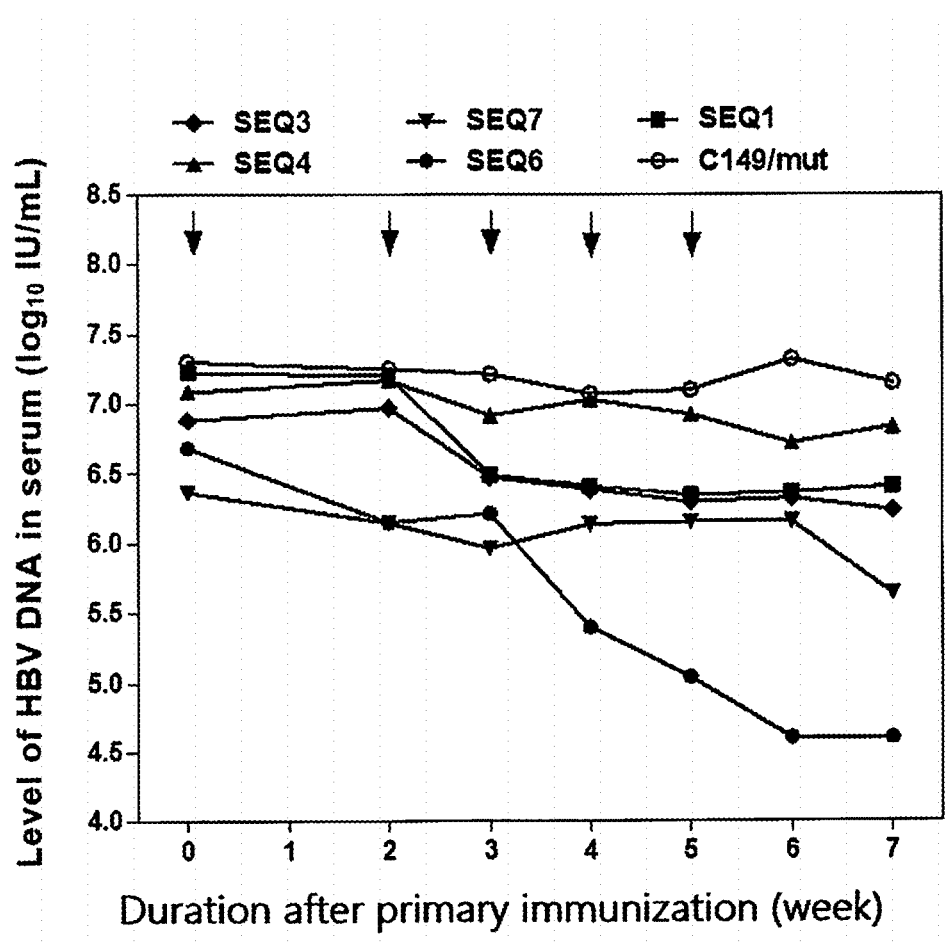
Figure 10C:
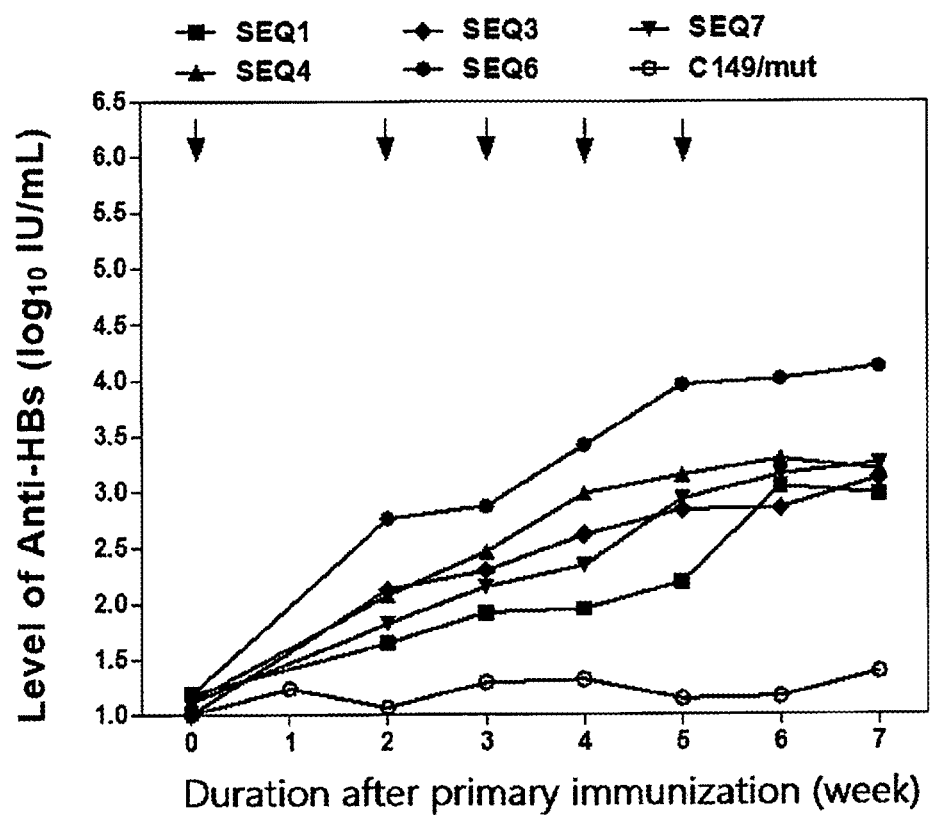
Figure 10D:
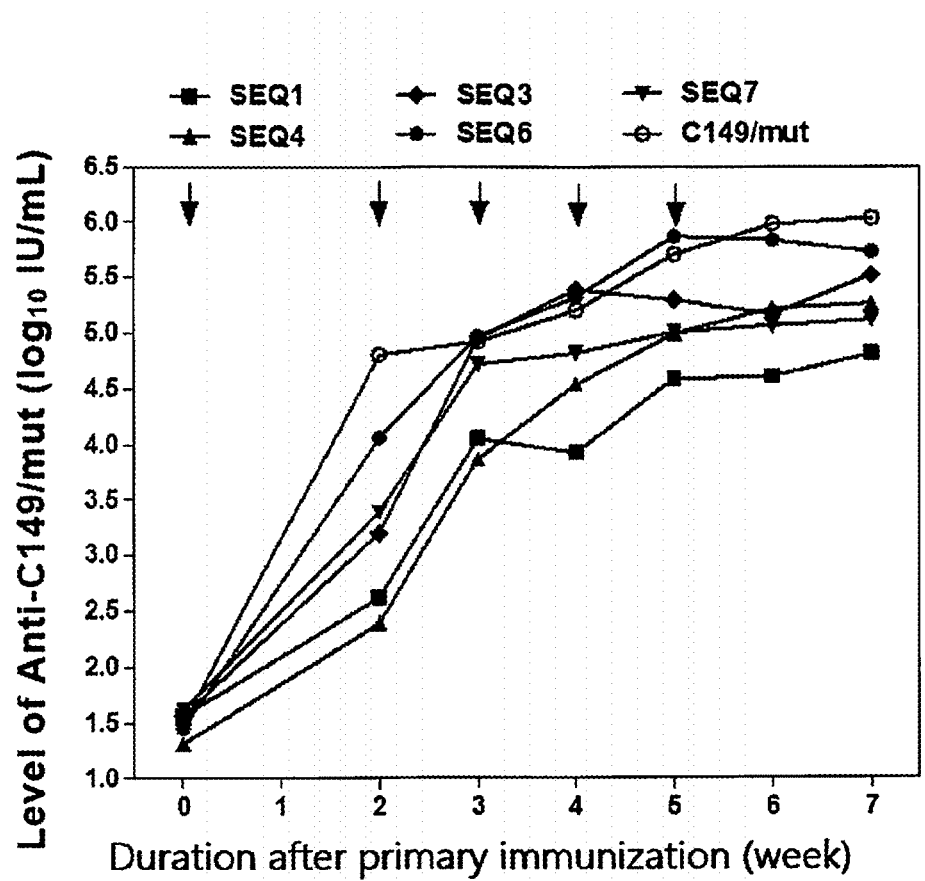

The results are shown in FIGS. 7A-7B. The results indicated that mutant M1 (P120S), mutant M2 (P120T), mutant M4 (K122R) were comparable to the epitope peptide SEQ1 with respect to the binding to antibody HBs-E6F6 and HBs-E7G11, while the binding of the other mutants to the antibodies was significantly decreased. It indicated that P120S, P120T, K122R mutation had no effect on the reactivity of HBs-E6F6 and HBs-E7G11 with the epitope SEQ1, while C121S, C124S, C121S/C124S, T123I mutation significantly decreased the reactivity of HBs-E6F6 and HBs-E7G11 with the epitope SEQ1.

Example 8: Preparation of Recombinant Proteins Comprising Epitope Peptides and Evaluation of their Immunogenicity 8.1 Preparation of Recombinant Proteins Comprising Epitope Peptides According to the method described in Example 6, C149/mut was used as carrier protein to present epitope peptides SEQ1, SEQ3, SEQ4, SEQ6, SEQ7, wherein SEQ3, SEQ4, SEQ6, SEQ7 were polypeptides obtained by extension of N and/or C-terminus of the preferred core epitope SEQ1 (i.e., comprising the core epitope SEQ1), from which 5 recombinant proteins (used as antigens for immunization) capable of forming nucleocapsid-like particles (CLP) were prepared.

As described in Example 6, 5 recombinant proteins C149-SEQ1, SEQ3, SEQ4, SEQ6, SEQ7 were prepared, and said 5 recombinant proteins were subjected to SDS-PAGE and were observed by transmission electron microscope. The results are shown in FIG. 8A. The results indicated that said 5 recombinant proteins had a purity of above 95%, and could be assembled into protein particles of a uniform size.

8.2 Evaluation of Immunogenicity of Recombinant Proteins Comprising Epitope Peptides 8.2.1 Immunization of Mice BALB/C mice were immunized with said 5 recombinant proteins and the carrier protein C149/mut (as control), respectively. Immunoadjuvant was aluminium hydroxide adjuvant, the immune dose was 3 μg/dose, the immunization route was intramuscular injection of lateral hind thigh, and the immune procedure was as followed: a boost immunization was performed every 2 weeks after primary immunization; immunization was performed for four times.

8.2.2 Determination of Anti-HBs Antibody Titer in Serum 8.2.2.1 Preparation of Reaction Plate According to the method described in Example 1-1.2, the reaction plate was prepared, the coating antigen was hepatitis B surface antigen protein (HBsAg) recombinantly expressed in CHO cells.

8.2.2.2 ELISA of Anti-HBs Antibody Titer in Serum

Sample dilution: mouse serum was diluted with PBS solution containing 20% new-born calf serum to 7 gradient concentrations, i.e. 1:100, 1:500, 1:2500, 1:12500, 1:62500, 1:312500, 1:1562500.

Sample reaction: 100 μL diluted sample was added to each well of the coated reaction plate, and the plate was placed in an incubator at 37° C. for 30 min.

Enzyme labelling reaction: after sample reaction was finished, the ELISA plate was washed with PBST (20 mM PB7.4, 150 mM NaCl, 0.1% Tween20) for 5 times, 100 μL GAM-HRP solution was added to each well, and the plate was placed in an incubator at 37° C. for 30 min.

Color development reaction: After the Enzyme labelling reaction, the ELISA plate was washed with PBST solution (20 mM PB7.4, 150 mM NaCl, 0.1% Tween20) for 5 times, 50 μL TMB colour developing reagent (provided by BEIJING WANTAI BIOLOGY PHARMACY CO., LTD) was added to each well, and the plate was placed in an incubator at 37° C. for 15 min.

Stopping reaction and value readout: After the color development reaction step was finished, 50 μL stopping buffer (provided by BEIJING WANTAI BIOLOGY PHARMACY CO., LTD) was added to each well of the ELISA plate, and OD450/630 value was read with ELIASA for each well.

Calculation of Anti-HBsAg antibody titer in serum: a regression curve was plotted with dilution factors of samples with a readout value between 0.2 and 2.0 and the readout values, the dilution factor of the sample at which the readout value was the double of the background value was calculated, and the dilution factor was used as Anti-HBsAg antibody titer in serum.

8.2.3 Determination of Anti-C149/Mut Antibody Titer in Serum 8.2.3.1 Preparation of Reaction Plates According to the method described in Example 1-1.2, reaction plates were prepared, and the antigen for coating was the fusion carrier protein C149/mut.

8.2.3.2 Determination of Anti-C149/Mut Antibody Titer in Serum by ELISA

According to the method described in Example 8.2.2.2, sample dilution, sample reaction, enzyme labelling reaction, color development reaction, stopping reaction and value readout, were carried out, and Anti-C149/mut antibody titer in serum was calculated.

8.2.4 Analysis of Immunogenicity of Recombinant Proteins Comprising Epitope Peptides By carrying out said steps, Anti-HBsAg antibody titer and Anti-C149/mut antibody titer in serum were obtained. The results are shown in FIG. 8B. The results indicated that the recombinant proteins comprising the epitope peptides SEQ1, SEQ3, SEQ4, SEQ6, SEQ7 induced a high titer of Anti-HBsAg in BALB/C mice, while C149/mut alone could not induce a high titer of Anti-HBsAg.

Example 9: Evaluation of Therapeutic Effect of Mouse Blood-Derived Anti-SEQ6 Polyclonal Antibodies 9.1 Preparation of Mouse Blood-Derived Anti-SEQ6 Polyclonal Antibodies 9.1.1 Immunization of Mice According to the method described in Example 8-8.2.1, BALB/C mice were immunized with an immunogen that was a recombinant protein comprising SEQ6 (C149-SEQ6).

9.1.2 Purification of Mouse Blood-Derived Anti-SEQ6 Polyclonal Antibodies

After immune procedure was completed, titer of Anti-HBsAg antibody in serum of mice reached a high level, blood was taken from periorbital venous plexus for several times. After purification by ammonium sulfate precipitation and Protein A affinity chromatography, purified polyclonal antibodies were obtained.

9.2 Evaluation of Therapeutic Effect of Mouse Blood-Derived Anti-SEQ6 Polyclonal Antibodies Mouse blood-derived Anti-SEQ6 polyclonal antibodies were injected to caudal vein of HBV transgenic mice, changes in HBV DNA and HBsAg in serum were monitored. The results are shown in FIGS. 9A-9B. The results indicated that polyclonal antibodies, obtained by immunization of mice with C149-SEQ6, significantly decreased HBV DNA and HBsAg level in HBV transgenic mice, and were effective in clearing up HBV.

Example 10: Effect of Recombinant Proteins in the Treatment of HBV Transgenic Mice 10.1 Immunization of Mice HBV transgenic mouse model was used to evaluate the therapeutic effect of said 5 recombinant proteins (C149-SEQ1, C149-SEQ3, C149-SEQ4, C149-SEQ6, C149-SEQ7) obtained in Example 8, and the carrier protein C149/mut was used as control. Immunoadjuvant was aluminium hydroxide adjuvant, the immune dose was 12 μg/dose, the immunization route was intramuscular injection of lateral hind thigh, and the immune procedure was as following: a boost immunization was performed 2 weeks after primary immunization, followed by a boost immunization every week, i.e. immunization was performed at week 0, 2, 3, 4, 5, i.e. immunization was performed for five times.

10.2 Determination of Antibody Titer in Serum

According to the methods described in Example 8-8.2.2 and 8.2.3, serum antibody titer of Anti-HBsAg and Anti-C149/mut was determined, and virological indexes, HBV DNA and HBsAg level in serum of mice were monitored.

10.3 Analysis on Therapeutic Effect of the Recombinant Proteins

The results are shown in FIGS. 10A-10D. The results indicated that in groups receiving immunotherapy of recombinant proteins, Anti-HBsAg and Anti-C149/mut were detected in serum of mice, and HBV DNA and HBsAg level in serum of mice were decreased to different extents. By contrast, in control group, no Anti-HBsAg was produced in serum of mice, and HBV DNA and HBsAg level in serum did not decrease. The Example shows that the epitopes and epitope peptides identified by the invention are effective targets for treatment of HBV infection. The recombinant proteins produced based on these epitopes and epitope peptides have potential for treating chronic HBV infection. In particular, the recombinant proteins comprising the epitope peptide SEQ1-SEQ7 may be used as protein vaccines to change the immunotolerant state directed to HBV in HBV transgenic mice and induce effective, specific and therapeutic anti-HBV immune response.

Example 11: Construction and Evaluation of Recombinant Proteins Based on Different Carrier Proteins and SEQ6

11.1 Construction of 3 Fusion Expression Vectors

According to the method described in Example 6, 3 carrier proteins were constructed, which were C149/mut (SEQ ID NO: 43), C183/mut (SEQ ID NO: 44), WHC149/mut (SEQ ID NO: 45), respectively. C149/mut was obtained by engineering 149 amino acid residues at N-terminus of HBV core protein, C183/mut was obtained by engineering 183 amino acid residues of full-length HBV core protein, and WHC149/mut was obtained by engineering 149 amino acid residues at N-terminus of woodchuck hepatitis virus core protein (the engineering method was described in 6.1). SEQ6 was ligated to the three vectors to get recombinant proteins C149-SEQ6, C183-SEQ6, and WHC149-SEQ6, respectively.

Figure 11A:
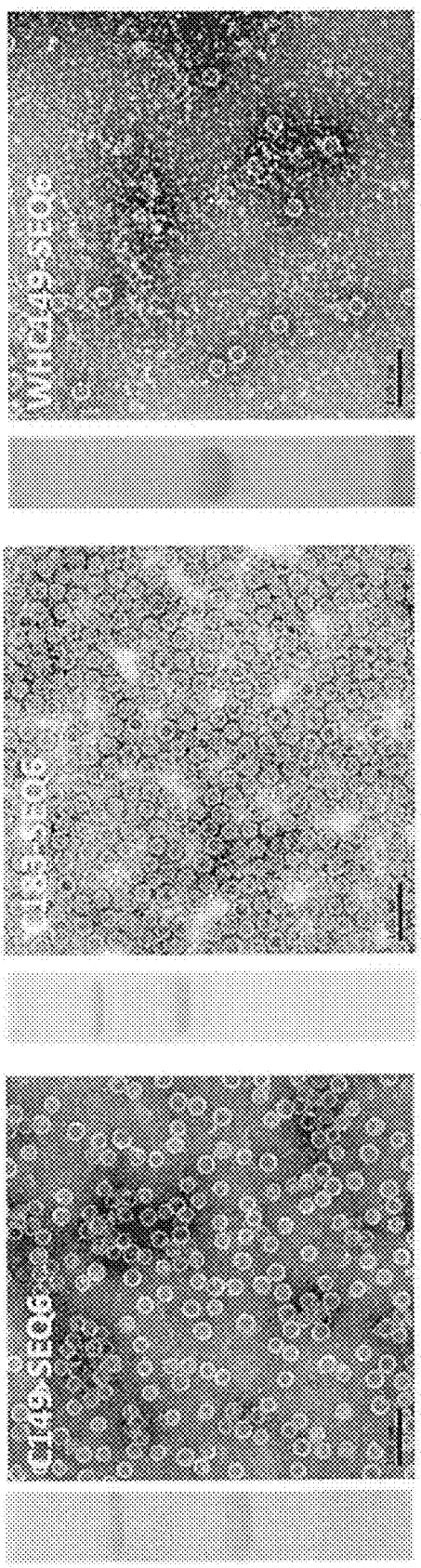
FIGS. 11A-11E: The preparation of 3 recombinant proteins comprising epitope peptides and evaluation of their therapeutic effects.
Figure 11B:
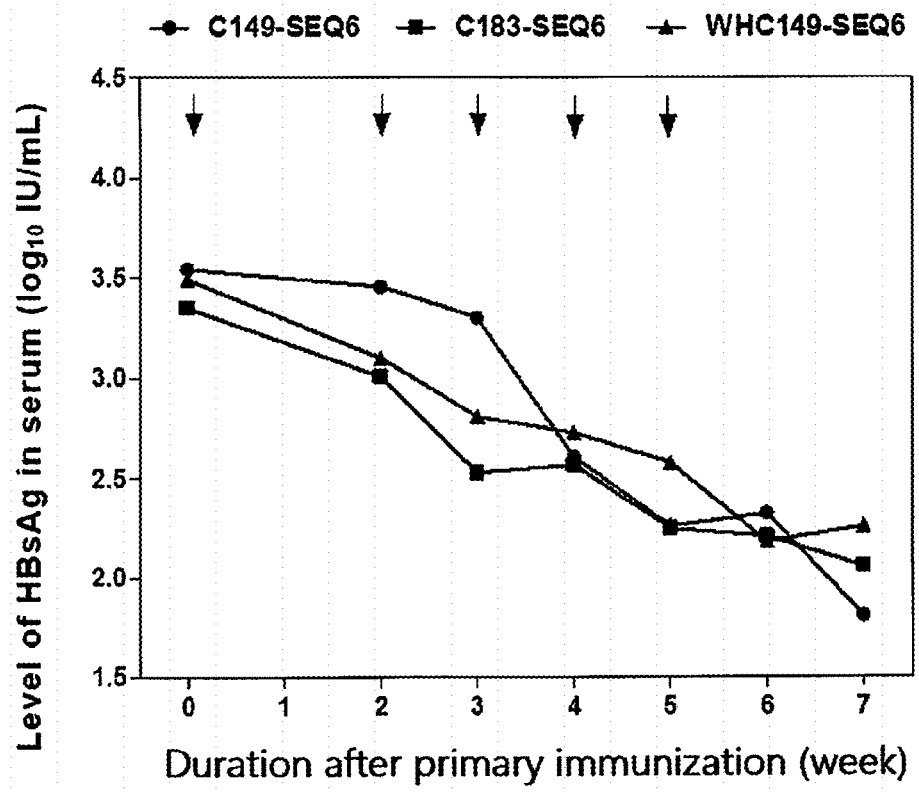
Figure 11C:
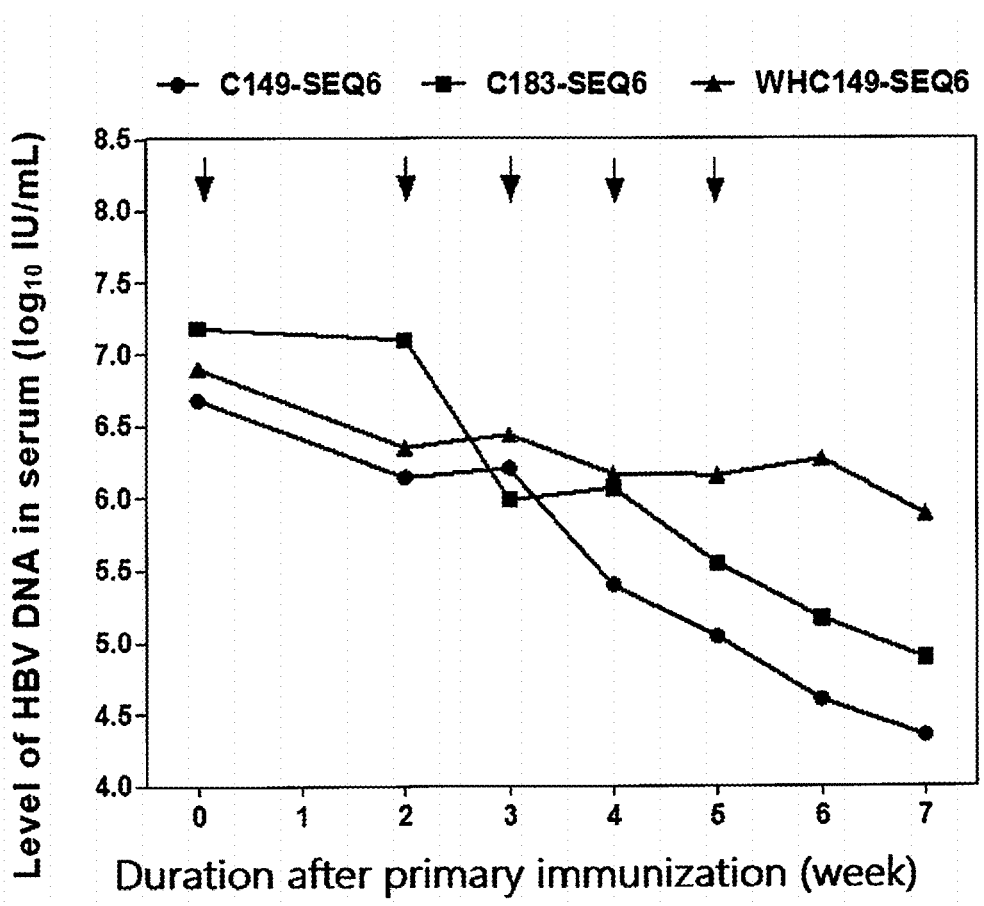
Figure 11D:
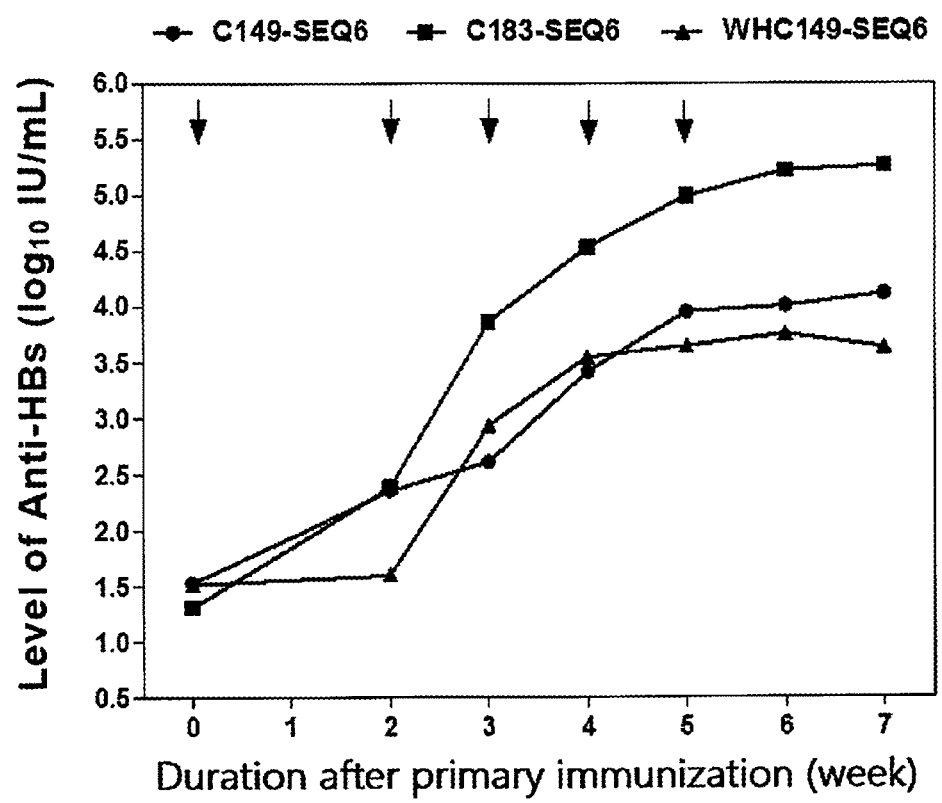
Figure 11E:
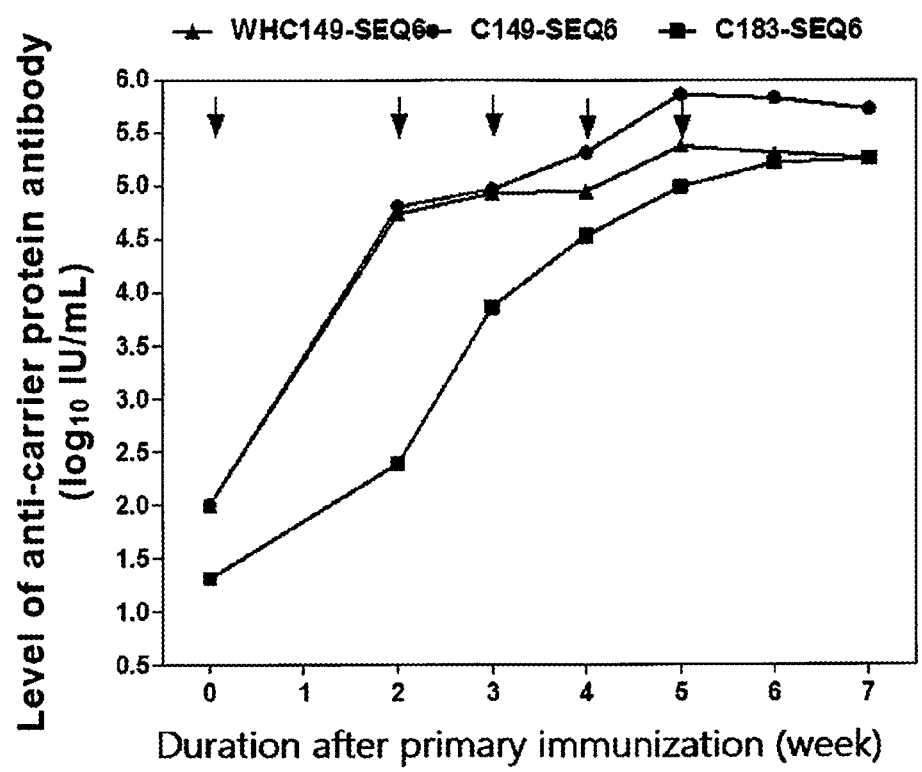

11.2 Expression and Purification of 3 Different Carrier Recombinant SEQ6 Vaccines According to the method described in 6.2, 3 recombinant proteins (C149-SEQ6, C183-SEQ6, WHC149-SEQ6) were expressed and purified. The proteins of interest obtained were subjected to SDS-PAGE, and assembly state of the protein particles was identified by transmission electron microscope. The results are shown in FIG. 11A. The results indicated that the 3 recombinant proteins obtained had a purity above 95%, and could be assembled into protein particles of a uniform size.

11.3 Effects of Said 3 Recombinant Proteins in the Treatment of HBV Transgenic Mice HBV transgenic mouse model was used to evaluate the therapeutic effect of said 3 recombinant proteins obtained in 11.2 as protein vaccines. Immunoadjuvant was aluminium hydroxide adjuvant, the immune dose was 12 μg/dose, and the immune procedure was as followed: a boost immunization was performed 2 weeks after primary immunization, followed by a boost immunization every week, i.e. immunization was performed at week 0, 2, 3, 4, 5, i.e. immunization was performed for five times.

According to the methods described in Example 8-8.2.2 and 8.2.3, serum antibody titer of Anti-HBsAg and anti-carrier was determined, and virological indexes, HBV DNA and HBsAg level in serum of mice were monitored.

The results are shown in FIGS. 10A-10D. The results indicated that in groups receiving immunotherapy of recombinant proteins, Anti-HBsAg and anti-carrier antibody were detected in serum of mice, and HBV DNA and HBsAg level in serum of mice reduced to different extents. By contrast, in control group, no Anti-HBsAg was produced in serum of mice, and HBV DNA and HBsAg level in serum did not reduce. The Example showed that different carrier proteins may be used to present the epitopes and epitope peptides identified by the invention, and the recombinant proteins produced therefrom had potential for treating chronic HBV infection. Such recombinant proteins may be used as protein vaccines to change the immunotolerant state directed to HBV in HBV transgenic mice and induced effective, specific and therapeutic anti-HBV immune response.

Similarly, based on C149/mut (SEQ ID NO: 43), C183/mut (SEQ ID NO: 44) or WHC149/mut (SEQ ID NO: 45), and SEQ1-5, 7 and 10, the recombinant proteins C149-SEQ1-5, 7, 10; C183-SEQ1-5, 7, 10; and WHC149-SEQ1-5, 7, 10 were also designed and constructed. The amino acid sequences of these recombinant proteins were shown in Table 1.

Example 12: Construction and Expression of Recombinant Proteins Based on CRM197 or Fragments Thereof In the Example, a series of recombinant proteins were designed and constructed based on CRM197 or fragments thereof and SEQ6.

The amino acid sequence of CRM197 is set forth in SEQ ID NO: 42, which consists of 535 amino acids. An exemplary fragment of CRM197 is CRM 389, consisting of 389 amino acids at N-terminus of CRM197. Another exemplary fragment of CRM197 is CRM A, consisting of 190 amino acids at N-terminus of CRM197.

Figure 12:
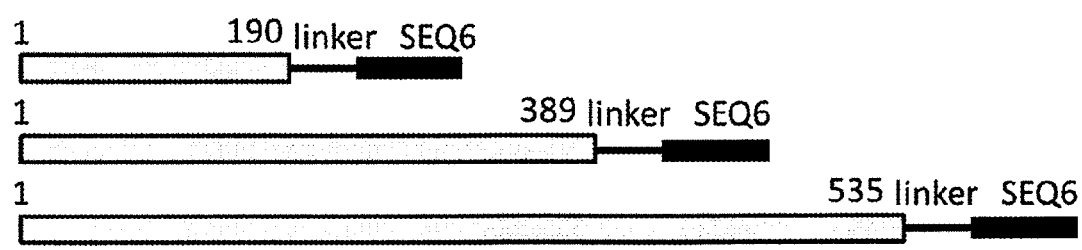
FIG. 12: Illustration of CRM197-SEQ6, CRM389-SEQ6, CRMA-SEQ6 recombinant protein.

As shown in FIG. 12, SEQ6 was linked to C-terminus of CRM197, CRM389 or CRMA via a linker, wherein the amino acid sequence of the linker was GGGGSGGGGSGGGGS (SEQ ID NO: 46). The main function of the linker was to promote the relatively independent folding of the two peptides linked thereby to obtain a high biological activity. The recombinant proteins thus obtained were designated as CRM197-SEQ6, CRM389-SEQ6 and CRMA-SEQ6, respectively.

Genes of interest encoding CRM197-SEQ6, CRM389-SEQ6 and CRMA-SEQ6 were constructed, the genes of interest were separately ligated to pTO-T7 prokaryotic expression vector (Luo Wenxin et al., Chinese Journal of Biotechnology, 2000, 16:53-57), and were transformed into ER2566 bacteria; plasmids were extracted, positive expression clones comprising gene fragments of interest were obtained after identification by NdeI/SalI enzyme digestion.

Three recombinant proteins CRM197-SEQ6, CRM389-SEQ6 and CRMA-SEQ6 were expressed and purified according to the methods described in Example 6-6.2, and the therapeutic effect of said 3 recombinant proteins were evaluated by the methods described in Example 11.

Similarly, based on CRM197 or fragments thereof as well as SEQ1-5, 7 and 10, recombinant proteins CRM197-SEQ1-5, 7, 10; CRM389-SEQ1-5, 7, 10; and CRMA-SEQ1-5, 7, 10 were designed and constructed. The amino acid sequences of these recombinant proteins were shown in Table 1.

Although the specific embodiments of the invention have been described in details, those skilled in the art would understand that, according to all the disclosed teachings, various modifications and changes can be made without departing from the sprit or scope of the invention as generally described, and that such modifications and changes are within the scope of the present invention. The scope of the present invention is given by the appended claims and any equivalents thereof.

The invention claimed is:

1. A monoclonal antibody or an antigen binding fragment thereof, wherein the monoclonal antibody specifically binds to positions 119 to 125 of HBsAg protein of HBV, and is selected from one of the following monoclonal antibodies:
   1) the monoclonal antibody produced by the hybridoma cell line HBs-E6F6, wherein the hybridoma cell line HBs-E6F6 is deposited in China Center for Type Culture Collection (CCTCC), with a deposition number of CCTCC NO. C201270;
   2) the monoclonal antibody produced by the hybridoma cell line HBs-E7G11, wherein the hybridoma cell line HBs-E7G11 is deposited in China Center for Type Culture Collection (CCTCC), with a deposition number of CCTCC NO. C201271;
   3) the monoclonal antibody produced by the hybridoma cell line HBs-G12F5, wherein the hybridoma cell line HBs-G12F5 is deposited in China Center for Type Culture Collection (CCTCC), with a deposition number of CCTCC NO. C201272;
   4) the monoclonal antibody produced by the monoclonal antibody produced by hybridoma cell line HBs-E13C5, wherein the hybridoma cell line HBs-E13C5 is deposited in China Center for Type Culture Collection (CCTCC), with a deposition number of CCTCC NO. C201273 and
   5) the monoclonal antibody or an antigen binding fragment selected from a humanized antibody, a chimeric antibody or a single chain antibody made from any of the monoclonal antibodies as described in 1-4 above.

2. The monoclonal antibody or antigen binding fragment thereof of claim 1, wherein the monoclonal antibody or antigen binding fragment thereof has one or more of the following features:
   (1) the antigen binding fragment thereof is selected from a group consisting of Fab, Fab', F(ab')$_2$, Fd, Fv, dAb, complementary determining region fragment, or a single chain antibody;
   (2) the monoclonal antibody binds to HBsAg protein with a $K_D$ of less than about $10^{-5}$ M, or less than about $10^{-6}$ M, $10^{-7}$ M, $10^{-8}$ M, $10^{-9}$ M, $10^{-10}$ M or less;
   (3) the monoclonal antibody comprises non-CDR region, and the non-CDR region is from species other than murine species; and
   (4) the monoclonal antibody is capable of reducing serum level of HBV DNA and/or HBsAg in a subject.

3. The monoclonal antibody or antigen binding fragment thereof of claim 2, wherein the single chain antibody is scFv, and/or, the chimeric antibody is a human-mouse chimeric antibody.

4. The monoclonal antibody or antigen binding fragment thereof of claim 2, wherein the non-CDR region is from human antibody.

5. An isolated nucleic acid molecule, encoding the monoclonal antibody or antigen binding fragment thereof of claim 1.

6. A vector, comprising the isolated nucleic acid molecule of claim 5.

7. A host cell, comprising the isolated nucleic acid molecule according to claim 5 or a vector comprising the isolated nucleic acid molecule.

8. A method for producing the monoclonal antibody or antigen binding fragment thereof of claim 1, comprising
   1) expressing an isolated nucleic acid molecule encoding the monoclonal antibody or antigen binding fragment thereof in a host cell, to produce the monoclonal antibody or antigen binding fragment thereof; and
   2) isolating the monoclonal antibody or antigen binding fragment thereof.

9. A hybridoma cell line, selected from:
   1) hybridoma cell line HBs-E6F6, deposited in China Center for Type Culture Collection (CCTCC), with a deposition number of CCTCC NO. C201270;
   2) hybridoma cell line HBs-E7G11, deposited in China Center for Type Culture Collection (CCTCC), with a deposition number of CCTCC NO. C201271;
   3) hybridoma cell line HBs-G12F5, deposited in China Center for Type Culture Collection (CCTCC), with a deposition number of CCTCC NO. C201272; and
   4) hybridoma cell line HBs-E13C5, deposited in China Center for Type Culture Collection (CCTCC), with a deposition number of CCTCC NO. C201273.

10. A kit for detecting the presence or level of HBsAg protein in a sample or for diagnosing whether a subject is infected by HBV, comprising the monoclonal antibody or antigen binding fragment thereof of claim 1.

11. The kit according to claim 10, wherein the monoclonal antibody or antigen binding fragment thereof further comprises a detectable marker.

12. The kit according to claim 11, wherein the detectable marker comprised in the monoclonal antibody or antigen binding fragment thereof is selected from a radioisotope, a fluorescent substance, a luminescent substance, a chromophoric substance and an enzyme.

13. The kit according to claim 10, wherein the kit further comprises a second antibody that specifically recognizes the monoclonal antibody or antigen binding fragment thereof; optionally, the second antibody further comprises a detectable marker.

14. The kit according to claim 13, wherein the detectable marker comprised in the second antibody is selected from a radioisotope, a fluorescent substance, a luminescent substance, a chromophoric substance and an enzyme.

15. A method for detecting the presence or level of HBsAg protein in a sample, comprising contacting the monoclonal antibody or antigen binding fragment thereof of claim 1 with the sample, and detecting any binding between the monoclonal antibody or antigen binding fragment thereof and HBsAg protein.

16. A method for diagnosing whether a subject is infected by HBV, comprising (1) contacting the monoclonal antibody or antigen binding fragment thereof of claim 1 with a sample from a subject that is suspected to be infected by HBV, and (2) detecting the presence of HBV in the sample by detecting any binding between the monoclonal antibody or antigen binding fragment thereof and HBsAg protein.

17. A pharmaceutical composition comprising the monoclonal antibody or antigen binding fragment thereof of claim 1, and a pharmaceutically acceptable carrier and/or excipient.

18. A method for preventing or treating HBV infection or a disease associated with HBV infection in a subject, comprising administering a prophylactically or therapeutically effective amount of the monoclonal antibody or antigen binding fragment thereof of claim 1 to a subject in need thereof.

19. The method according to claim 18, wherein the disease associated with HBV infection is hepatitis B.

20. A method for reducing serum level of HBV DNA and/or HBsAg in a subject, comprising administering to a subject infected with HBV and in need of reducing serum level of HBV DNA and/or HBsAg an effective amount of one of the following:
(1) the monoclonal antibody or antigen binding fragment thereof of claim 1; and
(2) a monoclonal antibody or an antigen binding fragment thereof, capable of blocking the binding of HBsAg protein to the monoclonal antibody or antigen binding fragment thereof as defined in (1) by at least 50%, at least 60%, at least 70%, at least 80%, at least 90%, at least 95% or at least 99%.

21. The monoclonal antibody or antigen binding fragment thereof according to claim 1, wherein the antibody is a humanized antibody.

22. The monoclonal antibody or antigen binding fragment thereof according to claim 1, wherein the antibody is a chimeric antibody.

23. The monoclonal antibody or antigen binding fragment thereof according to claim 1, wherein the antibody is a single chain antibody.

\* \* \* \* \*